United States Patent
Bae et al.

(10) Patent No.: US 9,714,903 B2
(45) Date of Patent: Jul. 25, 2017

(54) CASE FOR SPECIMEN ANALYZING KIT, KIT FOR SPECIMEN ANALYZING, SPECIMEN ANALYSIS APPARATUS AND CONTROL METHOD OF SPECIMEN ANALYSIS APPARATUS

(71) Applicant: INFOPIA CO., LTD., Anyang-si, Gyeonggi-do (KR)

(72) Inventors: Byeong Woo Bae, Anyang-si (KR); Sung Dong Lee, Anyang-si (KR); Rae Ho Kang, Anyang-si (KR); Ji Hun Shin, Anyang-si (KR); Ju Pyo Hong, Anyang-si (KR)

(73) Assignee: OSANG HEALTHCARE CO., LTD., Anyang-si (KR)

( * ) Notice: Subject to any disclaimer, the term of this patent is extended or adjusted under 35 U.S.C. 154(b) by 89 days.

(21) Appl. No.: 14/013,907

(22) Filed: Aug. 29, 2013

(65) Prior Publication Data

US 2014/0065032 A1     Mar. 6, 2014

(30) Foreign Application Priority Data

| Aug. 31, 2012 | (KR) | 10-2012-0096465 |
| Aug. 31, 2012 | (KR) | 10-2012-0096466 |
| Aug. 31, 2012 | (KR) | 10-2012-0096467 |
| Aug. 31, 2012 | (KR) | 10-2012-0096468 |
| Aug. 31, 2012 | (KR) | 10-2012-0096617 |
| Aug. 31, 2012 | (KR) | 10-2012-0096618 |
| Aug. 31, 2012 | (KR) | 10-2012-0096619 |
| Jun. 11, 2013 | (KR) | 10-2013-0066450 |

(51) Int. Cl.
*G01N 21/78* (2006.01)
*G01N 21/84* (2006.01)
(Continued)

(52) U.S. Cl.
CPC .............. *G01N 21/75* (2013.01); *B01L 3/502* (2013.01); *G01N 21/78* (2013.01); *G01N 21/8483* (2013.01); *G01N 2201/0221* (2013.01)

(58) Field of Classification Search
None
See application file for complete search history.

(56) References Cited

U.S. PATENT DOCUMENTS

| 4,791,461 A | 12/1988 | Kishimoto et al. |
| 5,424,035 A | 6/1995 | Hones et al. |

(Continued)

FOREIGN PATENT DOCUMENTS

| CN | 1773288 A | 5/2006 |
| CN | 1922488 A | 2/2007 |

(Continued)

*Primary Examiner* — Neil N Turk
(74) *Attorney, Agent, or Firm* — Birch, Stewart, Kolasch & Birch, LLP

(57) ABSTRACT

Provided is a specimen analysis apparatus. The specimen analysis apparatus includes an image photographing unit photographing an identification code disposed on a kit for specimen analyzing and a specimen reaction result reacting by injecting a specimen into the kit for specimen analyzing and a main body on which the image photographing unit is mounted. The image photographing unit photographs the identification code and the specimen reaction result with a time difference.

11 Claims, 68 Drawing Sheets

(51) Int. Cl.
*B01L 3/00* (2006.01)
*G01N 21/75* (2006.01)

(56) References Cited

U.S. PATENT DOCUMENTS

| | | | |
|---|---|---|---|
| 6,010,663 A | 1/2000 | Bachand | |
| 6,203,757 B1 | 3/2001 | Lu et al. | |
| 2002/0009390 A1* | 1/2002 | Lappe | B01L 3/502 |
| | | | 436/165 |
| 2002/0114735 A1 | 8/2002 | Markart | |
| 2002/0132267 A1 | 9/2002 | Wong | |
| 2004/0171173 A1 | 9/2004 | Eckermann et al. | |
| 2005/0201898 A1* | 9/2005 | Borich | G01N 21/78 |
| | | | 422/82.05 |
| 2006/0292040 A1* | 12/2006 | Wickstead | G01N 21/8483 |
| | | | 422/82.05 |
| 2007/0081920 A1 | 4/2007 | Murphy et al. | |
| 2007/0148046 A1 | 6/2007 | Nakaya | |
| 2008/0112848 A1 | 5/2008 | Huffstodt et al. | |
| 2009/0163367 A1 | 6/2009 | Yoo | |
| 2009/0320623 A1 | 12/2009 | Matallana-Kielmann | |
| 2010/0035357 A1 | 2/2010 | Geva et al. | |
| 2010/0311154 A1 | 12/2010 | Bae et al. | |
| 2011/0275162 A1 | 11/2011 | Xie et al. | |
| 2012/0178101 A1* | 7/2012 | Bae | G01N 21/8483 |
| | | | 435/7.4 |
| 2012/0305394 A1 | 12/2012 | Bae et al. | |

FOREIGN PATENT DOCUMENTS

| | | |
|---|---|---|
| CN | 102112872 A | 6/2011 |
| CN | 102549426 A | 7/2012 |
| EP | 2151686 A1 | 2/2010 |
| EP | 2474828 A2 | 7/2012 |
| JP | 2000-171427 A | 6/2000 |
| JP | 2004-534944 A | 11/2004 |
| JP | 2006-119065 A | 5/2006 |
| JP | 2006-266882 A | 10/2006 |
| JP | 2007-108174 A | 4/2007 |
| JP | 2007-178251 A | 7/2007 |
| KR | 10-0136998 B1 | 4/1998 |
| KR | 10-1998-0024133 A | 7/1998 |
| KR | 20-0208986 Y1 | 1/2001 |
| KR | 20-0299628 Y1 | 1/2003 |
| KR | 20-0357467 Y1 | 7/2004 |
| KR | 10-2006-0064351 A | 6/2006 |
| KR | 10-0680267 B1 | 2/2007 |
| KR | 20-2009-0002540 U | 3/2009 |
| KR | 10-0949114 B1 | 3/2010 |
| KR | 10-2011-0024747 A | 3/2011 |
| KR | 10-1044556 B1 | 6/2011 |
| KR | 10-2013-0001158 A | 1/2013 |
| WO | WO 02/08729 A1 | 1/2002 |
| WO | WO 2012/070111 A1 | 5/2012 |

* cited by examiner

FIG. 1
(a)
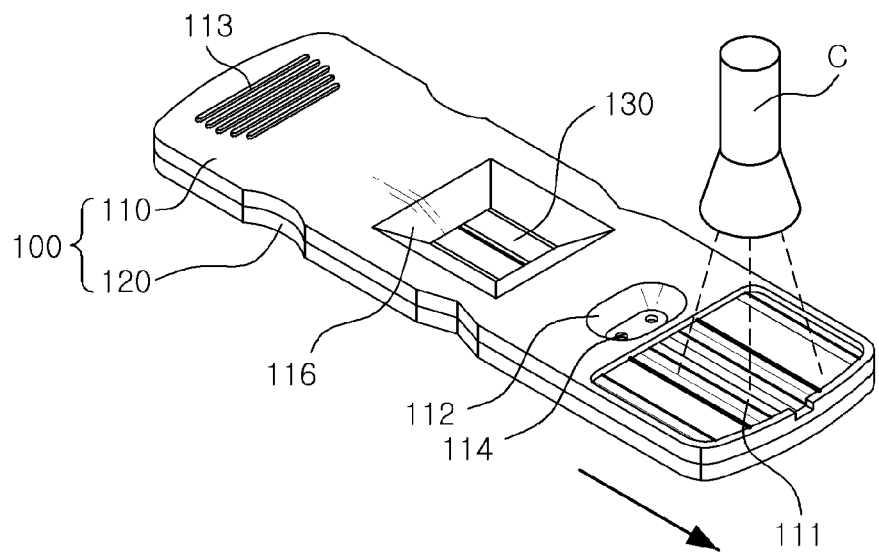
(b)
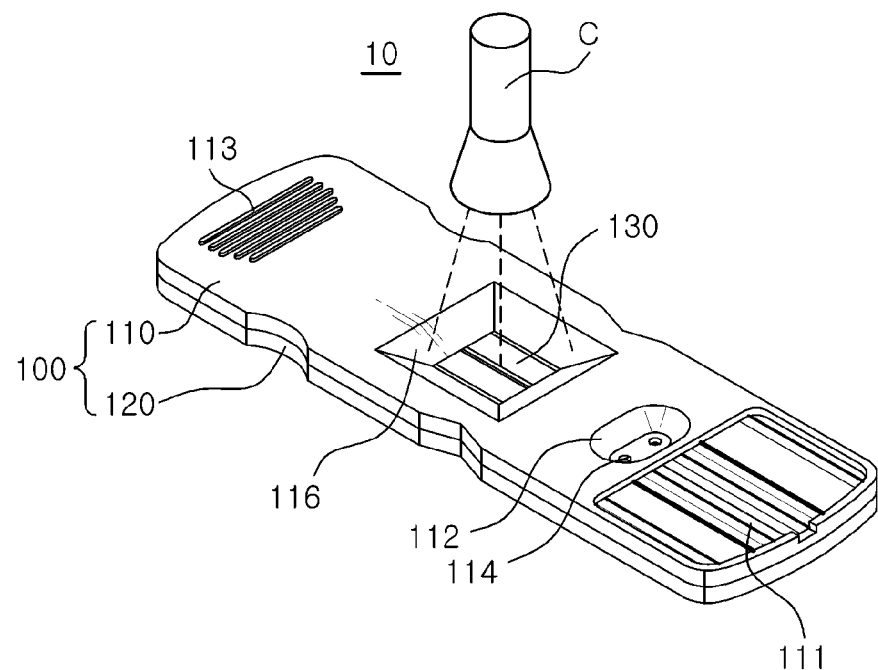

B30

CASE FOR SPECIMEN ANALYZING KIT, KIT FOR SPECIMEN ANALYZING, SPECIMEN ANALYSIS APPARATUS AND CONTROL METHOD OF SPECIMEN ANALYSIS APPARATUS

CROSS-REFERENCE TO RELATED PATENT APPLICATION

This application claims the benefit of Korean Patent Application Nos. 10-2012-0096465, 10-2012-0096466, 10-2012-0096467, 10-2012-0096617, 10-2012-0096468, 10-2012-0096618, 10-2012-0096619 filed on Aug. 31, 2012 and 10-2013-0066450 filed on Jun. 11, 2013, in the Korean Intellectual Property Office, the disclosure of which is incorporated herein in its entirety by reference.

BACKGROUND OF THE INVENTION

1. Field of the Invention

The present invention relates to a case for a specimen analyzing kit, a kit for specimen analyzing, a specimen analysis apparatus, and a control method of the specimen analysis apparatus.

2. Description of the Related Art

As interest in health increases in recent years, technologies for analyzing health conditions by using a bio-sample are being variously introduced.

From among these, a diagnostic kit may be used to analyze the bio-sample, thereby easily checking the health conditions.

In the case where the diagnostic kit is used, to analyze final results, reaction results due to antigen-antibody reaction or enzyme reaction which is generated in the diagnostic kit by the bio-sample should be shown. Here, the results may be photographed by using a camera to analyze the photographed results, thereby obtaining the final results.

The above-described diagnostic kit has a put-in hole in which the bio-sample is put. Also, one characteristic may be generally analyzed by using one diagnostic kit.

However, since multitudinous information are included in a bio-sample such as blood, a method in which separate diagnostic kits for analyzing a large amount of information from the blood are used may have limitations in aspects of costs and efficiency.

Also, the camera for concluding the final results is disposed within one analysis apparatus. Thus, the diagnostic kit on which specimen reaction results to be photographed by the camera are displayed should be inserted into the analysis apparatus.

However, when the diagnostic kit according to the related art is inserted into the analysis apparatus according to the related art, the diagnostic kit is not stably inserted to cause a peel-off phenomenon sometimes. Thus, when the camera photographs the specimen reaction results, serious problems may occur.

That is, the results photographed by the camera involve errors with actual specimen ration results to naturally cause errors in the process of analyzing the photographed results. Thus, it may be difficult to realize accurate analysis.

Thus, in the analysis of health conditions of the human body by using the diagnostic kit, studies for preventing the peel-off phenomenon from occurring to realize accurate analysis are urgently needed so that low costs and efficiency are minimized, and the diagnostic kit is inserted into the analysis apparatus to conclude accurate analysis on the basis of the results photographed by the camera.

Also, to conclude the accurate analysis results with respect to the bio-sample, code information including effective information with respect to each of diagnostic kits should be recognized. In the related art, a method of recognizing code information by using a bar code reader or an RFID unit which is separated from the camera for photographing the reaction results is mainly used.

However, in the case where the existing bar code or RFID unit is used, an additional device for reading a code in addition to the camera for photographing the diagnostic kits should be provided. Thus, it may be difficult to miniaturize the analysis device, and also, additional costs may occur.

Also, since a separate operation for reading the code is required, an analyzing time may be delayed, and the operation may be cumbersome.

Thus, in the analysis of the diagnostic kits, studies considering a plan for improving the code reading for concluding the accurate analysis results and the photographing of the specimen reaction results are required.

SUMMARY OF THE INVENTION

The present invention provides a case for a specimen analyzing kit and a kit for specimen analyzing which analyze multiple characteristics at the same time by putting a specimen once to realize low costs and high efficiency.

The present invention also provides a kit for specimen analyzing and a specimen analysis apparatus which prevent the specimen analyzing kit from peeling off when the specimen analyzing is inserted into a main body to analyze the specimen analyzing kit and stably insert the specimen analyzing kit to improve performance.

The present invention also provides a specimen analysis apparatus in which an identification code and measurement of a specimen reaction result are concluded by using a singular component to realize miniaturization and simplification and also a selectable mode, thereby maximizing user's convenience.

The technical objects of the present invention are not limited to those described above, and it will be apparent to those of ordinary skill in the art from the following description that the present invention includes other technical objects not specifically mentioned herein.

According to an aspect of the present invention, there is provided a specimen analysis apparatus including: an image photographing unit photographing an identification code disposed on a kit for specimen analyzing and a specimen reaction result reacting by injecting a specimen into the kit for specimen analyzing; and a main body on which the image photographing unit is mounted, wherein the image photographing unit photographs the identification code and the specimen reaction result with a time difference.

The image photographing unit may photograph the identification code and the specimen reaction result according to a change in position due to movement of the kit for specimen analyzing.

The specimen analysis apparatus may further include a sensor providing a signal with respect to photographing of the image photographing unit according to a position of the kit for specimen analyzing.

The sensor may include a first sensor and a second sensor which respectively provide signals to allow the image photographing unit to photograph the identification code and the specimen reaction result.

An end of the kit for specimen analyzing may successively contact the first and second sensors to allow the image photographing unit to photograph the identification code and the specimen reaction result.

The image photographing unit may photograph the identification code of the kit for specimen analyzing in which the specimen is not injected.

The specimen analysis apparatus may further include a sensor providing signals with respect to whether the identification code disposed on the kit for specimen analyzing in which the specimen is not injected is photographed and the injection of the specimen into the kit for specimen analyzing in which the specimen is not injected.

The sensor may include a first sensor providing a photographing signal of the image photographing unit with respect to the identification code and a second sensor providing a signal with respect to the injection of the specimen.

The image photographing unit may photograph the specimen reaction result by the specimen when the specimen is completely injected by the signal of the second sensor.

According to another aspect of the present invention, there is provided a specimen analysis apparatus including: a sensor unit detecting a position of a kit for specimen analyzing; an image photographing unit; and a control unit photographs an identification code area of the kit for specimen analyzing through the image photographing unit when a first sensing value is received from the sensor unit, photographs a reaction area of the kit for specimen analyzing through the image photographing unit when a second sensing value is received from the sensor unit, analyzes the identification information of the kit for specimen analyzing on the basis of a photographed image of the identification code area, and analyzes a specimen reaction result on the basis of a photographed image of the reaction area and the identification information.

The control unit may determine whether the identification information is recognized on the basis of the photographed identification code, and when the identification information is not recognized, the control unit may output an error message.

When the identification information is not recognized on the basis of the photographed identification code, the control unit may store the image of the reaction area photographed according to the second sensing value, and when the second sensing value outputted again according to a re-insertion of the kit for specimen analyzing is received, the control unit may analyze the specimen reaction result by using the stored image without performing re-photographing of the reaction area.

According to further another aspect of the present invention, there is provided a specimen analysis apparatus including: a sensor unit detecting a position of a kit for specimen analyzing; an insertion unit in which the kit for specimen analyzing is mounted; an image photographing unit; and a control unit photographs an identification code area of the kit for specimen analyzing through the image photographing unit when a first sensing value is received from the sensor unit, sets a specimen reaction environment on the basis of a recognized result of the identification code, and monitors the specimen reaction result in consideration of the recognized result of the identification code when a specimen is injected into the kit for specimen analyzing that is mounted into the insertion unit.

The control unit may start the setting of the specimen reaction environment as a second sensing value is received from the sensor unit.

The sensor unit may output the first sensor value when the kit for specimen analyzing is disposed at a position at which the image photographing unit is capable of photographing the identification code area.

The specimen reaction environment may include at least one of a specimen reaction temperature and a specimen reaction time.

When the specimen reaction result gets out of a predetermined reference value before the set specimen reaction time passes, the control unit may inform that specimen reaction result gets out of the predetermined reference value.

According to further another aspect of the present invention, there is provided a specimen analysis apparatus including: a sensor unit detecting a position of a kit for specimen analyzing; an image photographing unit; and a control unit receives a sensing value from the sensor unit to allow the image photographing unit to photograph a reaction area in which a specimen injected into a kit for specimen analyzing is introduced and determines whether a specific pattern exists on the basis of a photographed image of the reaction area.

The specific pattern may include a pattern except for a pattern generated by the specimen or a pattern generated by foreign substances introduced into the reaction area.

According to further another aspect of the present invention, there is provided a specimen analysis apparatus including: a sensor unit detecting a position of a kit for specimen analyzing; an image photographing unit; and a control unit selects one of a plurality of modes including first and second modes according to a predetermined reference, photographs at least one of a reaction area of the kit for specimen analyzing and an identification code area of the kit for specimen analyzing through the image photographing unit as a predetermined sensing value is received from the sensor unit, and analyzes a specimen reaction result on the basis of an photographed image of the reaction area and an photographed image of the identification code area according to the selected mode.

BRIEF DESCRIPTION OF THE DRAWINGS

The above and other features and advantages of the present invention will become more apparent by describing in detail exemplary embodiments thereof with reference to the attached drawings in which:

FIG. 1 is a schematic view illustrating a use state of a kit for specimen analyzing including a case for the specimen analyzing kit according to a first embodiment of the present invention;

DETAILED DESCRIPTION OF THE INVENTION

Figure 2:
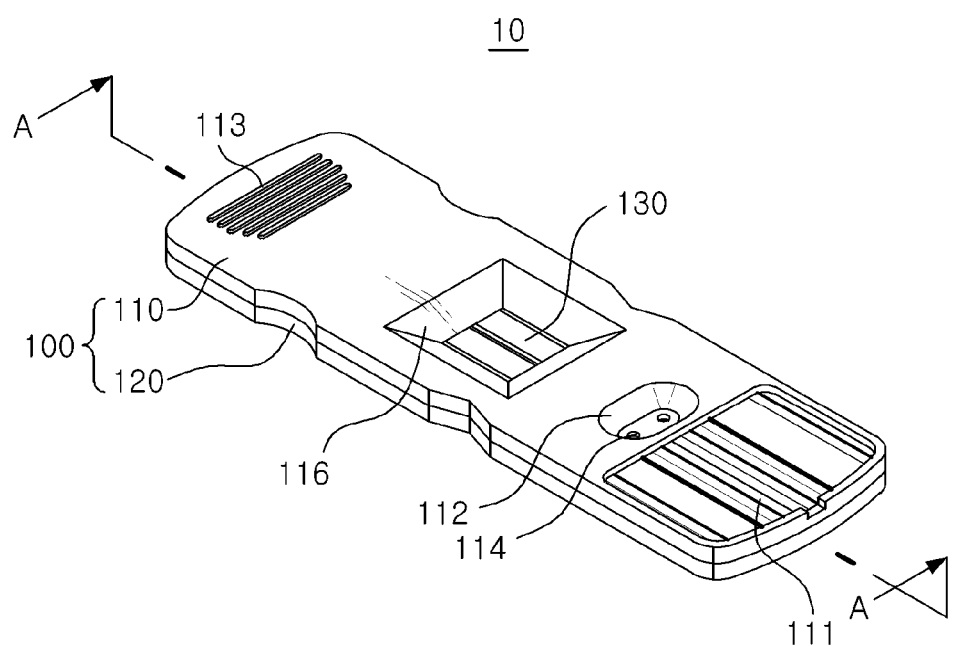
FIG. 2 is a schematic perspective view of the kit for specimen analyzing including the case for the specimen analyzing kit according to the first embodiment of the present invention.

Exemplary embodiments of the present invention will now be described in detail with reference to the accompanying drawings. However, the spirit of the invention is not limited to the embodiment, but retrograde embodiments and other embodiments within the scope of the invention may be easily proposed by adding, changing or deleting any component.

Also, in the drawings, like reference numerals refer to like elements throughout.

First Embodiment

FIG. 1 is a schematic view illustrating a use state of a kit for specimen analyzing including a case for the specimen analyzing kit according to a first embodiment of the present invention, and FIG. 2 is a schematic perspective view of the kit for specimen analyzing including the case for the specimen analyzing kit according to the first embodiment of the present invention.

Figure 3:
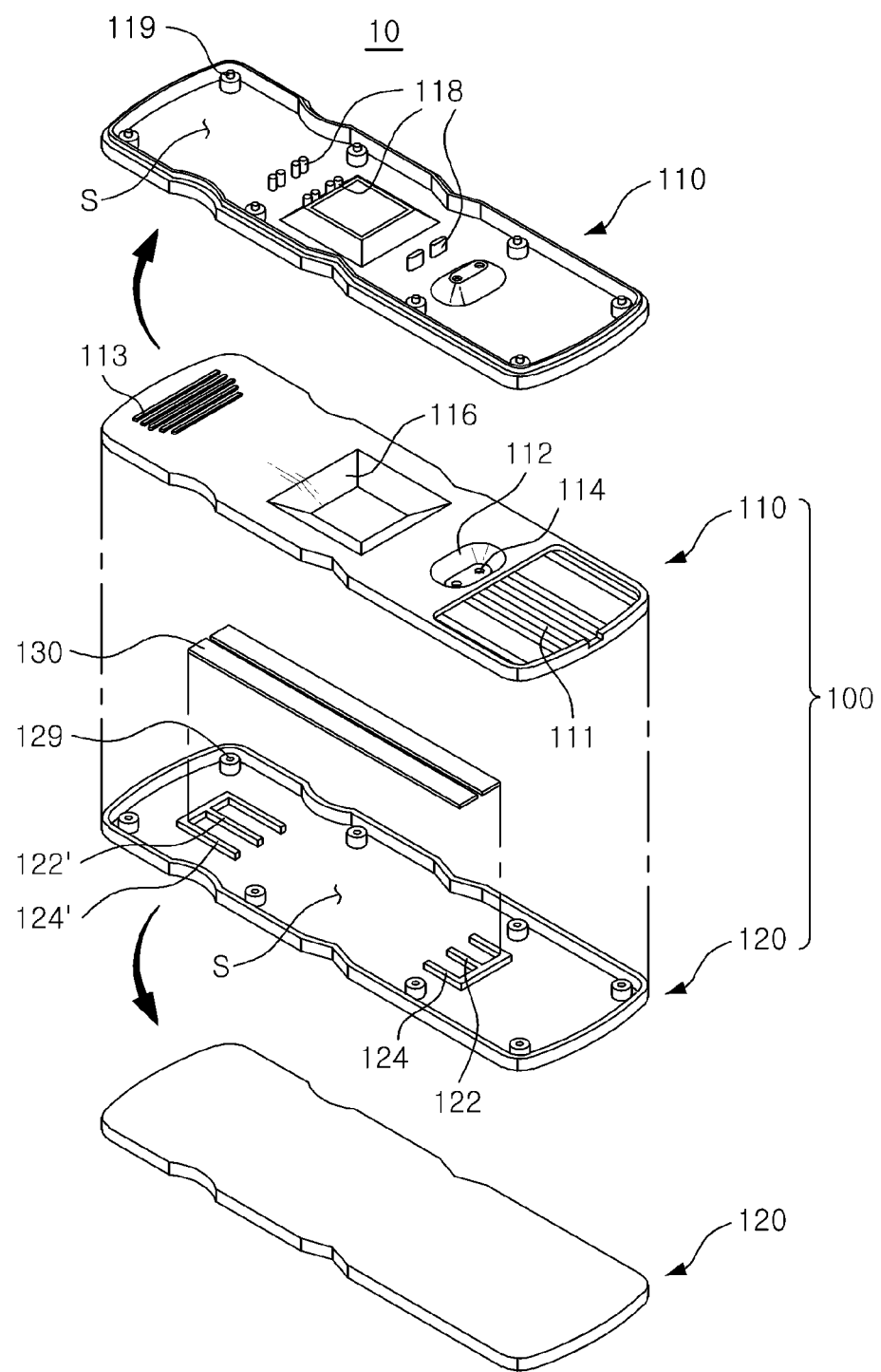
FIG. 3 is a schematic exploded perspective view of the kit for specimen analyzing including the case for the specimen analyzing kit according to the first embodiment of the present invention.
Figure 4:
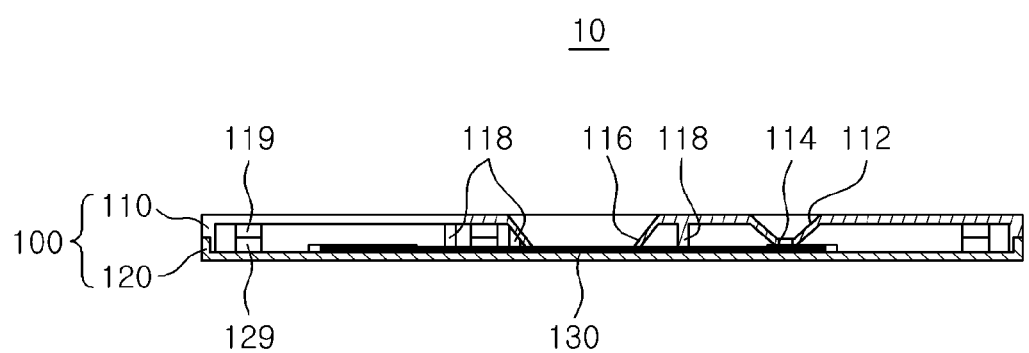
FIG. 4 is a cross-sectional view taken along line A-A of FIG. 2, i.e., a schematic cross-sectional view of the kit for specimen analyzing including the case for the specimen analyzing kit according to the first embodiment of the present invention.

FIG. 3 is a schematic exploded perspective view of the kit for specimen analyzing including the case for the specimen analyzing kit according to the first embodiment of the present invention, and FIG. 4 is a cross-sectional view taken along line A-A of FIG. 2, i.e., a schematic cross-sectional view of the kit for specimen analyzing including the case for the specimen analyzing kit according to the first embodiment of the present invention.

Referring to FIGS. 1 to 4, a kit 10 for specimen analyzing (hereinafter, referred to a "specimen analyzing kit") according to the present invention may include a case 100 for the specimen analyzing kit 10 (hereinafter, referred to as a "case") and a reaction pad 130.

Here, the case 100 may provide a predetermined inner space S. Also, the reaction pad 130 may be disposed in the inner space S.

That is, a specimen collected from blood may move into a reaction area of the reaction pad 130 by a chromatography to react. Here, a result in the reaction area may be defined as a specimen reaction result.

For example, when the specimen collected from the blood moves into the reaction area by the chromatography to react, the reaction area may be changed in color by a flow rate difference due to a concentration of an analysis material contained in the specimen. Here, the changed color in the reaction area may be the specimen reaction result.

Particularly, the specimen may be an antigen, and the specimen reaction result may be an antigen-antibody reaction result.

Here, the antigen may include Myoglobin, Creatine Kinase-MB (CK-MB), Troponin I, Pro-BNP, or D-dimer.

Also, the antigen may be a tumor marker. For example, the tumor marker may include CA15-3 that a metastatic breast cancer marker, CA19-9 that is a rectal cancer and pancreatic cancer marker, CA125 that is an ovarian cancer marker, CEA that is a rectal cancer, lung cancer, pancreatic cancer, gastrointestinal cancer, and breast cancer marker, PSA that is a prostate cancer marker, or AFP that is a liver cancer marker.

However, this is just one example, and thus many specimens may be analyzed, and specimen reaction results thereof may be various.

The specimen analyzing kit 10 according to the present invention may analyze multiple characteristics of the specimen at the same time by putting the specimen once. For this, a plurality of put-in holes 114 may be defined in the case 100.

In detail, the case 100 may include a cover unit 110 and a support unit 120 coupled to the cover unit 110 to define the predetermined inner space S. The cover unit 110 may include a put-in part 112 in which the plurality of put-in holes 114 are defined and a result exposing part 116.

Here, the put-in part 112 may be recessed from a top surface of the cover unit 110 to protrude toward the inner space S. The put-in holes 114 pass through a bottom surface of the put-in part 112.

Thus, when the specimen is put in the put-in part 112, the specimen may be introduced into the inner space S through the plurality of put-in holes 114. Then, the specimen is permeated into the reaction pad 130 disposed under the put-in holes 114 to move into the reaction area of the reaction pad 130 by the chromatography.

As described above, the reaction area of the reaction pad 130 may be an area of which a color is changed by a flow rate difference due to the concentration of the analysis material of the specimen.

Thus, the reaction area of the reaction pad 130 may be exposed to the outside so that a user distinguishes the reaction area, and also the specimen analyzing kit 10 is inserted into the specimen analysis apparatus (see FIG. 17) including a camera C to photograph a specimen reaction result displayed on the reaction area by using the camera C, thereby obtaining the analyzed result of the specimen on the basis of a photographed image. For this, the cover unit 110 may include the result exposing part 116.

The result exposing part 116 may be disposed adjacent to the put-in part 112. Also, the result exposing part 116 may be a kind of hole for exposing all of reaction areas of a plurality of reaction pads 130.

Thus, the result exposing part 116 may have a size greater, somewhat, than those of the reaction areas of the plurality of ration pads 130. As a result, the result exposing part 116 may have a size according to the sizes of the reaction areas of the reaction pads 130.

The reaction pads 130 may correspond to the put-in holes, respectively. The specimens introduced from the put-in holes 114 may be respectively permeated into different reaction pads 130 without interfering with each other.

For example, when the specimen such as blood is put in the put-in part 112, the specimen may pass through the plurality of put-in holes 114 and then be permeated into the plurality of reaction pads 130. Thus, the multiple characteristics of the specimen may be analyzed at the same time by the reaction pads 130.

Here, although two reaction pads 130 and two put-in holes 114 are provided to obtain two specimen reaction results from one specimen in FIGS. 1 to 4, the present invention is not limited thereto. For example, the number of specimen reaction results may be variously changed by changing the number of put-in holes 114 and reaction pads 130 (see FIGS. 5 and 6).

Here, the interference between the specimens introduced from the put-in holes 114 may be prevented by at least one partition wall 122 by which the reaction pads 130 are disposed spaced apart from each other. As a result, the partition wall 122 may partition the inner space S corresponding to the put-in holes 114.

Thus, the specimen analyzing kit 10 according to the present invention may previously prevent the specimens from interfering with each other in the process of analyzing the multiple characteristics of the specimen at the same time to obtain more accurate analysis results.

Particularly, the partition wall 122 for preventing the specimens from interfering with each other may protrude from a bottom surface of the support unit 120 toward the inner space S. Also, the partition wall 122 may be disposed between the plurality of put-in holes 114.

That is, the partition wall 122 may support one side surface of an end of the reaction pad 130 to fix the reaction pad 130 to a position corresponding to that of each of the put-in holes 114. A fixing wall 124 disposed outside the partition wall 122 may support the other side surface of the end of the reaction pad 130.

That is to say, the reaction pads 130 may be disposed spaced apart from each other within the inner space S so that the reaction pads 130 do not interfere with the specimens. For this, the reaction pads 130 should be stably fixed within the inner space S in a state where the reaction pads are spaced apart from each other.

For this, the support unit 120 supports the one surface and the other surface of the end of each of the reaction pads 130 by the partition wall 122 and the fixing wall 124 which protrude from the bottom surface thereof, thereby preventing the above-described interference from occurring.

Here, one side surface and the other side surface of the other end of each of the reaction pads 130 may be supported by a partition corresponding wall 122' and a fixing corresponding wall 124' which respectively correspond to the partition wall 122 and the fixing wall 124. Thus, the reaction pads 130 may be stably fixed within the inner space S.

The reaction pads 130 disposed within the inner space S may receive a pressing force by at least one pressing protrusion 118. The pressing protrusion 118 may protrude from an upper inner surface of the cover unit 110 toward the inner space S.

That is, the pressing protrusion 118 may press one surface of each of the reaction pads 130 disposed between the partition wall 122 and the fixing wall 124 and between the partition corresponding wall 122' and the fixing corresponding wall 124'. Here, the pressed portion may correspond to the outside of the reaction area of each of the reaction pads 130.

Thus, the reaction pads 130 may be more stably fixed within the inner space S by the pressing protrusion 118 pressing a portion outside the reaction area without having an influence on the reaction area in which the specimen reaction result is shown.

The cover unit 110 and the support unit 200 constituting the case 100 may be coupled to each other by at least one coupling part 119 and at least coupling corresponding part 129. The coupling part 119 and the coupling corresponding part 129 may be coupled to each other through a press-fit method.

That is, the coupling part 119 may have a protrusion shape and protrude from an inner top surface of the cover unit 110. Also the coupling corresponding part 129 may have a groove shape and protrude from the bottom surface of the support unit 120.

Thus, the cover unit 110 and the support unit 120 may be coupled to each other by press-fitting the coupling part 119 into the coupling corresponding part 129. Here, the coupling part 119 and the coupling corresponding part 129 may be disposed opposite to each other.

An identification code 111 for obtaining information with respect to a reaction result between the specimen and the reaction pad 130 and a rib 113 may be disposed on one side and the other side of the cover unit 110, respectively.

Here, the identification code 111 may means information including a separate code value required to obtain effective information with respect to the specimen reaction result.

For example, the identification code 111 may be manufacturing lot information of the specimen analyzing kit 10 according to the present invention.

The manufacturing lot information of the specimen analyzing kit 10 may be used to calibrate a result of reading the specimen reaction result.

For another example, the identification code 111 may be an expire data of the specimen analyzing kit 10. The identification code 111 including the expire data may be used to determine whether the specimen analyzing kit 10 is used.

The identification code 111 may be implemented in various forms such as bar codes, color patterns, numerals, and characters. The specimen analyzing kit 10 including the specimen reaction result and the identification code 111 on one surface thereof may be inserted into a measuring device (not shown) including the camera C for photographing to obtain a specimen analysis result on the basis of an image photographed by the camera C.

That is to say, when the specimen analyzing kit 10 according to the present invention is inserted into the measuring device to obtain the specimen analysis result, the identification code 111 is firstly photographed by the camera C in an initial insertion process. Then, when the insertion of the specimen analyzing kit 10 is completed, the camera C photographs the specimen reaction result displayed on the result exposing part 116 (see FIG. 1).

Thereafter, a control unit analyzes a result of reading the specimen reaction result by using the read result of an image of the identification code 111 to output the analyzed result.

Particularly, when the identification code 111 is the manufacturing lot information of the specimen analyzing kit 10, the control unit calibrates a result of reading the specimen reaction result by using the manufacturing lot information read from the identification code 111.

When the identification code 111 is the expire data of the specimen analyzing kit 10, the control unit may output an error message in a case where the expire date passes on the basis of the read result of the identification code 111.

Also, when the identification code 111 represents a kind of specimen to be analyzed in the specimen analyzing kit 10, the control unit may output an error message for informing impossibility of the analysis in a case where a kind of specimen to be analyzed does not correspond to a kind of specimen analyzed by the measuring device according to the read result of the identification code 111.

The rib 113 may be a kind of sliding prevention structure for preventing the specimen analyzing kit 10 from being slid when the specimen analyzing kit 10 is inserted into the measuring device (not shown).

Second Embodiment

Figure 5:
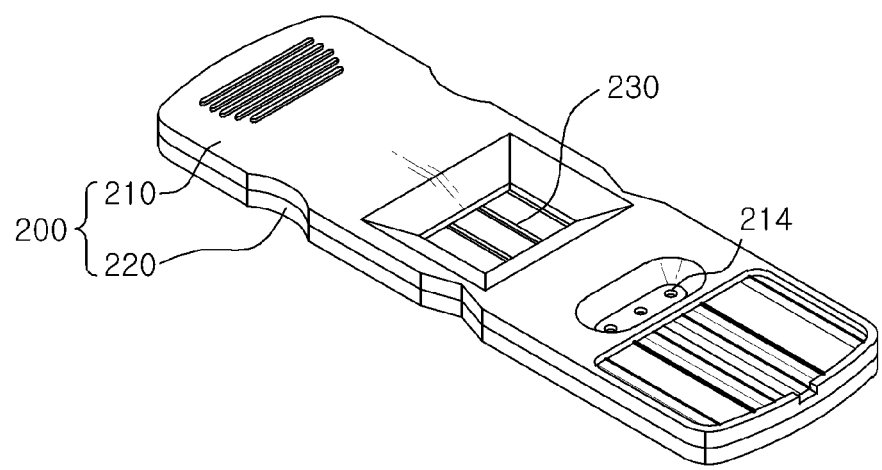
FIG. 5 is a schematic perspective view of a kit for specimen analyzing including a case for the specimen analyzing kit according to a second embodiment of the present invention.
Figure 6:
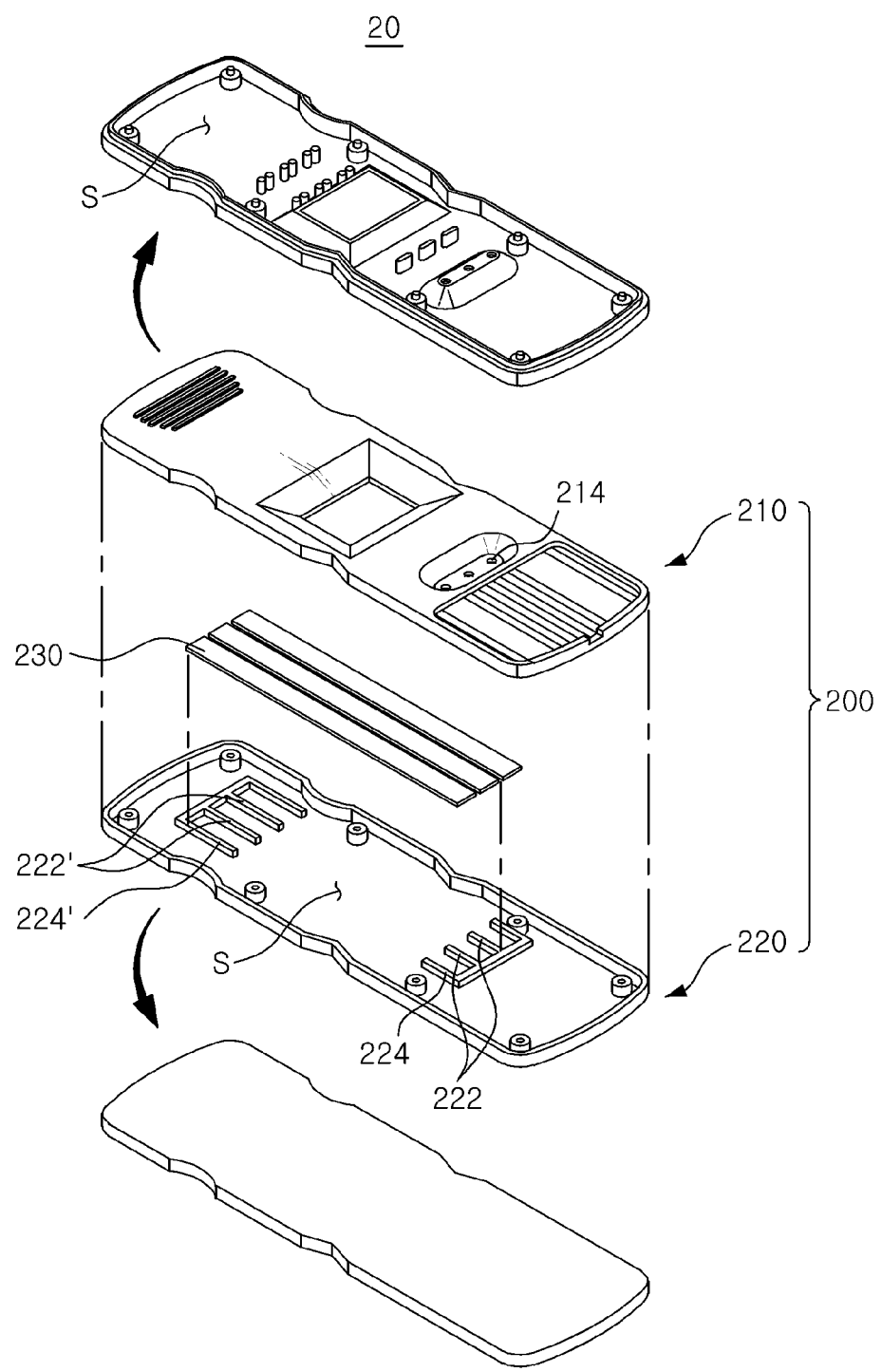
FIG. 6 is a schematic exploded perspective view of the kit for specimen analyzing including the case for the specimen analyzing kit according to the second embodiment of the present invention.

FIG. 5 is a schematic perspective view of a kit for specimen analyzing including a case for the specimen analyzing kit according to a second embodiment of the present invention, and FIG. 6 is a schematic exploded perspective view of the kit for specimen analyzing including the case for the specimen analyzing kit according to the second embodiment of the present invention.

Referring to FIGS. 5 and 6, a specimen analyzing kit 20 including a case for the specimen analyzing kit 20 according to a second embodiment of the present invention is equal to the specimen analyzing kit 10 including the case 100 for the specimen analyzing kit 10 according to the first embodiment of the present invention, which is described with reference to FIGS. 1 to 4, in constitution and effect except for the number of each of a partition wall 222, a fixing wall 224, a partition corresponding wall 222', and a fixing corresponding wall 224'. Thus, descriptions of components except for the partition wall 222, the fixing wall 224, the partition corresponding wall 222', and the fixing corresponding wall 224' will be omitted.

First, as shown in FIGS. 5 and 6, three put-in holes 214 defined in a cover unit 210 of the case 200 and three reaction pads 230 may be provided to obtain three specimen reaction results from one specimen. That is, three characteristics of the specimen may be analyzed at the same time by each of the reaction pads 230.

For this, the three reaction pads 230 may be fixed within an inner space S by the partition wall 222 and the fixing wall 224 which are disposed on a support unit 220. The middle reaction pad 230 may be fixed by using only the partition wall 222.

That is, the outer reaction pads 230 may be supported by the partition wall 222 and the fixing wall 224 which respectively support one surface and the other surface of an end of each of the reaction pads 230. Also, one surface and the other surface of the middle reaction pad 230 may be supported by the two partition walls 222.

The other end of each of the reaction pads 230 may be supported by the partition corresponding wall 222' and the fixing corresponding wall 224' which respectively correspond to the partition wall 222 and the fixing wall 224. Thus, the reaction pads 230 may be stably fixed within the inner space S.

As a result, the partition wall 222, the fixing wall 224, the partition corresponding wall 222' and the fixing corresponding wall 224' may be variously changed according to the number of each of the put-in holes 214 and the reaction pads 230.

That is, three put-in holes 214 and three reaction pads 230 may be provided. As a result, the partition wall 222, the fixing wall 224, the partition corresponding wall 222', and the fixing corresponding wall 224' may be changed in number.

Third Embodiment

Figure 7:
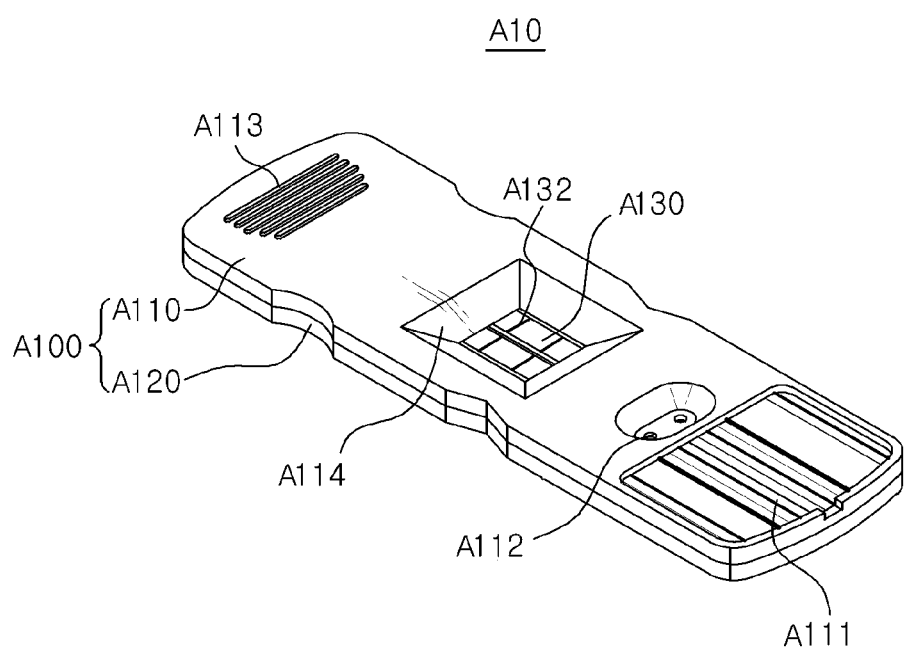
FIG. 7 is a schematic perspective view of a kit for specimen analyzing according to a third embodiment of the present invention.
Figure 8:
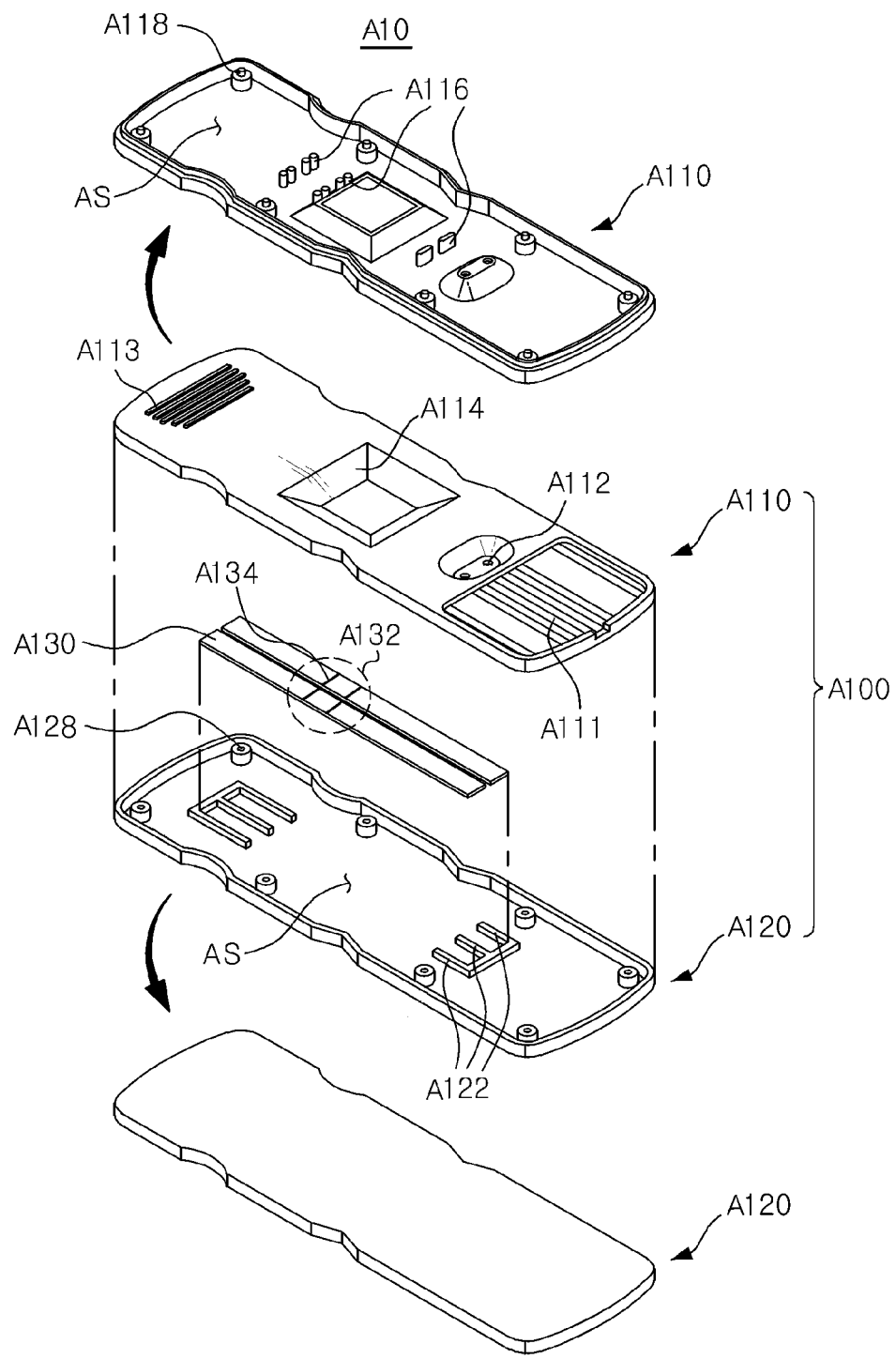
FIG. 8 is a schematic exploded perspective view of the kit for specimen analyzing according to the third embodiment of the present invention.
Figure 9:
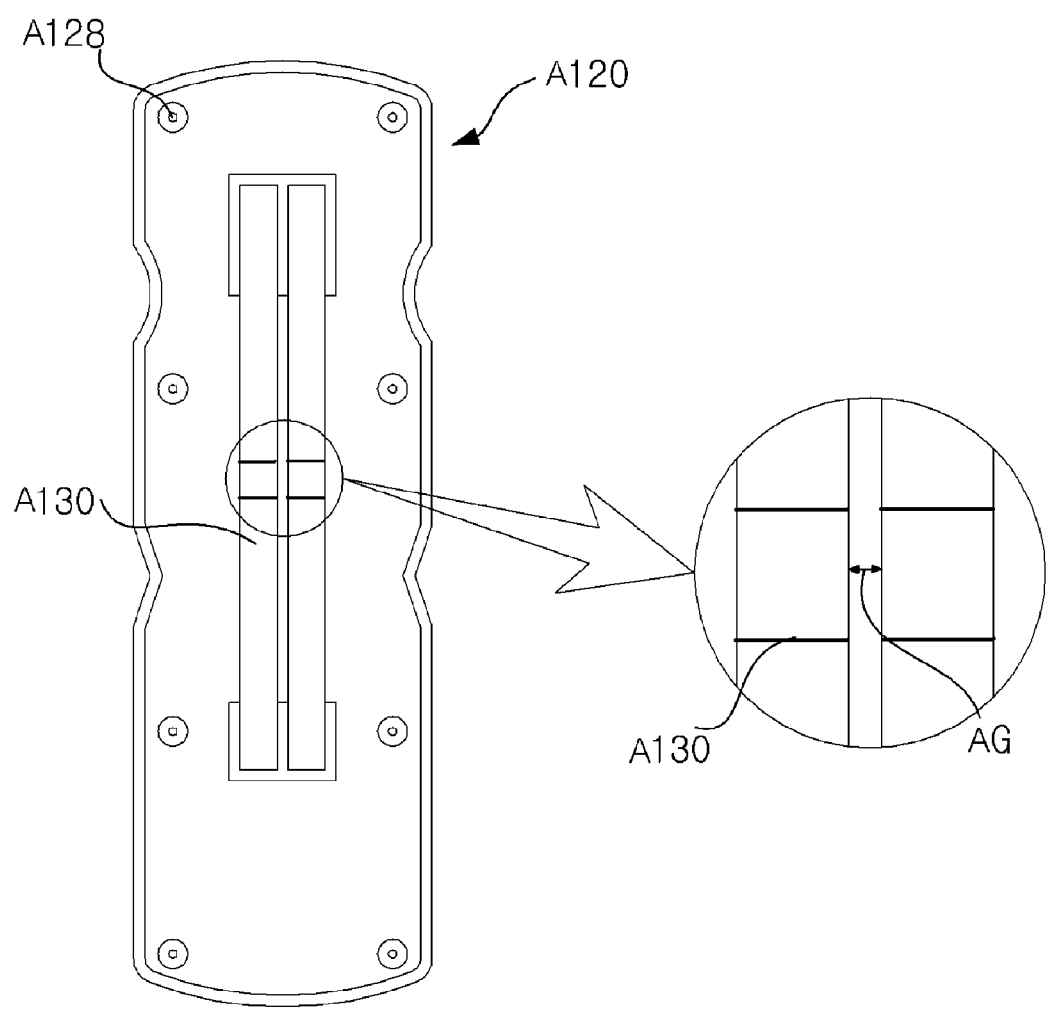
FIG. 9 is a schematic plan view of a support unit provided in the kit for specimen analyzing according to the third embodiment of the present invention.

FIG. 7 is a schematic perspective view of a kit for specimen analyzing according to a third embodiment of the present invention, FIG. 8 is a schematic exploded perspective view of the kit for specimen analyzing according to the third embodiment of the present invention, and FIG. 9 is a schematic plan view of a support unit provided in the kit for specimen analyzing according to the third embodiment of the present invention.

Referring to FIGS. 7 to 9, a specimen analyzing kit A10 according to the present invention may include a case A100 providing a predetermined inner space AS and at least two reaction pads A130 disposed within the inner space AS.

Particularly, the case A100 may include a cover unit A110 and a support unit A120 coupled to the cover unit A110 to define the predetermined inner space AS. The at least two reaction pads A130 may be disposed in the inner space AS so that multiple characteristics of a specimen are analyzed at the same time by putting the specimen once.

Here, put-in holes A112 communicating with the outside to correspond to the reaction pads A130 may be defined in the case A100, i.e., the cover unit A110 so that the specimen is permeated into the at least two reaction pads A130.

That is to say, the number of put-in holes A112 may be equal to that of reaction pads A130 disposed in the inner space AS. When the specimen is injected into the put-in holes A112, the specimen may be introduced into the inner space AS through the put-in holes A112.

The specimen introduced into the inner space AS through the put-in holes A112 may be permeated into the at least two reaction pads A130 disposed under the put-in holes A112 to move into reaction areas A132 of the reaction pads A130 by a chromatography.

That is, when a predetermined time passes, the specimen collected from blood may move into the reaction areas A132 of the reaction pads A130 by the chromatography to react. Hereinafter, a result of each of the reaction areas A132 may be defined as a specimen reaction result A134.

That is, when the specimen collected from the blood is injected into the put-in holes A112 of the specimen analyzing kit A10, the specimen moves into the reaction areas A132 of the reaction pads 130 after a predetermined time passes to react. Thus, a result of each of the reaction areas A132 may be defined as a specimen reaction result A134.

This represents a change in the reaction areas A132 by a flow rate difference due to a concentration of an analysis material contained in the specimen on the reaction pads A130. That is, the changed color in the reaction areas A132 may be the specimen reaction result A134.

Particularly, the specimen may be an antigen, and the specimen reaction result may be an antigen-antibody reaction result.

Here, the antibody may include Myoglobin, Creatine Kinase-MB (CK-MB), Troponin I, Pro-BNP, or D-dimer.

Also, the antigen may be a tumor marker. For example, the tumor marker may include CA15-3 that a metastatic breast cancer marker, CA19-9 that is a rectal cancer and pancreatic cancer marker, CA125 that is an ovarian cancer marker, CEA that is a rectal cancer, lung cancer, pancreatic cancer, gastrointestinal cancer, and breast cancer marker, PSA that is a prostate cancer marker, or AFP that is a liver cancer marker.

However, this is just one example, and thus many specimens may be analyzed, and specimen reaction results thereof may be various.

The specimen reaction result A134 may be implemented in at least one band shape. Thus, the band shape may be analyzed to analyze health conditions of a subject from which the specimen is collected.

Thus, it may be necessary to expose the reaction areas A132 of the reaction pads A130 to the outside so that the subject distinguishes the reaction areas A132. For this, the specimen analyzing kit A10 may include a result exposing part A114.

Particularly, the result exposing part A114 may be disposed adjacent to the put-in holes A112. Also, the result exposing part A114 may be a kind of hole for exposing all of reaction areas A132 of the at least two reaction pads A130.

Thus, the result exposing part A114 may have a size greater, somewhat, than those of the reaction areas A132 of the at least two ration pads A130. As a result, the result exposing part A114 may have a size according to the sizes of the reaction areas A132 of the reaction pads A130.

As described above, the reaction pads A130 may correspond to the put-in holes A112, respectively. The specimen introduced from the put-in holes A112 may be permeated into different reaction pads A130 without interfering with each other.

For example, when the specimen such as blood is put in the put-in holes A112, the specimen may pass through the at least two put-in holes A112 and then be permeated into the reaction pads A130. Thus, the multiple characteristics of the specimen may be analyzed at the same time from a reaction result in each of the reaction areas A132 of the reaction pads A130.

Here, although the two reaction pads A130 and the two put-in holes A112 are provided to obtain two specimen reaction results from one specimen in FIGS. 7 to 9, the present invention is not limited thereto. For example, the number of specimen reaction results may be variously changed by changing the number of put-in holes A112 and reaction pads A130 (see FIGS. 10 and 11).

It may be necessary to prevent the specimens introduced from the put-in holes A112 and permeated into each of the reaction pads A130 from leaking, thereby preventing the specimens from interfering with each other so as to realize an accurate specimen reaction result.

As a result, a leakage prevention gap AG may represent a spaced distance between the reaction pads A130 for prevent the specimen from leaking.

Here, the leakage prevention gap AG may be a distance of about 0.5 mm or more. Results obtained through experiments with respect to conditions for preventing the leakage are as follows in Tables 1 to 5.

TABLE 1

| | | Width of reaction pad (mm) 3.8 Volume of specimen (μl) | | | | |
|---|---|---|---|---|---|---|
| | | 220 | 230 | 240 | 250 | 260 |
| Leakage prevention gap (mm) 누수방지갭 (mm) | 0.1 | O | O | O | O | O |
| | 0.2 | O | O | O | O | O |
| | 0.3 | O | O | O | O | O |
| | 0.4 | O | O | O | O | O |
| | 0.5 | X | X | X | O | O |
| | 0.6 | X | X | X | O | O |
| | 0.7 | X | X | X | X | O |
| | 0.8 | X | X | X | X | O |
| | 0.9 | X | X | X | X | O |
| | 1.0 | X | X | X | X | O |

TABLE 2

| | | Width of reaction pad (mm) 3.9 Volume of specimen (μl) | | | | |
|---|---|---|---|---|---|---|
| | | 220 | 230 | 240 | 250 | 260 |
| Leakage prevention gap (mm) 누수방지갭 (mm) | 0.1 | O | O | O | O | O |
| | 0.2 | O | O | O | O | O |
| | 0.3 | O | O | O | O | O |
| | 0.4 | O | O | O | O | O |
| | 0.5 | X | X | O | O | O |
| | 0.6 | X | X | X | X | O |
| | 0.7 | X | X | X | X | O |
| | 0.8 | X | X | X | X | O |
| | 0.9 | X | X | X | X | X |
| | 1.0 | X | X | X | X | X |

TABLE 3

| | | Width of reaction pad (mm) 4 Volume of specimen (μl) | | | | |
|---|---|---|---|---|---|---|
| | | 220 | 230 | 240 | 250 | 260 |
| Leakage prevention gap (mm) 누수방지갭 (mm) | 0.1 | O | O | O | O | O |
| | 0.2 | O | O | O | O | O |
| | 0.3 | O | O | O | O | O |
| | 0.4 | O | O | O | O | O |
| | 0.5 | X | X | X | X | O |
| | 0.6 | X | X | X | X | X |
| | 0.7 | X | X | X | X | X |
| | 0.8 | X | X | X | X | X |
| | 0.9 | X | X | X | X | X |
| | 1.0 | X | X | X | X | X |

TABLE 4

| | | Width of reaction pad (mm) 4.1 Volume of specimen (μl) | | | | |
|---|---|---|---|---|---|---|
| | | 220 | 230 | 240 | 250 | 260 |
| Leakage prevention gap (mm) 누수방지갭 (mm) | 0.1 | O | O | O | O | O |
| | 0.2 | O | O | O | O | O |
| | 0.3 | O | O | O | O | O |
| | 0.4 | O | O | O | O | O |
| | 0.5 | X | X | X | O | O |
| | 0.6 | X | X | X | X | O |
| | 0.7 | X | X | X | X | X |
| | 0.8 | X | X | X | X | X |
| | 0.9 | X | X | X | X | X |
| | 1.0 | X | X | X | X | X |

TABLE 5

| | | Width of reaction pad (mm) 4.2 Volume of specimen (μl) | | | | |
|---|---|---|---|---|---|---|
| | | 220 | 230 | 240 | 250 | 260 |
| Leakage prevention gap (mm) 누수방지갭 (mm) | 0.1 | O | O | O | O | O |
| | 0.2 | O | O | O | O | O |
| | 0.3 | O | O | O | O | O |
| | 0.4 | O | O | O | O | O |
| | 0.5 | X | X | O | O | O |
| | 0.6 | X | X | X | X | X |
| | 0.7 | X | X | X | X | X |
| | 0.8 | X | X | X | X | X |
| | 0.9 | X | X | X | X | X |
| | 1.0 | X | X | X | X | X |

Tables 1 to 5 show results which are obtained by measuring whether interference of the specimen due to the leakage occurs while changing a width of each of the reaction pads A130, a volume of the injected specimen, and the leakage prevention gap AG. Here, the experiments may be repeatedly performed one hundred times. As a result, if the leakage does not occur ninety-five times or more, a reference symbol "O" is displayed. On the other hand, if the leakage occurs ninety-five times or less, a reference symbol "X" is displayed.

The width of each of the reaction pads A130 may be limited in a range enough to be disposed in the inner space AS of the case A100 in consideration of the whole size of the case A100.

Referring to Tables 1 to 5, when the specimen injected into the at least two reaction pads A130 has a total volume in an error range of about ±20 μl on the basis of about 240 μl, and each of the at least two reaction pads A130 has a width in an error range of about ±2.0 mm on the basis of about 4.0 mm, it is seen that the leakage prevention gap has a distance of about 0.5 mm or more so as to prevent the leakage and interference when the multiple characteristics of the specimen are measured.

Particularly, it is preferable that the leakage prevention gap AG has a distance of about 0.7 mm or more under the above-described conditions to maximize efficiency in leakage prevention when the multiple characteristics of the specimen are measured.

When the specimen injected into the at least two reaction pads A130 has a total volume ranging from about 220 μl to about 240 μl, each of the at least two reaction pads A130 may have a width ranging from about 3.8 mm to about 3.9 mm.

Also, when the specimen injected into the at least two reaction pads A130 has a total volume ranging from about 220 μl to about 250 μl, each of the at least two reaction pads A130 may have a width ranging from about 4.0 mm to about 4.2 mm.

Also, when the specimen injected into the at least two reaction pads A130 has a total volume of about 260, each of the at least two reaction pads A130 may have a width ranging from about 4.0 mm to about 4.2 mm, and the leakage prevention gap AG may have a distance of about 0.6 mm or more.

The case A100 may include a fixing wall A122 for fixing the reaction pads A130 to dispose the at least two reaction pads A130 within the inner space AS while maintaining the leakage prevention gap AG satisfying the above-described conditions.

Particularly, the fixing wall A122 may protrude from a bottom surface of the support unit A120 toward the inner space AS. Also, the fixing wall A122 may be dislocated with respect to the put-in holes A112 around the put-in holes A112.

That is, the fixing wall A122 supports one end and the other end of each of the reaction pads A130 to fix the reaction pads A130 to positions corresponding to those of the put-in holes A112 in a state where the fixing wall A122 surrounds the one end and the other end of each of the reaction pads A130, thereby stably maintaining the leakage prevention gap AG for preventing the leakage.

Thus, according to the specimen analyzing kit A10 of the present invention, the specimen may be put in once to analyze the multiple characteristics of the specimen at the same time. Also, the leakage and interference of the specimen when the multiple characteristics of the specimen are analyzed at the same time may be previously prevented to obtain more accurate analysis results.

However, the present invention is not limited to the fixing wall A122 spaced apart from portions of the support unit A120 corresponding to the one end and the other end of each of the reaction pads A130. For example, the fixing wall A122 may be continuously disposed from the one end of each of the reaction pads A130 toward the other end of each of the reaction pads A130.

The reaction pads A130 disposed within the inner space AS may receive a pressing force by at least one pressing protrusion A116. The pressing protrusion A116 may protrude from an upper inner surface of the cover unit A110 toward the inner space AS.

That is, the pressing protrusion A116 may press one surface of each of the reaction pads A130 disposed correspondingly between the fixing walls A122. Here, the pressed portion may correspond to the outside of the reaction area A132 of each of the reaction pads A130.

Thus, the reaction pads A130 may be more stably fixed within the inner space AS by the pressing protrusion A118 pressing a portion outside the reaction areas A130 without having an influence on the reaction areas A132 in which the specimen reaction result is shown.

The cover unit A110 and the support unit A100 constituting the case A100 may be coupled to each other by at least one coupling part A118 and at least coupling corresponding part A128. The coupling part A118 and the coupling corresponding part A128 may be coupled to each other through a press-fit method.

That is, the coupling part A118 may have a protrusion shape and protrude from an inner top surface of the cover unit A110. Also the coupling corresponding part A128 may have a groove shape and protrude from the bottom surface of the support unit A120.

Thus, the cover unit A110 and the support unit A120 may be coupled to each other by press-fitting the coupling part A118 into the coupling corresponding part A128. Here, the coupling part A118 and the coupling corresponding part A128 may be disposed opposite to each other.

An identification code A111 for obtaining information with respect to a reaction result between the specimen and the reaction pads A130 and a rib A113 may be disposed on one side and the other side of the cover unit A110, respectively.

Here, the identification code A111 may means information including a separate code value required to obtain effective information about the specimen reaction result.

For example, the identification code A111 may be manufacturing lot information with respect to the specimen analyzing kit A10 according to the present invention.

The manufacturing lot information of the specimen analyzing kit A10 may be used to calibrate a result of reading the specimen reaction result.

For another example, the identification code A111 may be an expire data of the specimen analyzing kit A10. The identification code A111 including the expire data may be used to determine whether the specimen analyzing kit A10 is used.

The identification code A111 may be implemented in various forms such as bar codes, color patterns, numerals, and characters. The specimen analyzing kit A10 including the specimen reaction result and the identification code A111 on one surface thereof may be inserted into a measuring device (not shown) including the camera for photographing to obtain a specimen analyzing result on the basis of an image photographed by the camera.

That is to say, when the specimen analyzing kit A10 according to the present invention is inserted into the measuring device to obtain the specimen analysis result, the identification code A111 is firstly photographed by the camera in an initial insertion process. Then, when the insertion of the specimen analyzing kit A10 is completed, the camera photographs the specimen reaction result displayed on the result exposing part A114.

Thereafter, a control unit analyzes a result of reading the specimen reaction result by using the reading result of an image of the identification code A111 to output the analyzed result.

Particularly, when the identification code A111 is the manufacturing lot information of the specimen analyzing kit A10, the control unit calibrates a result of reading the specimen reaction result by using the manufacturing lot information read from the identification code A111.

When the identification code A111 is the expire data of the specimen analyzing kit A10, the control unit may output an error message in a case where the expire date passes on the basis of the read result of the identification code A111.

Also, when the identification code A111 represents a kind of specimen to be analyzed in the specimen analyzing kit A10, the control unit may output an error message for informing impossibility of the analysis in a case where a kind of specimen to be analyzed does not correspond to a kind of specimen analyzed by the measuring device according to the read result of the identification code A111.

The rib A113 may be a kind of sliding prevention structure for preventing the specimen analyzing kit A10 from being slid when the specimen analyzing kit A10 is inserted into the measuring device (not shown).

Fourth Embodiment

Figure 10:
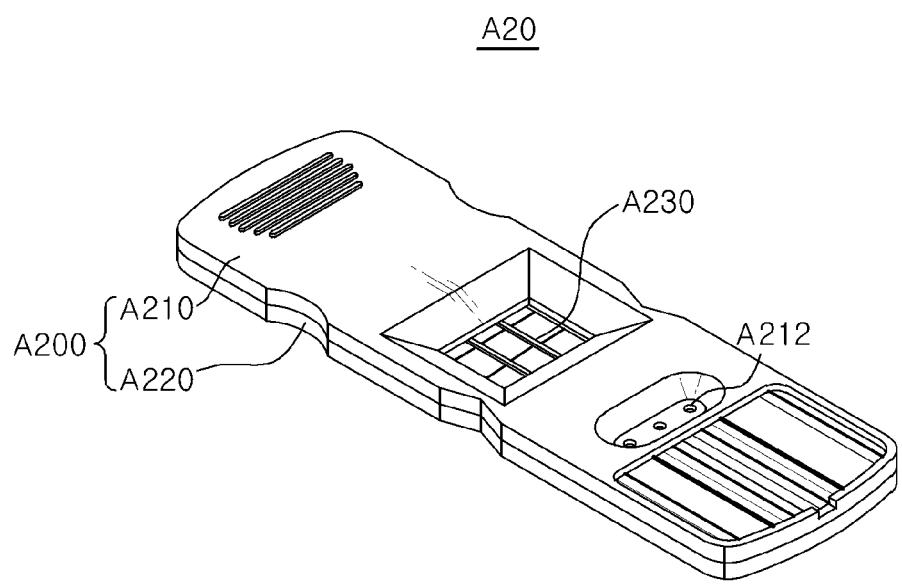
FIG. 10 is a schematic perspective view of a kit for specimen analyzing according to a fourth embodiment of the present invention.
Figure 11:
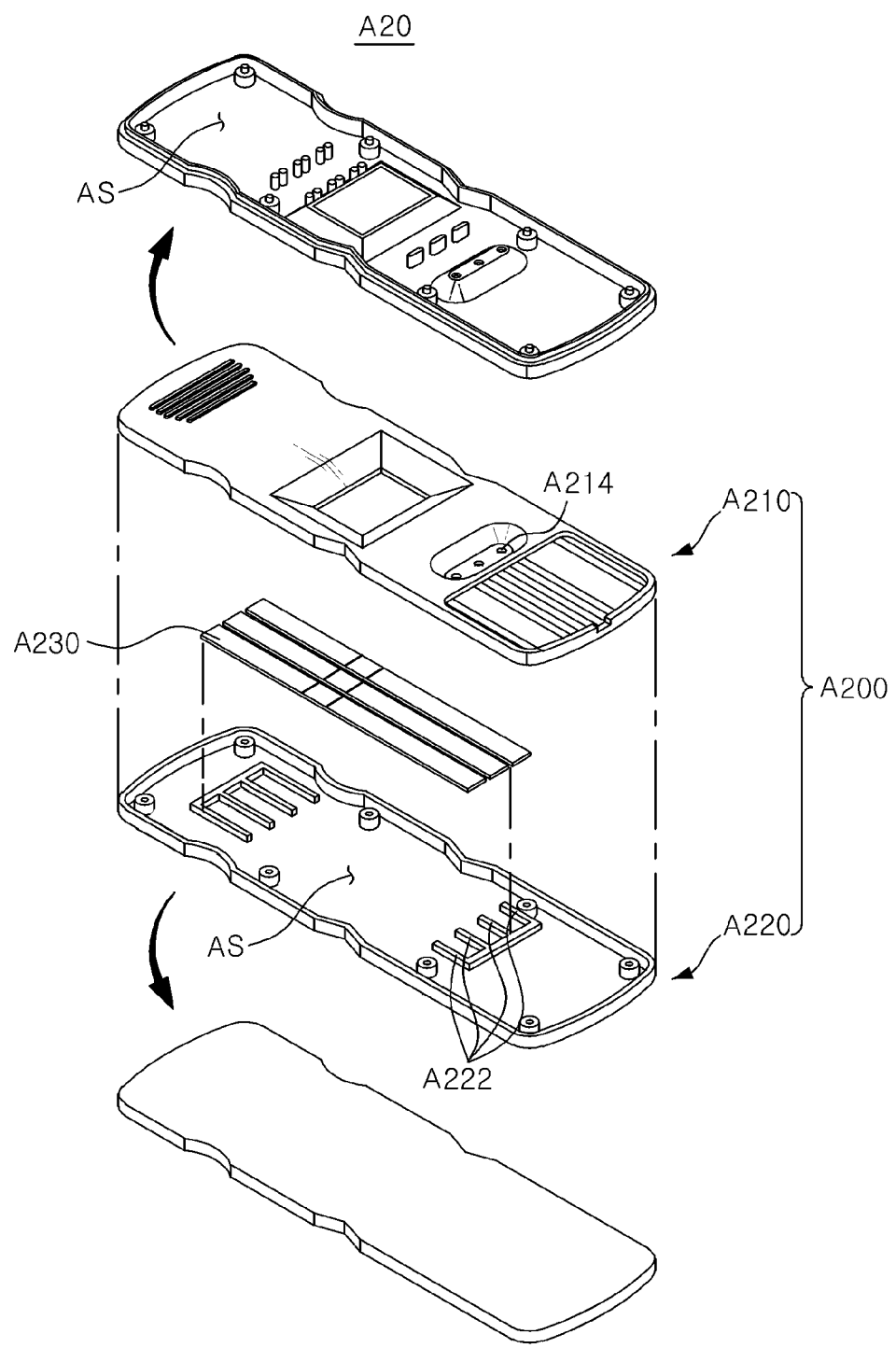
FIG. 11 is a schematic exploded perspective view of the kit for specimen analyzing according to the fourth embodiment of the present invention.
Figure 12:
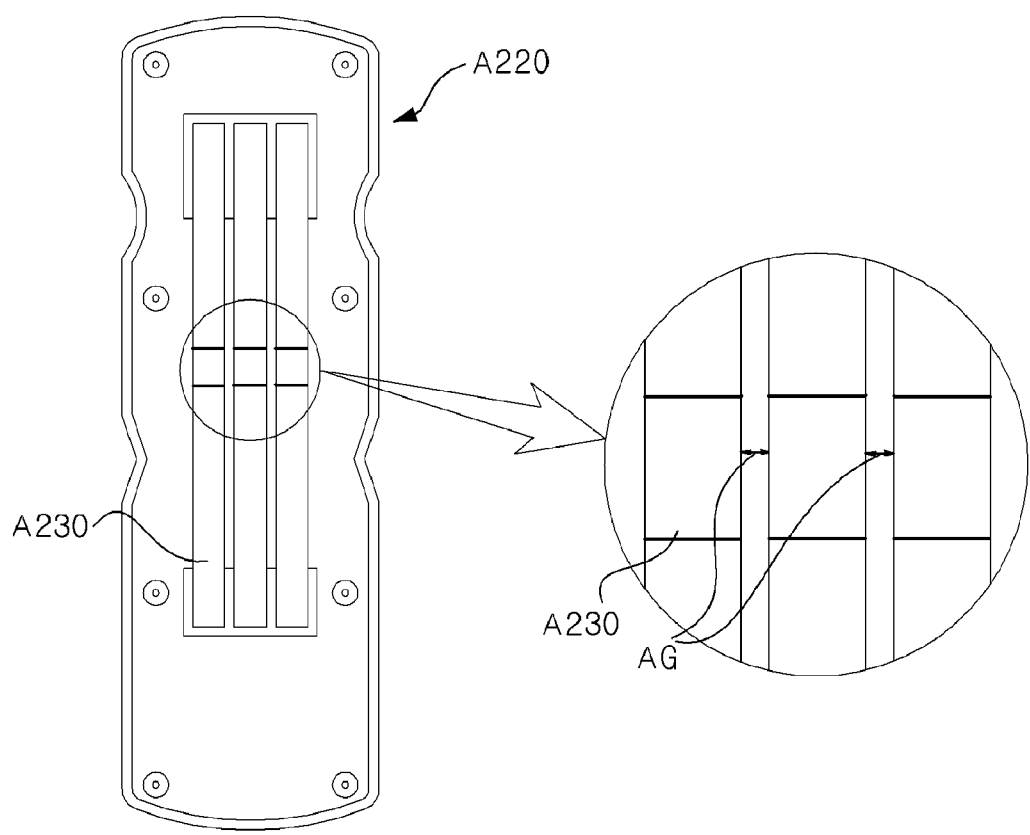
FIG. 12 is a schematic plan view of a support unit provided in the kit for specimen analyzing according to the fourth embodiment of the present invention.

FIG. 10 is a schematic perspective view of a kit for specimen analyzing according to a fourth embodiment of the present invention, FIG. 11 is a schematic exploded perspective view of the kit for specimen analyzing according to the fourth embodiment of the present invention, and FIG. 12 is a schematic plan view of a support unit provided in the kit for specimen analyzing according to the fourth embodiment of the present invention.

Referring to FIGS. 10 to 12, a specimen analyzing kit A20 according to a fourth embodiment of the present invention is equal to the specimen analyzing kit A10 according to the third embodiment of the present invention, which is described with reference to FIGS. 7 to 9, in constitution and effect except for the number of each of a put-in hole A212, a reaction pad A230, and a fixing wall A222. Thus, descriptions of components except for the put-in hole A212, the reaction pad A230, and the fixing wall A222 will be omitted.

The specimen analyzing kit A20 may include three put-in holes A212 defined in a cover unit A210 of a case A200 and three reaction pads A230 to obtain three specimen reaction results from one specimen. That is, three characteristics of the specimen may be analyzed at the same time by each of the reaction pads A230.

For this, the three reaction pads A230 may be fixed within the inner space AS by the plurality of fixing walls A222 disposed on the support unit A220.

As a result, the number of fixing walls A222 may be variously changed according to the number of each of the put-in holes A212 and the reaction pads A230.

That is, three put-in holes A222 and three reaction pads 230 may be provided. As a result, the fixing walls A222 may be changed in number.

Also, as described above, it is seen that the reaction pads A230 are stably fixed in the state where the reaction pads A230 are fixed with a leakage prevention gap AG within the inner space AS by the fixing walls A222.

Fifth Embodiment

Figure 13:
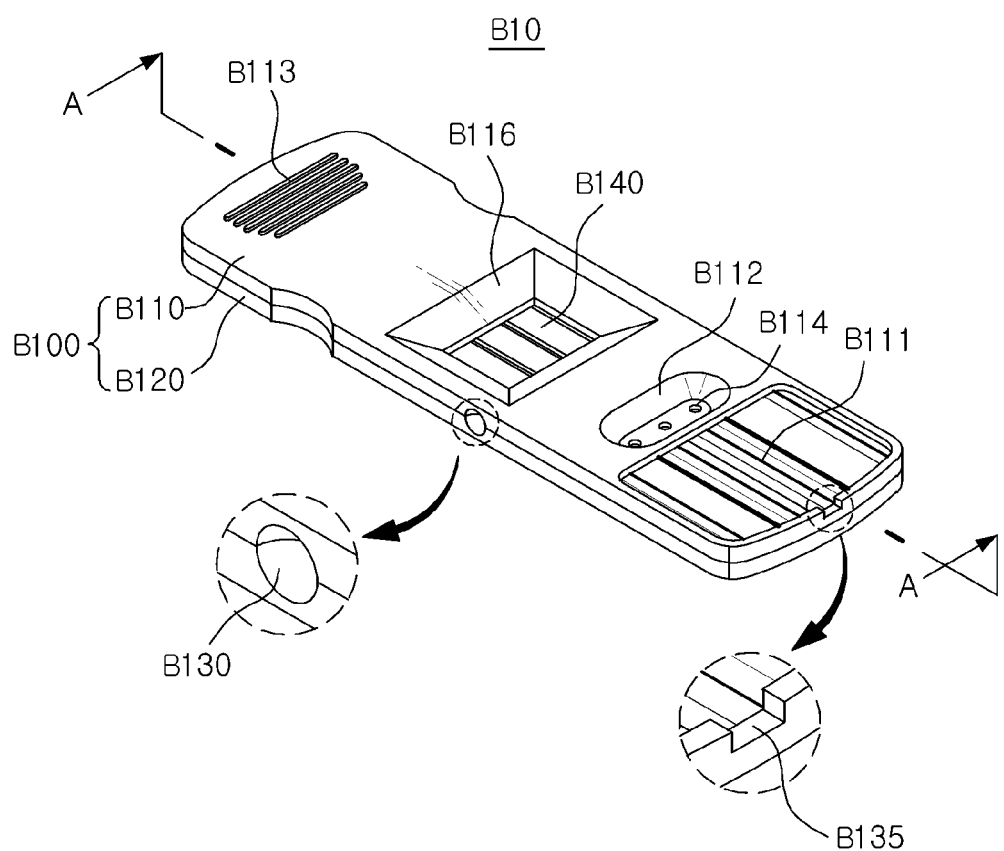
FIG. 13 is a schematic perspective view of a kit for specimen analyzing according to a fifth embodiment of the present invention.
Figure 14:
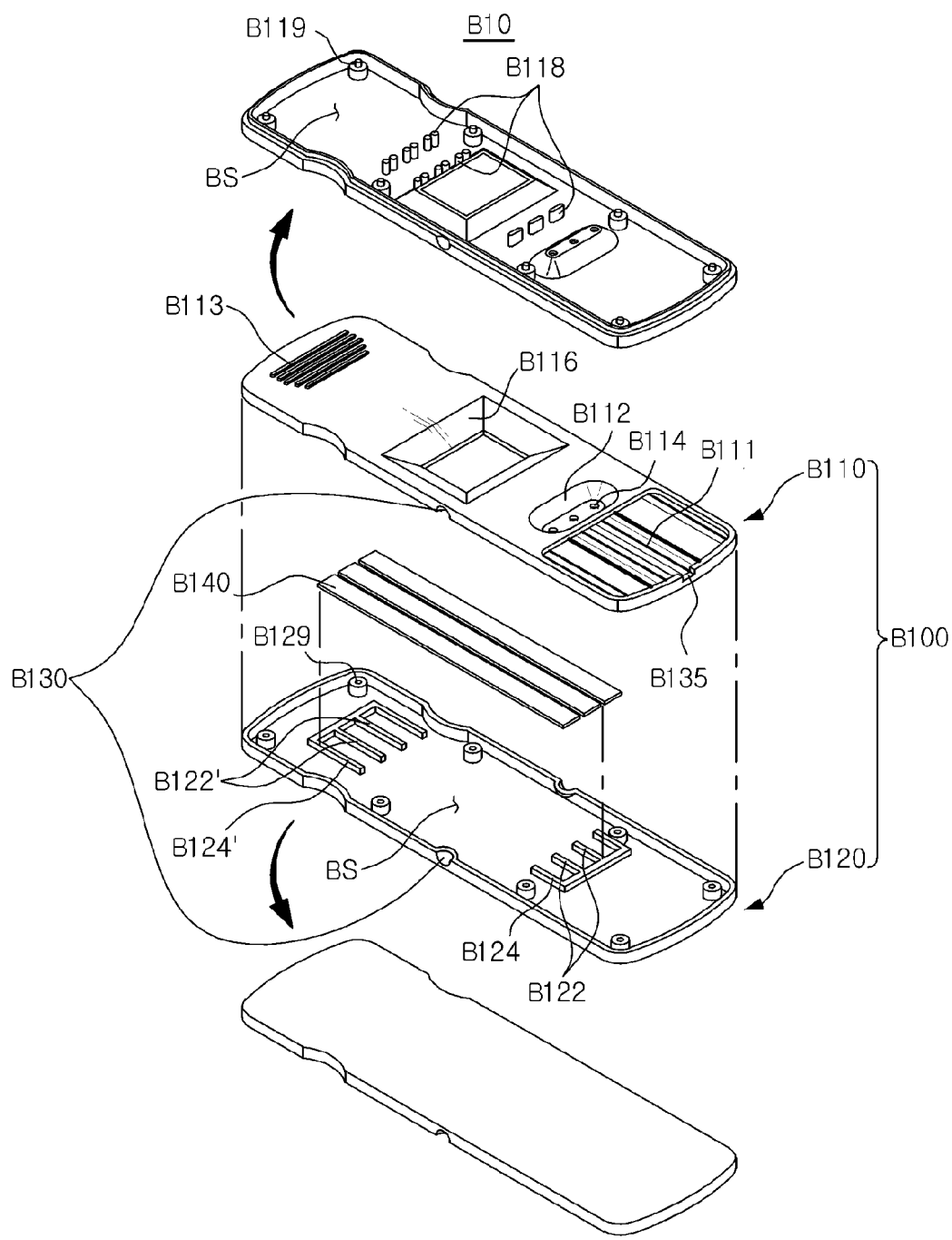
FIG. 14 is a schematic exploded perspective view of the kit for specimen analyzing according to the fifth embodiment of the present invention.
Figure 15:
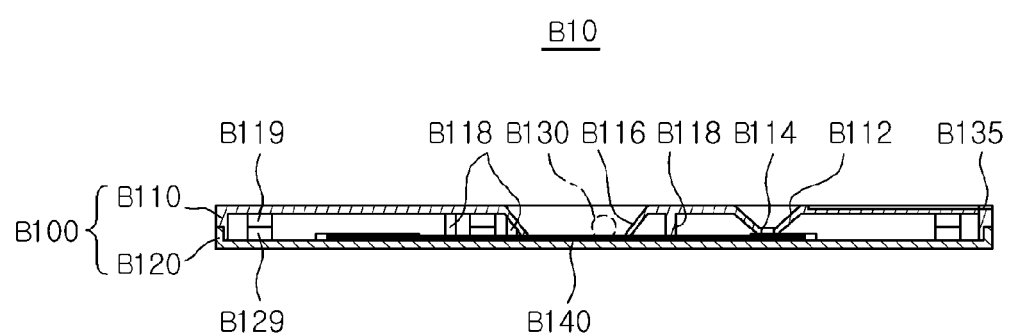
FIG. 15 is a cross-sectional view taken along line A-A of FIG. 1, i.e., a schematic cross-sectional view of the kit for specimen analyzing including a case for the specimen analyzing kit according to the fifth embodiment of the present invention.

FIG. 13 is a schematic perspective view of a kit for specimen analyzing according to a fifth embodiment of the present invention, FIG. 14 is a schematic exploded perspective view of the kit for specimen analyzing according to the fifth embodiment of the present invention, and FIG. 15 is a cross-sectional view taken along line A-A of FIG. 1, i.e., a schematic cross-sectional view of the kit for specimen analyzing including a case for the specimen analyzing kit according to the fifth embodiment of the present invention.

Referring to FIGS. 13 to 15, a specimen analyzing kit B10 according to a fifth embodiment of the present invention may be a kind of a strip that is inserted into a specimen analysis apparatus B1 (see FIGS. 16 and 17) that will be described later. The specimen analyzing kit B10 may include a case B100 defining an outer appearance thereof and an insertion position fixing unit B130 for stably inserting the case B100 into a main body B40.

Here, the main body B40 may be the case B100, i.e., an object in which the specimen analyzing kit B10 is inserted. Also, the main body B40 may be one component constituting the main body of the specimen analysis apparatus B1.

The case B100 may provide a predetermined inner space BS. Also, a reaction pad B140 may be disposed in the inner space BS.

The specimen analyzing kit B10 according to the fifth embodiment of the present invention may analyze multiple characteristics of the specimen at the same time by putting the specimen once. For this, a plurality of put-in holes B114 may be defined in the case B100.

In detail, the case B100 may include a cover unit B110 and a support unit B120 coupled to the cover unit B110 to define the predetermined inner space BS. The cover unit B110 may include a put-in part B112 in which the plurality of put-in holes B114 are defined and a result exposing part B116.

Here, the put-in part B112 may be recessed from a top surface of the cover unit B110 to protrude toward the inner space BS. The plurality of put-in holes B114 pass through a bottom surface of the put-in part B112.

Thus, when the specimen is put in the put-in part B112, the specimen may be introduced into the inner space BS through the plurality of put-in holes B114. Then, the specimen is permeated into the reaction pad A140 disposed under the put-in holes 114 to move into a reaction area of the reaction pad B140 by a chromatography.

As described above, the reaction area of the reaction pad A140 may be an area of which a color is changed by a flow rate difference due to the concentration of the analysis material of the specimen.

Thus, the reaction area of the reaction pad B140 may be exposed to the outside so that a user distinguishes the reaction area, and also the specimen analyzing kit B10 is inserted into the specimen analysis apparatus B1 including a camera BC to photograph a specimen reaction result displayed on the reaction area by using the camera BC, thereby obtaining the analyzed result of the specimen on the basis of a photographed image. For this, the cover unit B110 may include the result exposing part B116.

The result exposing part B116 may be disposed adjacent to the put-in part B112. Also, the result exposing part B116 may be a kind of hole for exposing all of reaction areas of a plurality of reaction pads B140.

Thus, the result exposing part B116 may have a size greater, somewhat, than those of the reaction areas of the plurality of reaction pads B140. As a result, the result exposing part B116 may have a size according to the sizes of the reaction areas of the reaction pads B140.

The reaction pads B140 may correspond to the put-in holes, respectively. The specimen introduced from the put-in holes B114 may be permeated into different reaction pads B140 without interfering with each other.

For example, when the specimen such as blood is put in the put-in part B112, the specimen may pass through the plurality of put-in holes B114 and then be permeated into the plurality of reaction pads B140. Thus, the multiple characteristics of the specimen may be analyzed at the same time by the reaction pads B140.

Here, although three reaction pads B140 and three put-in holes B114 are provided to achieve three specimen reaction results from one specimen in FIGS. 13 to 15, the present invention is not limited thereto. For example, the number of specimen reaction results may be variously changed by changing the number of put-in holes 114 and reaction pads B140.

Here, the interference between the specimens introduced from the put-in holes B114 may be prevented by at least one partition wall B122 by which the reaction pads B140 are disposed spaced apart from each other. As a result, the partition wall B122 may partition the inner space BS corresponding to the put-in holes B114.

Thus, the specimen analyzing kit B10 according to the present invention may previously prevent the specimens from interfering with each other in the process of analyzing the multiple characteristics of the specimen at the same time to obtain more accurate analysis results.

Particularly, the partition wall B122 for preventing the specimens from interfering with each other may protrude from a bottom surface of the support unit B120 toward the inner space BS. Also, the partition wall B122 may be disposed between the plurality of put-in holes B114.

That is, the partition wall B122 may support one side surface of an end of each of the reaction pads B140 to fix the reaction pad B140 to a position corresponding to that of each of the put-in holes B114. A fixing wall B124 disposed outside the partition wall B122 may support the other side surface of the end of the reaction pad B140.

That is, the outer reaction pads B140 may be supported by the partition wall B122 and the fixing wall B124 which respectively support one surface and the other surface of an end of each of the reaction pads B140. Also, one surface and the other surface of the middle reaction pad B140 may be supported by the two partition walls B122.

Thus, the reaction pads B140 may be spaced apart from each other by the partition wall B122. Thus, the reaction pads B140 may prevent the specimens introduced from the put-in holes B114 from interfering with each other and may be stably fixed within the inner space BS in the state where the reaction pads B140 are spaced apart from each other.

Here, one side surface and the other side surface of the other end of each of the reaction pads B140 may be supported by a partition corresponding wall B122' and a fixing corresponding wall B124' which respectively correspond to the partition wall B122 and the fixing wall B124. Thus, the reaction pads B140 may be stably fixed within the inner space BS.

The reaction pads B140 disposed within the inner space BS may receive a pressing force by at least one pressing protrusion B118. The pressing protrusion B118 may protrude from an upper inner surface of the cover unit B110 toward the inner space BS.

That is, the pressing protrusion B118 may press one surface of each of the reaction pads B140 disposed between the partition wall B122 and the fixing wall B124 and between the partition corresponding wall B122' and the fixing corresponding wall B124'. Here, the pressed portion may correspond to the outside of the reaction area of each of the reaction pads B140.

Thus, the reaction pads B140 may be more stably fixed within the inner space BS by the pressing protrusion B118 pressing a portion outside the reaction area without having an influence on the reaction area in which the specimen reaction result is shown.

The cover unit B110 and the support unit B120 constituting the case B100 may be coupled to each other by at least one coupling part B119 and at least coupling corresponding part B129. The coupling part B119 and the coupling corresponding part B129 may be coupled to each other through a press-fit method.

That is, the coupling part B119 may have a protrusion shape and protrude from an inner top surface of the cover unit B110. Also the coupling corresponding part B129 may have a groove shape and protrude from the bottom surface of the support unit B120.

Thus, the cover unit B110 and the support unit B120 may be coupled to each other by press-fitting the coupling part B119 into the coupling corresponding part B129. Here, the coupling part B119 and the coupling corresponding part B129 may be disposed opposite to each other.

At least one insertion position fixing part B130 recessed at least one predetermined position of both side surfaces along an insertion direction of the case B100 may be provided in the case B100 of the specimen analyzing kit B10 according to the fifth embodiment of the present invention to fix a position of the case B100 inserted into a main body B40 that is an object in which the case B100 is inserted.

That is, the insertion position fixing part B130 may be a component for stably fixing the case B100 into the main body B40 when the specimen analyzing kit B10 is inserted into the main body B40. Here, the stable fixing of the case B100 may be realized by inserting an insertion position fixing corresponding part B42 (see FIGS. 18A to 18D) into the main body B40.

The insertion position fixing parts B130 may be disposed at positions corresponding to each other in a state where each of the insertion position fixing parts B130 is recessed by a predetermined depth from both side surfaces along the insertion direction of the case B100. The insertion position fixing corresponding part B42 may be a kind of elastic protrusion.

The specimen analyzing kit B10 may be a component for fixing when the specimen analyzing kit B10 is inserted into the main body B40. The specimen analyzing kit B10 may include a vertical movement prevention part B135 in addition to the insertion position fixing part B130.

The vertical movement prevention part B135 may be a component for preventing the case B100 from being vertically moved within the main body B40. The vertical movement prevention part B135 may be recessed into an end of the case B100 in the insertion direction of the case B100.

Here, the vertical movement prevention part B135 may be recessed into a top surface of the case B100 and one surface of the case B100 in the insertion direction of the case B10. As a result, when the case B100 is inserted into the main body B40, a vertical movement prevention corresponding part B44 disposed on the main body B40 may be inserted to stably fix the case B100.

A detailed description with respect to the above-described process, i.e., a process of fixing the case B100 to the main body B40 by using the insertion position fixing part B130 and the vertical movement prevention part B135 will be described later with reference to FIGS. 16 to 18D.

An identification code B111 for obtaining information with respect to a reaction result between the specimen and the reaction pads B140 and a rib B113 may be disposed on one side and the other side of the cover unit B110, respectively.

Here, the identification code B111 may means information including a separate code value required to obtain effective information about the specimen reaction result.

For example, the identification code B111 may be manufacturing lot information with respect to the specimen analyzing kit B10 according to the present invention.

The manufacturing lot information of the specimen analyzing kit B10 may be used to calibrate a result of reading the specimen reaction result.

For another example, the identification code B111 may be an expire data of the specimen analyzing kit B10. The identification code B111 including the expire data may be used to determine whether the specimen analyzing kit B10 is used.

The rib B113 may be a kind of sliding prevention structure for preventing the specimen analyzing kit B10 from being slid when the specimen analyzing kit B10 is inserted into the main body B40.

Figure 16:
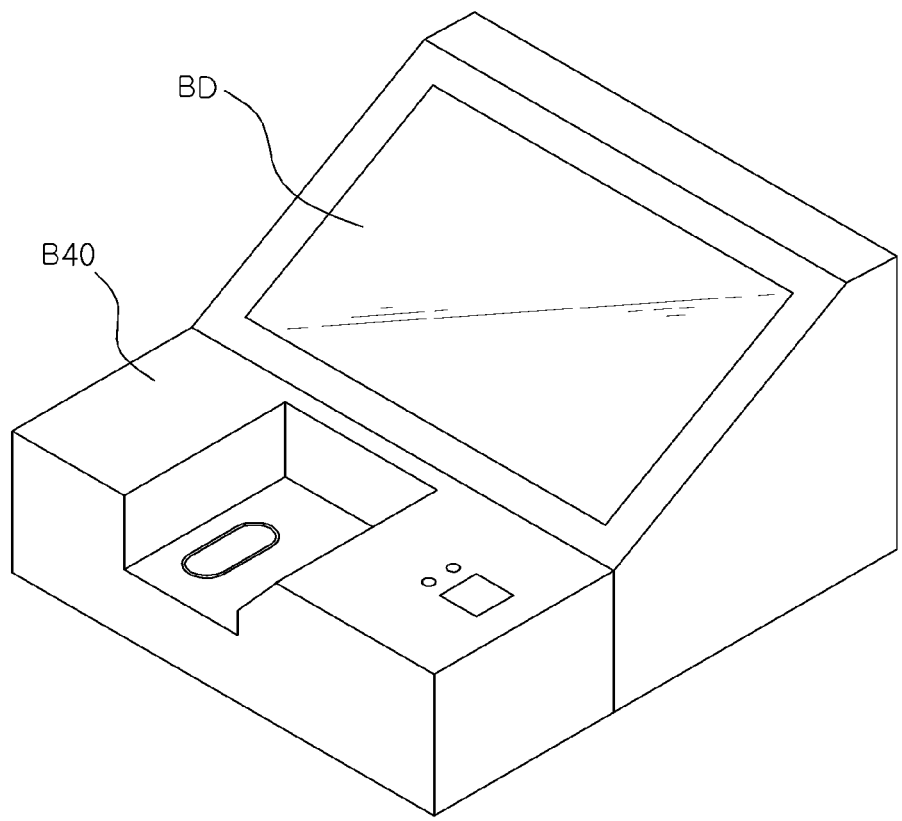
FIG. 16 is a schematic perspective view of a specimen analysis apparatus including the kit for specimen analyzing according to the fifth embodiment of the present invention.
Figure 17:
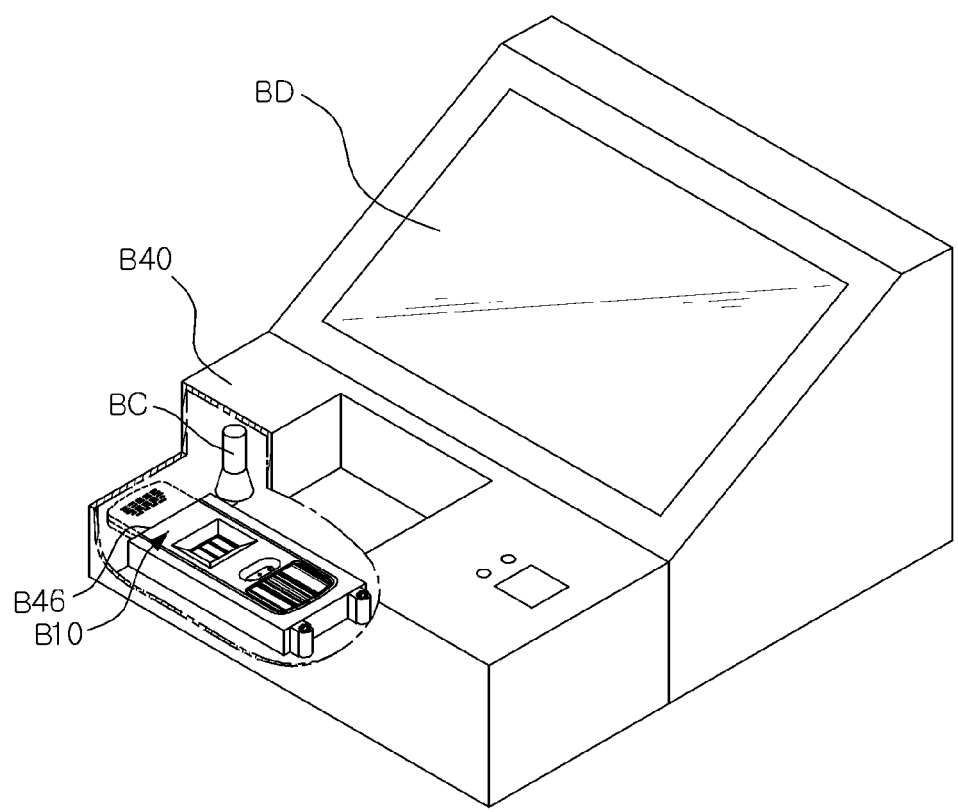
FIG. 17 is a schematic partial cutoff perspective view of the specimen analysis apparatus including the kit for specimen analyzing according to the fifth embodiment of the present invention.

FIG. 16 is a schematic perspective view of a specimen analysis apparatus including the kit for specimen analyzing according to the fifth embodiment of the present invention, and FIG. 17 is a schematic partial cutoff perspective view of the specimen analysis apparatus including the kit for specimen analyzing according to the fifth embodiment of the present invention.

Also, FIGS. 18A to 18D are schematic views illustrating a use state of the specimen analysis apparatus including the kit for specimen analyzing according to the fifth embodiment of the present invention, i.e., schematic views illustrating a process in which the kit for specimen analyzing is inserted into a main body.

Referring to FIGS. 16 and 17, a specimen analysis apparatus B1 according to the present invention may include the specimen analyzing kit B10 described with reference to FIGS. 13 to 15, the main body B40 in which the case B100 is inserted, and the insertion position fixing corresponding part B42 and vertical movement prevention corresponding part B44 which are disposed on the main body B40.

When the specimen analyzing kit B10 is inserted through an insertion hole B46 defined in the main body B40, the specimen analyzing kit B10 may be stably fixed by the insertion position fixing part B130 and the vertical movement prevention part B135.

This may be realized by respectively inserting the insertion position fixing corresponding part B42 and vertical movement prevention corresponding part B44 into the insertion position fixing part B130 and the vertical movement prevention part B135.

Hereinafter, in the specimen analysis apparatus B1, a process of obtaining an analyzed result by inserting the specimen analyzing kit B10 into the main body B40 will be described in detail.

Figure 18A:
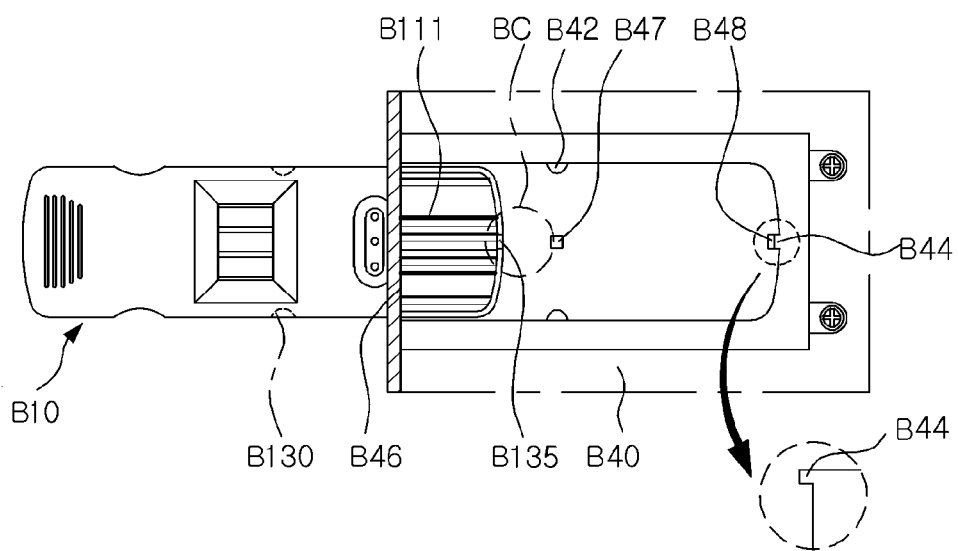
FIGS. 18A to 18D are schematic views illustrating a use state of the specimen analysis apparatus including the kit for specimen analyzing according to the fifth embodiment of the present invention, i.e., are schematic views illustrating a process in which the kit for specimen analyzing is inserted into a main body.

Referring to FIG. 18A, after a specimen such as blood is putted into the specimen analyzing kit B10, the specimen may move into reaction areas of the reaction pads B140 by a chromatography to obtain specimen reaction results that are results in the reaction areas.

Here, the specimen reaction results show multiple characteristics of the specimen by the plurality of put-in holes B114 and the plurality of reaction pads B140. Also, it may prevent the specimens from interfering with each other by the partition wall B122.

The specimen analyzing kit B10 is inserted into the main body B40 through the insertion hole B46 of the main body B40 so that the specimen reaction results of the above-described specimen analyzing kit B10 are photo grated to obtain analyzed results.

Figure 18B:
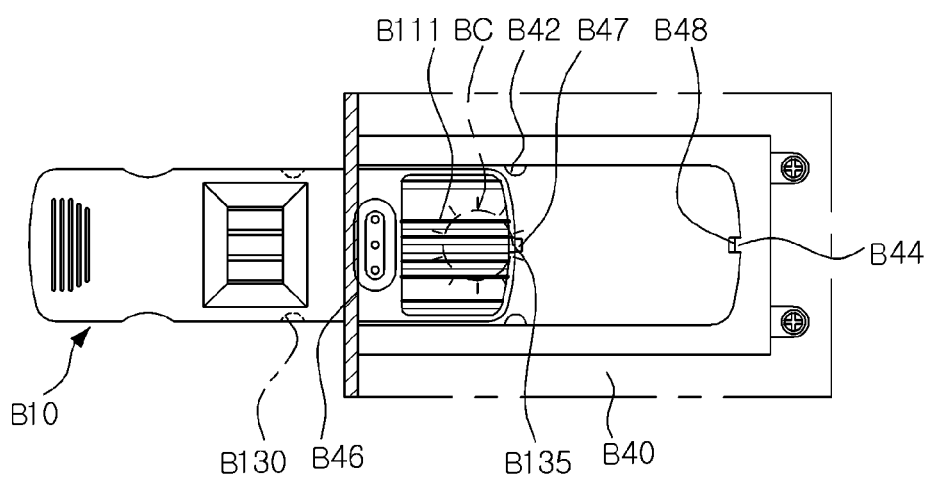

Referring to FIG. 18B, when the specimen analyzing kit B10 is inserted into the insertion hole B46 of the main body B40, a camera BC may be operated at some point to photograph the identification code B111 provided on the case B100.

That is, a first sensor B47 for detecting a position of the specimen analyzing kit B10 is attached to a bottom surface in a space in which the specimen analyzing kit B10 is inserted. When an end of the specimen analyzing kit B10 contacts the first sensor B47, the identification code B111 provided on the case B100 may be disposed under the camera BC. Thus, the camera BC may photograph the identification code B111 by interlocking with the operation of the first sensor B47.

However, although a photographing area of the camera BC has a size less, somewhat, than that of the identification code B111 in FIG. 18B, this is merely an example. For example, the photographing area of the camera BC may include an entire area of the identification code B111.

Figure 18C:
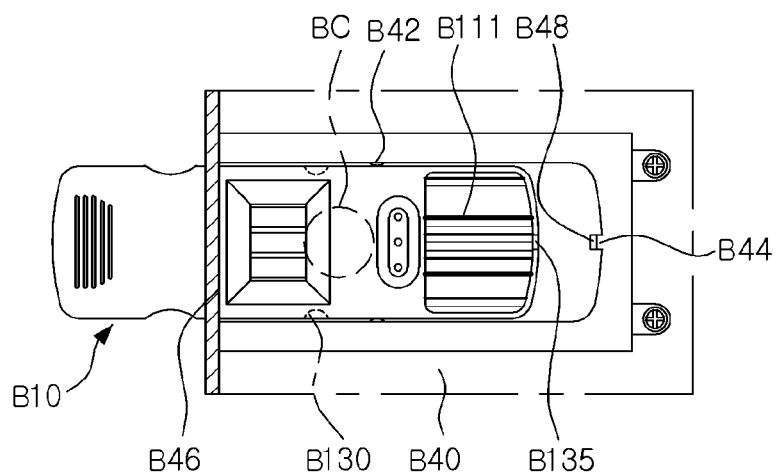

Referring to FIG. 18C, when an end of the specimen analyzing kit B10 is continuously inserted after contacting the first sensor B47, the insertion position fixing corresponding part B42 disposed on the main body B40 may be get behind somewhat by the outer appearance of the case B100.

That is, the insertion position fixing corresponding part B42 may have elasticity and protrude from the main body B40. While the specimen analyzing kit B10 is inserted, the insertion position fixing part B130 disposed on the case B100 may get behind by the elasticity until the insertion position fixing part B130 reaches a position corresponding to the insertion position fixing corresponding part B42.

Figure 18D:
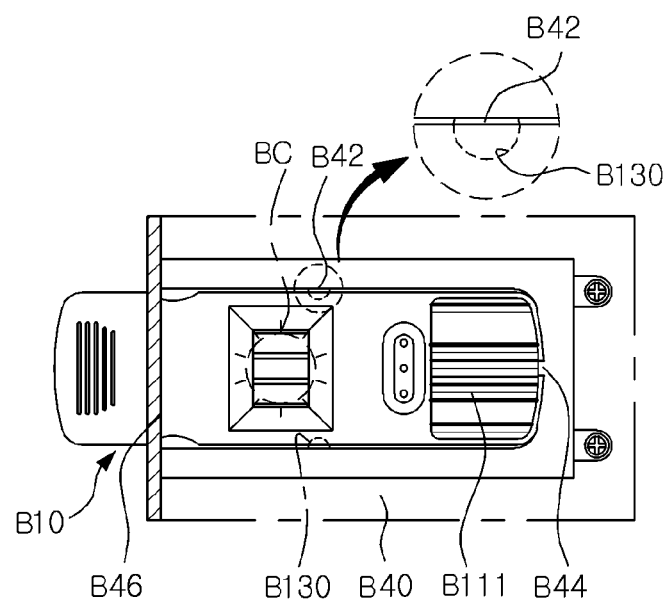

Referring to FIG. 18D, when an end of the specimen analyzing kit B10 reaches a boundary of the space of the main body B40 in which the specimen analyzing kit B10 is inserted, the camera BC may be operated again at this point.

That is, a second sensor B48 for detecting the position of the specimen analyzing kit B10 is attached to a bottom surface of the boundary of the space in which the specimen analyzing kit B10 is inserted. When an end of the specimen analyzing kit B10 contacts the second sensor B48, the result exposing part B116 disposed on the case B100 may be disposed under the camera BC. Thus, the camera BC may photograph the result exposing part B116 by interlocking with the operation of the second sensor B48.

Here, the insertion position fixing corresponding part B42 may correspond to the specimen analyzing kit B10, i.e., the insertion position fixing part B130 disposed on the case B100. The insertion position fixing corresponding part B42 may be inserted into the insertion position fixing part B130 by a restoring force thereof to fix the case B100 to the main body B40.

The case B100 may be more stably fixed to the main body B40 by the vertical movement prevention part B135. This may be realized by inserting the vertical movement prevention corresponding part B44 disposed on the boundary of the space, in which the specimen analyzing kit B10 is inserted, into the vertical movement prevention part B135.

That is, the vertical movement prevention part B135 may be disposed to correspond to the vertical movement prevention corresponding part B44. Thus, the movement of the case B100 may be prevented by the vertical movement prevention corresponding part B44 inserted into the vertical movement prevention part B135.

Thus, the insertion position fixing corresponding part B42 and vertical movement prevention corresponding part B44 which are disposed on the main body B40 may be respectively inserted into the insertion position fixing part B130 and the vertical movement prevention part B135 to stably fix the specimen analyzing kit B10 to the inside of the main body B40.

Thus, it may previously prevent the specimen analyzing kit B10 from moving, i.e., peeling off within the main body B40 to realize an accurate specimen analysis.

After the specimen reaction results of the reaction areas exposed through the result exposing part B116 is photographed by the camera BC, a control unit analyzes read results of the specimen reaction results by using a read result of an image of the identification code B111 to output the analyzed results through the display part BD.

Particularly, when the identification code B111 is the manufacturing lot information of the specimen analyzing kit B10, the control unit calibrates a result of reading the specimen reaction results by using the manufacturing lot information read from the identification code B111.

When the identification code B111 is the expire data of the specimen analyzing kit B10, the control unit may output an error message in a case where the expire date passes on the basis of the read result of the identification code B111.

Also, when the identification code B111 represents a kind of specimen to be analyzed in the specimen analyzing kit B10, the control unit may output an error message for informing impossibility of the analysis in a case where a kind of specimen to be analyzed does not correspond to a kind of specimen analyzed by the measuring device according to the read result of the identification code B111.

Sixth Embodiment

Figure 19:
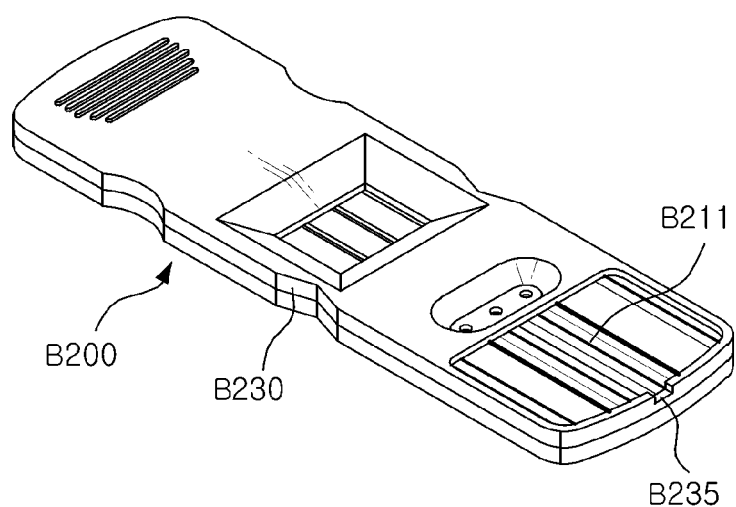
FIG. 19 is a schematic perspective view of a kit for specimen analyzing according to a sixth embodiment of the present invention.
Figure 20A:
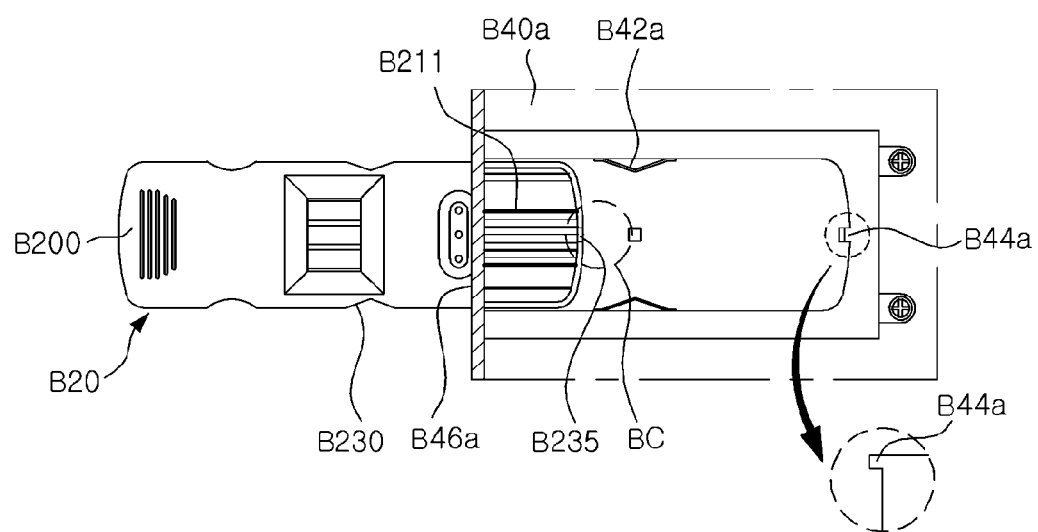
FIGS. 20A to 20D are schematic views illustrating a use state of a specimen analysis apparatus including the kit for specimen analyzing of FIG. 19, i.e., are schematic views illustrating a process in which the kit for specimen analyzing is inserted into a main body.
Figure 20B:
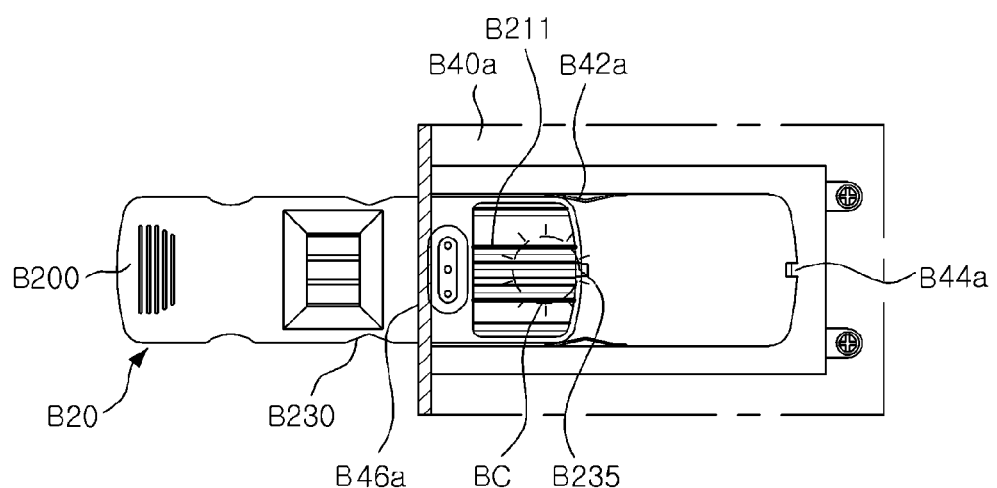
Figure 20C:
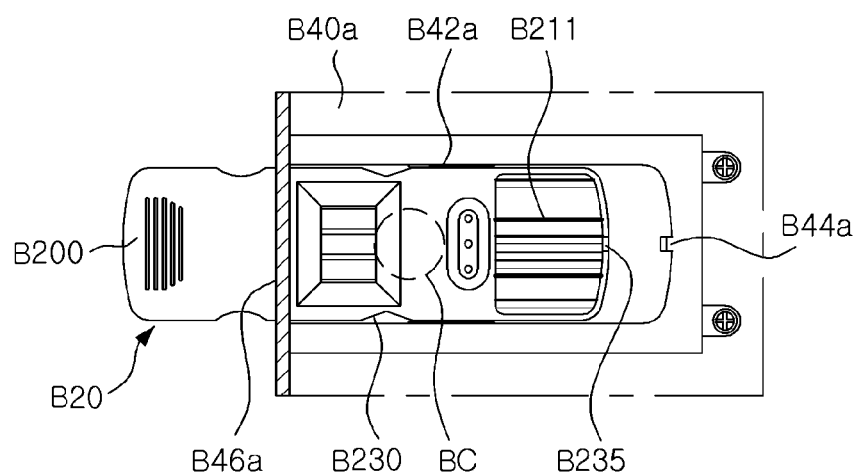
Figure 20D:
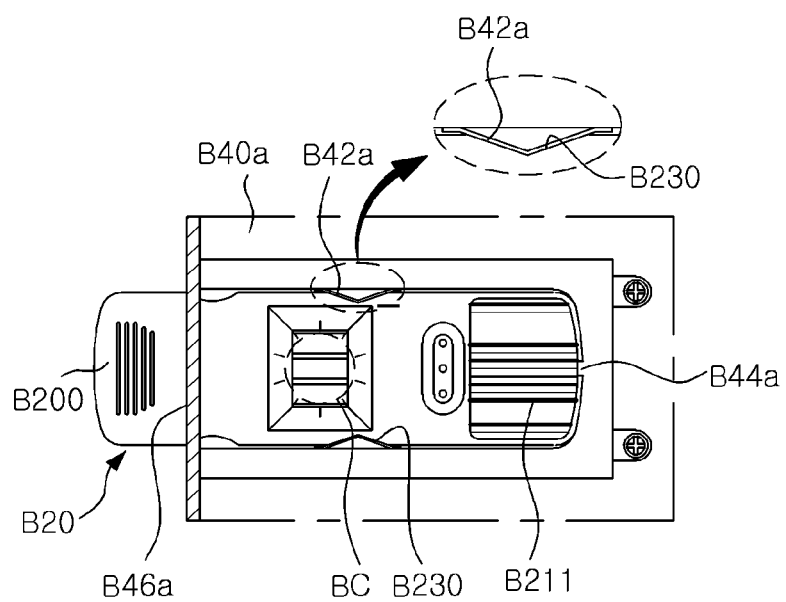

FIG. 19 is a schematic perspective view of a kit for specimen analyzing according to a sixth embodiment of the present invention, and FIGS. 20A to 20D are schematic views illustrating a use state of a specimen analysis apparatus including the kit for specimen analyzing of FIG. 19, i.e., are schematic views illustrating a process in which the kit for specimen analyzing is inserted into a main body.

Referring to FIGS. 19 to 20, a specimen analyzing kit B20 according to a sixth embodiment of the present invention is equal to the specimen analyzing kit B10 according to the fifth embodiment of the present invention, which is described with reference to FIGS. 16 to 18D, in constitution and effect except for insertion position fixing parts B230 and insertion position fixing corresponding parts B42a. Thus, descriptions of components except for the insertion position fixing parts B230 and the insertion position fixing corresponding parts B42a will be omitted.

First, the insertion position fixing parts B230 may be respectively recessed from both side surfaces in an insertion direction of a case B200 into a main body B40a. Also, the insertion position fixing parts B230 may be disposed at positions corresponding to each other.

Also, the insertion position fixing parts B230 may communicate with top and bottom surfaces of the case B200. When viewed from an upper or lower side, each of the insertion position fixing parts B230 may have a triangular shape.

Correspondingly, the insertion position fixing corresponding parts B42a disposed on the main body B40a may correspond to the insertion positing fixing parts B230, respectively. Each of the insertion position fixing corresponding parts B42a may have a curved plate shape and get behind or resorted by elasticity.

That is, after the specimen analyzing kit B20 is inserted into an insertion hole B46a of the main body B40a, and an identification code B211 is photographed by a camera BC, the specimen analyzing kit B20 may be continuously inserted. As a result, the insertion position fixing corresponding parts B42a may be elastically deformed, i.e., get behind. Then, when the specimen analyzing kit B20 reaches a boundary of a space of the main body B40a in which the specimen analyzing kit B20 is inserted, the insertion position fixing corresponding parts B42a may be restored and inserted into the insertion position fixing part B230 disposed on the case B200.

Here, a process of inserting a vertical movement prevention corresponding part B44a into a vertical movement prevention part B235 is equal to that described with respect to FIGS. 16 to 18D.

Thus, the insertion position fixing corresponding part B42a and the vertical movement prevention corresponding part B44a which are disposed on the main body B40a may be respectively inserted into the insertion position fixing part B230 and the vertical movement prevention part B235 to stably fix the specimen analyzing kit B20 to the inside of the main body B40a.

Seventh Embodiment

Figure 21:
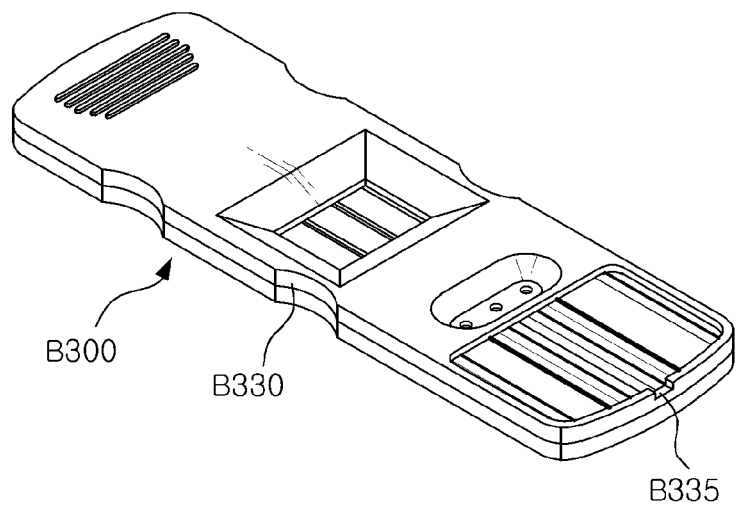
FIG. 21 is a schematic perspective view of a kit for specimen analyzing according to a seventh embodiment of the present invention.
Figure 22A:
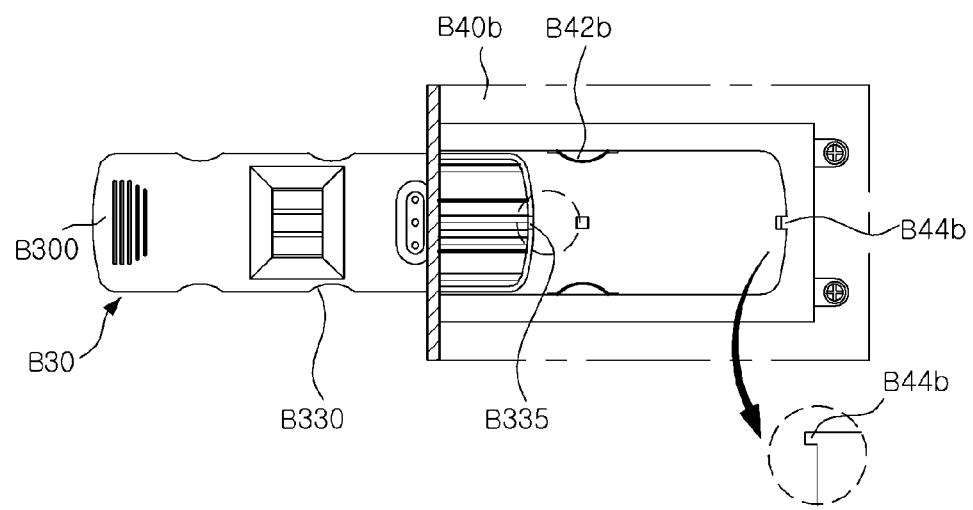
FIGS. 22A to 22D are schematic views illustrating a use state of a specimen analysis apparatus including the kit for specimen analyzing of FIG. 19, i.e., are schematic views illustrating a process in which the kit for specimen analyzing is inserted into a main body.
Figure 22B:
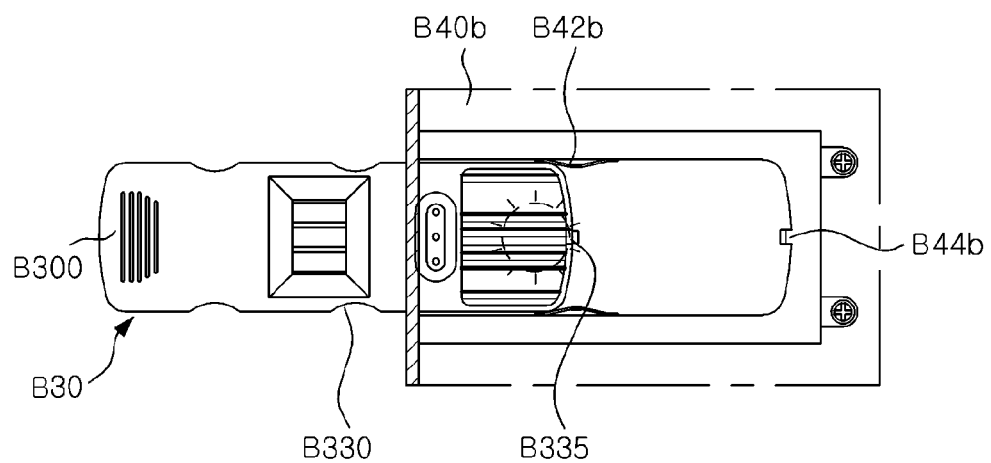
Figure 22C:
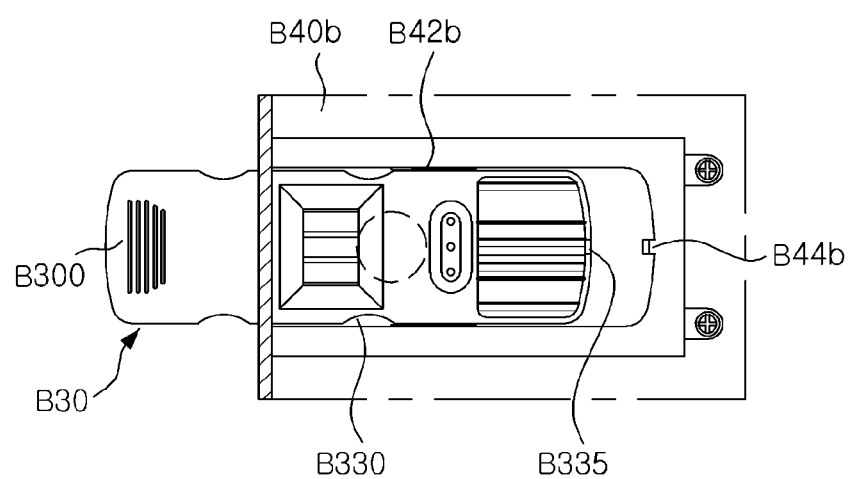
Figure 22D:
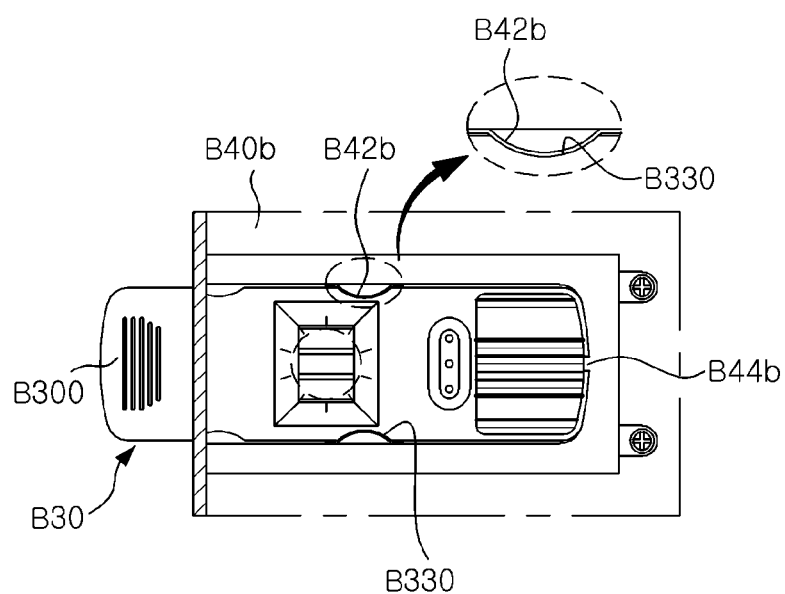

FIG. 21 is a schematic perspective view of a kit for specimen analyzing according to a seventh embodiment of the present invention, and FIGS. 22A to 22D are schematic views illustrating a use state of a specimen analysis apparatus including the kit for specimen analyzing of FIG. 19, i.e., are schematic views illustrating a process in which the kit for specimen analyzing is inserted into a main body.

Referring to FIGS. 21 to 22, a specimen analyzing kit B30 according to a seventh embodiment of the present invention is equal to the specimen analyzing kit B10 according to the fifth embodiment of the present invention, which is described with reference to FIGS. 16 to 18D, in constitution and effect except for an insertion position fixing part B330 and an insertion position fixing corresponding part B42b. Thus, descriptions of components except for the insertion position fixing part B330 and the insertion position fixing corresponding part B42b will be omitted.

Also, the insertion position fixing part B330 may communicate with top and bottom surfaces of the case B300. When viewed from an upper or lower side, the insertion position fixing part B330 may have an arc shape.

Correspondingly, the insertion position fixing corresponding part B42b disposed on the main body B40b may correspond to the insertion positing fixing part B330. The insertion position fixing corresponding part B42b may have a roundly curved left spring shape and get behind or resorted by elasticity.

In addition, an insertion position fixing corresponding part B42b and a vertical movement prevention corresponding part B44b which are disposed on the main body B42 may be respectively inserted into the insertion position fixing part B330 and a vertical movement prevention part B335 to stably fix the specimen analyzing kit B30 to the inside of the main body B40b.

Eighth Embodiment

Figure 23:
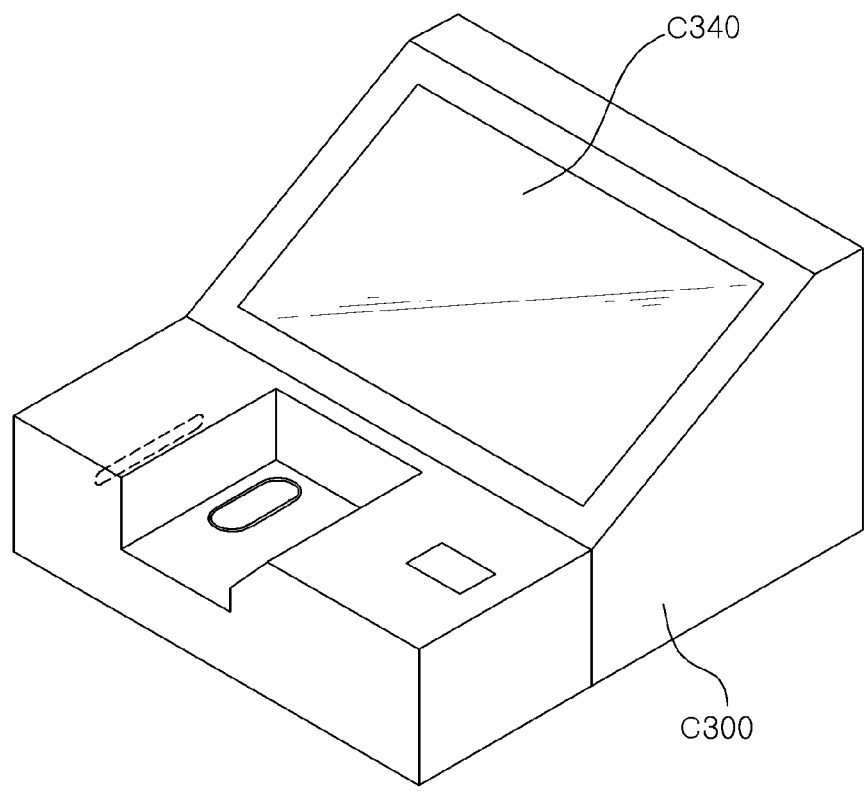
FIG. 23 is a schematic perspective view of a kit for specimen analyzing according to an eighth embodiment of the present invention.
Figure 24:
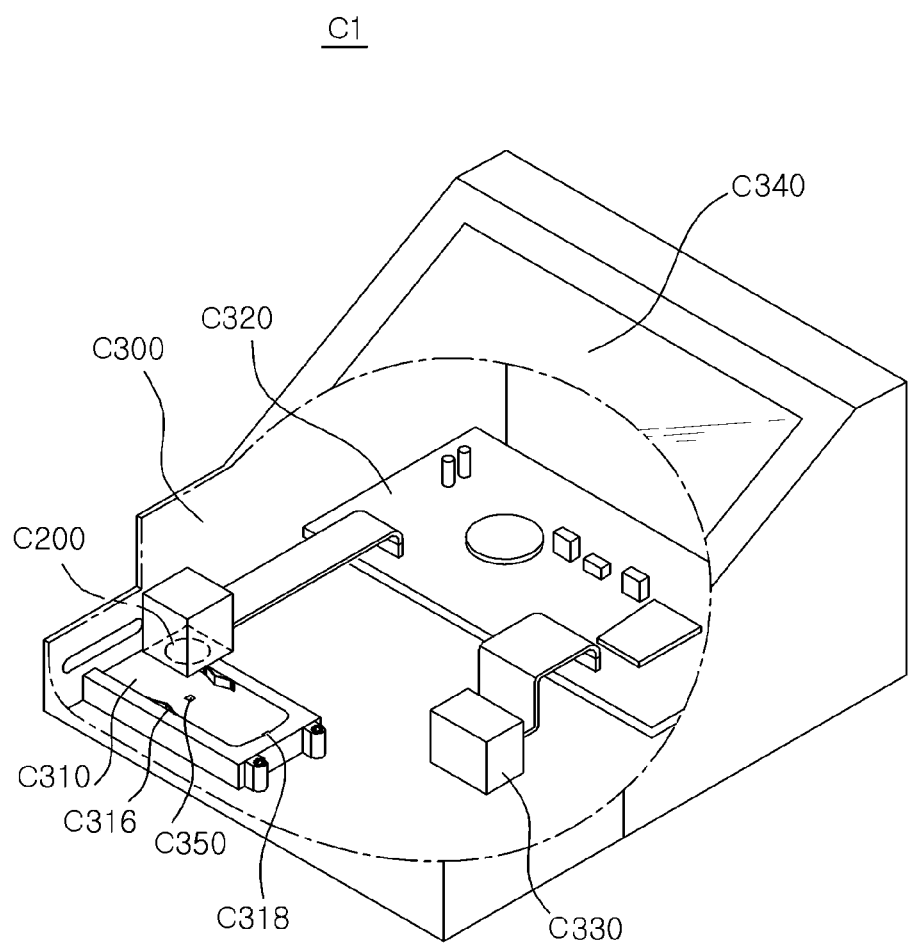
FIG. 24 is a schematic cutoff perspective view of a specimen analysis apparatus according to the eighth embodiment of the present invention.

FIG. 23 is a schematic perspective view of a kit for specimen analyzing according to an eighth embodiment of the present invention, and FIG. 24 is a schematic cutoff perspective view of a specimen analysis apparatus according to the eighth embodiment of the present invention.

Figure 25:
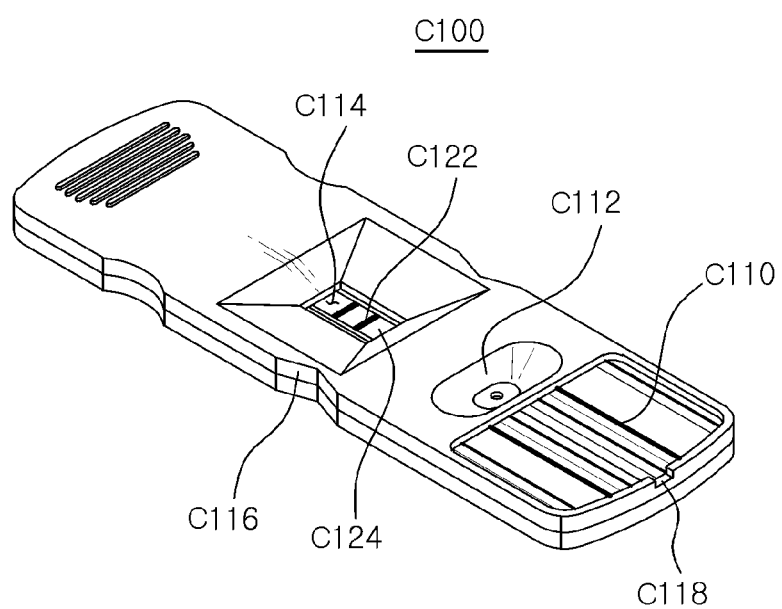
FIG. 25 is a schematic perspective view of a kit for specimen analyzing that is an object to be analyzed by the specimen analysis apparatus according to the eighth embodiment of the present invention.
Figure 26:
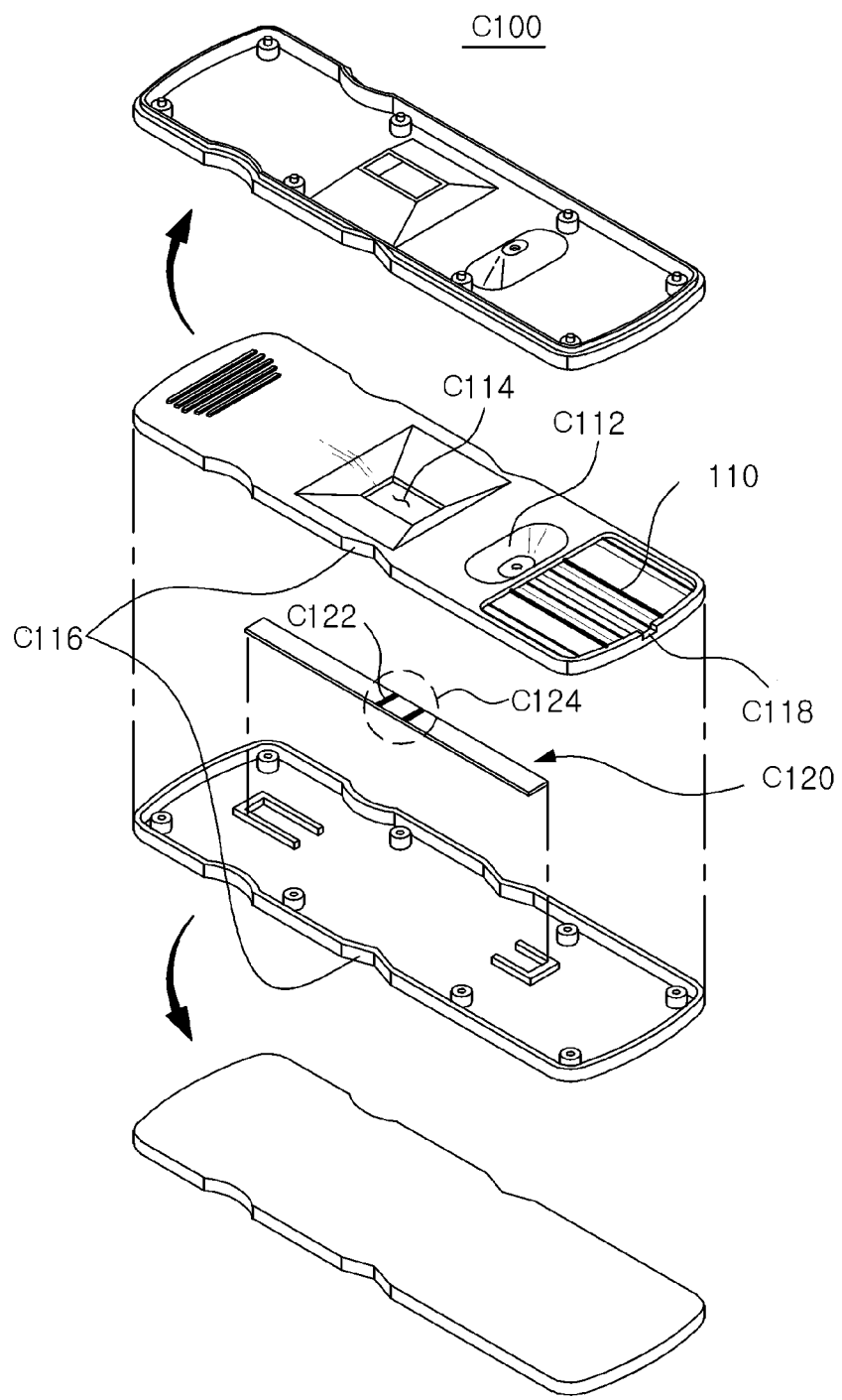
FIG. 26 is a schematic perspective view of the kit for specimen analyzing that is the object to be analyzed by the specimen analysis apparatus according to the eighth embodiment of the present invention.

FIG. 25 is a schematic perspective view of a kit for specimen analyzing that is an object to be analyzed by the specimen analysis apparatus according to the eighth embodiment of the present invention, and FIG. 26 is a schematic perspective view of the kit for specimen analyzing that is the object to be analyzed by the specimen analysis apparatus according to the eighth embodiment of the present invention.

Referring to FIGS. 23 to 26, a specimen analysis apparatus C1 according to an eighth embodiment of the present invention may include an image photographing unit C200 for photographing a specimen analyzing kit C100 and a main body C300 on which the image photographing unit C200 is mounted.

The main body C300 may define an outer appearance of the specimen analysis apparatus C1 according to the eighth embodiment of the present invention. Also, the main body C300 may provide an inner space in which the image photographing unit C200, a control unit C320 that will be described later, and a data storage unit C330 are mounted.

The image photographing unit C200 may be disposed above an insertion unit C310 of the main body C300, i.e., an insertion unit C310 in which the specimen analyzing kit C100 is inserted and mounted. The image photographing unit C200 may be a kind of camera for photographing an identification code C110 provided on the specimen analyzing kit C100 and a specimen reaction result C122.

Here, the image photographing unit C200 may photograph the specimen analyzing kit C100 and the specimen reaction result C122 with a time difference.

That is, the image photographing unit C200 may successively photograph the identification code C110 and the specimen reaction result C122 by moving the specimen analyzing kit C100. Then, the image photographing unit C200 may be configured to conclude an analyzed result of the specimen on the basis of the photographed image.

Here, the specimen reaction result C122 described above may represent a result reacting by moving the specimen, which is injected into the specimen analyzing kit C100, into a reaction area C124 of the reaction pad C120 provided inside the specimen analyzing kit C100.

That is, when the specimen collected from blood is injected into a specimen put-in hole A112 of the specimen analyzing kit C100, the specimen moves into the reaction area C124 of the reaction pad C120 after a predetermined time passes to react. Thus, a result of the reaction area C124 may be defined as the specimen reaction result C122.

For example, when the specimen collected from the blood moves into the reaction area C124 by the chromatography to react, the reaction area C124 may be changed in color by a flow rate difference due to a concentration of an analysis material contained in the specimen. Here, the changed color in the reaction area C124 may be the specimen reaction result.

The specimen reaction result C122 may be implemented in at least one band shape. Thus, the band shape may be analyzed to analyze health conditions of a subject from which the specimen is collected.

Thus, it may be necessary to expose the reaction area C124 of the reaction pad C120 to the outside so that the subject distinguishes the reaction area C124. For this, the specimen analyzing kit C100 may include a result exposing part C114.

However, the specimen reaction result exposed through the result exposing part C114 may be used for accurately analyzing health conditions of a subject by using the specimen analysis apparatus C1. Here, this may be realized by the image photographing unit C200.

Here, the identification code C110 photographed by the image photographing unit C200 may means information including a separate code value required to obtain effective information about the specimen reaction result C122.

For example, the identification code C110 may be manufacturing lot information with respect to the specimen analyzing kit C100 according to the present invention.

The manufacturing lot information of the specimen analyzing kit C100 may be used to calibrate a result of reading the specimen reaction result.

For another example, the identification code C110 may be an expire data of the specimen analyzing kit C100. The identification code C110 including the expire data may be used to determine whether the specimen analyzing kit C100 is used.

As a result, the image photographing unit C200 successively photographs the identification code C110 and the specimen reaction result C122. The control unit C320 reads an identification code image and a specimen reaction result image from the photographed image, and then the read result is displayed on the display part C340.

The photographing of the image photographing unit C200 may be performed by a sensor C350 disposed in an insertion unit C310 of the main body C300, and its description will be described later with reference to FIGS. 27 to 30.

Figure 27:
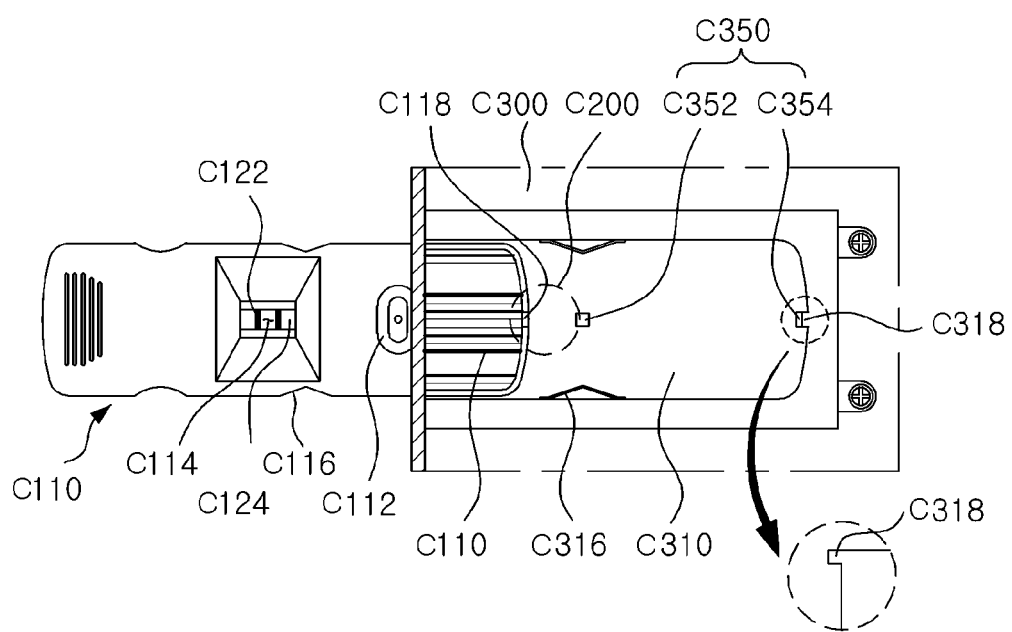
FIGS. 27 to 30 are schematic views illustrating an operation process of the specimen analysis apparatus according to the eighth embodiment of the present invention.
Figure 30:
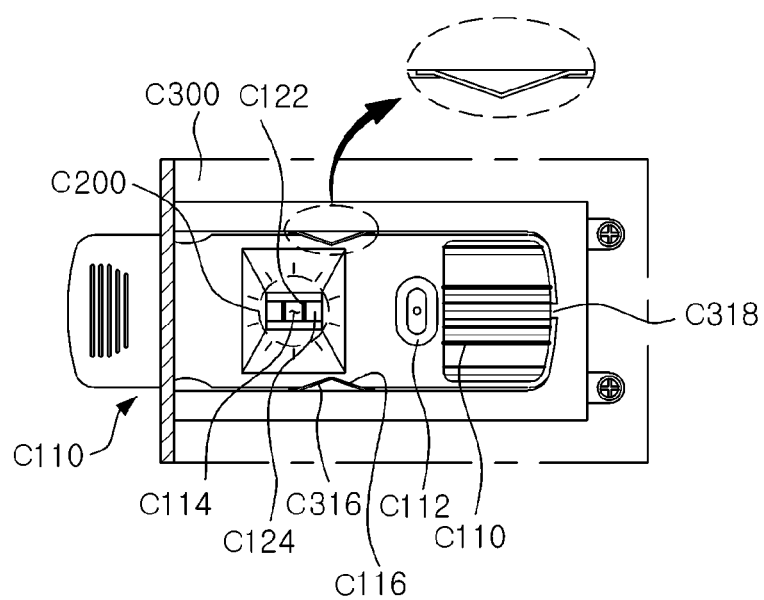

Also, when the specimen analyzing kit C100 is inserted and mounted through the insertion unit C310 of the main body C300, this process may be realized by an insertion position fixing part C116 and a vertical movement prevention part C118 which are disposed on the specimen analyzing kit C100 and an insertion position fixing corresponding part C316 and a vertical movement prevention corresponding part C318 which are disposed on the insertion unit C310, and its description will be described later with reference to FIGS. 27 and 30.

The specimen analysis apparatus C1 according to the eighth embodiment of the present invention may be operated in two modes.

Particularly, the first mode may be a mode in which the specimen analyzing kit C100 on which the specimen reaction result C122 is displayed is inserted and mounted into the insertion unit C310 of the main body C300 and then is analyzed. The second mode may be a mode in which the specimen analyzing kit C100 in which the specimen is not injected is inserted and mounted into the main body C300, and then the specimen is injected to analyze the specimen reaction result C122.

Thus, since the specimen analysis apparatus C1 according to the present invention is selectively realized in a mode desired by a user, user's convenience may be maximized.

Here, a detailed operation order in the first mode will be described with reference to FIGS. 27 to 30, and a detailed operation order in the second mode will be described with reference to FIGS. 31 to 36.

FIGS. 27 to 30 are schematic views illustrating an operation process of the specimen analysis apparatus according to the eighth embodiment of the present invention.

FIGS. 27 to 30 illustrate an operation process corresponding to the first mode in the specimen analysis apparatus C1 according to the present invention. That is, FIGS. 27 to 30 illustrate the first mode in which the specimen is injected through the specimen put-in hole C112 to analyze the specimen analyzing kit C100 on which the specimen reaction result is displayed on the reaction area C124 of the reaction pad C120.

Referring to FIG. 27, after a specimen such as blood is putted into the specimen analyzing kit C100, the specimen may move into the reaction area C124 of the reaction pad C120 by a chromatography to obtain the specimen reaction result that is a result in the reaction area C124.

The specimen analyzing kit C100 on which the specimen reaction result C122 is displayed is inserted into the main body C300 through the insertion unit C310 of the main body C300 by successively photographing the identification code C110 and the specimen reaction result C122 with a time difference to obtain the analyzed result on the basis of the photographed image.

Figure 28:
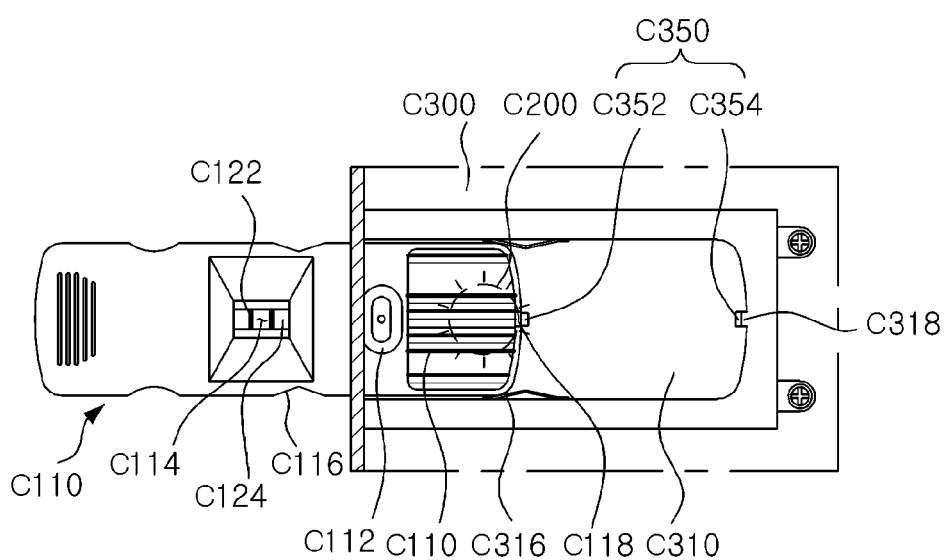

Referring to FIG. 28, when the specimen analyzing kit C100 is inserted into the insertion unit C310 of the main body C300, the image photographing unit C200 may be operated at some point to photograph the identification code C110 disposed on the specimen analyzing kit C100.

That is, the image photographing unit C200 may photograph the identification code C110 according to a change in position due to the movement of the specimen analyzing kit C100. As a result, the photographing of the image photographing unit C200 may be determined according to a position of the specimen analyzing kit C100.

This may be realized by the sensor C350 that provides a signal with respect to the photographing of the image photographing unit C200 according to the position of the specimen analyzing kit C100. The sensor C350 may be mounted on a bottom surface of the insertion unit C310.

The sensor C350 may react by contacting an end of the specimen analyzing kit C100. Also, the sensor C350 may include a first sensor C352 and a second sensor C354.

That is, the first and second sensors C352 and C354 may be successively operated by contacting the end of the specimen analyzing kit C100 while the specimen analyzing kit C100 is inserted into the insertion unit C310.

That is to say, when the end of the specimen analyzing kit C100 contacts the first sensor C352, the identification code C110 disposed on the specimen analyzing kit C100 is disposed under the image photographing unit C200. The image photographing unit C200 may photograph the identification code C110 by the signal of the first sensor C352.

Here, an image photographing the identification code C110 may be read by the control unit C320 and then be used as data for concluding an accurate analysis result of the specimen.

However, although a photographing area of the image photographing unit C200 has a size less, somewhat, than that of the identification code C110, this is merely an example. For example, the photographing area of the image photographing unit C200 may include an entire area of the identification code C110.

Figure 29:
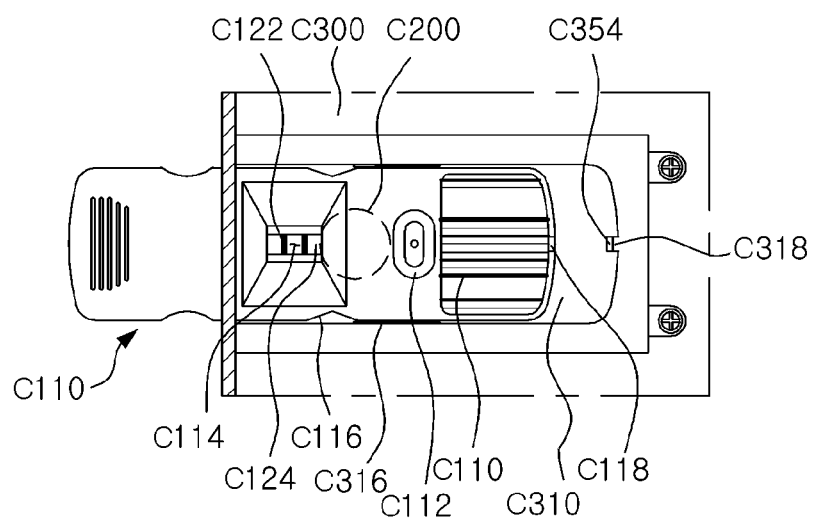

Referring to FIG. 29, when the end of the specimen analyzing kit C100 is continuously inserted after contacting the first sensor C352, the insertion position fixing corresponding part C316 disposed on the main body C300 may be get behind somewhat by the outer appearance of the specimen analyzing kit C100.

That is, the insertion position fixing corresponding part C316 may have elasticity and protrude from both side surfaces of the insertion unit C310 of the main body C300. While the specimen analyzing kit C100 is inserted, the insertion position fixing corresponding part C316 may get behind by the elasticity until the insertion position fixing part C116 recessed from each of both sides of the specimen analyzing kit C100 reaches a position corresponding to the insertion position fixing corresponding part C316.

Referring to FIG. 30, when the end of the specimen analyzing kit C100 reaches a boundary of a space of the main body C300 is inserted, the image photographing unit C200 may be operated again at this point.

That is, the second sensor C354 for detecting the position of the specimen analyzing kit C100 is attached to a bottom surface of the boundary of the space in which the specimen analyzing kit C100 is inserted. When the end of the specimen analyzing kit C100 contacts the second sensor C354, the result exposing part C114 disposed on the specimen analyzing kit C100 may be disposed under the image photographing unit C200. Thus, the image photographing unit C200 may photograph the result exposing part C114 by interlocking with the operation of the second sensor C354.

Here, the insertion position fixing corresponding part C316 may correspond to the insertion position fixing part C116 disposed on the specimen analyzing kit C100. The insertion position fixing corresponding part C316 may be inserted into the insertion position fixing part C116 by a restoring force thereof to fix the specimen analyzing kit C100 to the insertion unit C310 of the main body C300.

The specimen analyzing kit C100 may be more stably fixed to the insertion unit C310 of the main body C300 by the vertical movement prevention part C118. This may be realized by inserting the vertical movement prevention corresponding part C318 disposed on the boundary of the space, in which the specimen analyzing kit C100 is inserted, into the vertical movement prevention part C118.

That is, the vertical movement prevention part C118 may be disposed to correspond to the vertical movement prevention corresponding part C318. Thus, the vertical movement of the specimen analyzing kit C100 may be prevented by the vertical movement prevention corresponding part C318 inserted into the vertical movement prevention part C118.

Thus, the insertion position fixing corresponding part C316 and vertical movement prevention corresponding part C318 which are disposed on the insertion unit C310 of the main body C300 may be respectively inserted into the insertion position fixing part C116 and the vertical movement prevention part C118 to stably fix the specimen analyzing kit C100 to the inside of the main body C300.

Thus, it may previously prevent the specimen analyzing kit C100 from moving, i.e., peeling off within the main body C300 to realize an accurate specimen analysis.

When the specimen reaction result C122 in the reaction area C124 exposed through the result exposing part C114 is photographed by the image photographing unit C200, the control unit C320 may read the identification code image and the specimen reaction result image, which are previously photographed, to process the read result of the specimen reaction result by using the read result of the identification code C110.

Here, the control unit C320 may receive information corresponding to the identification code C110 read from a data storage unit C330 in which information corresponding to the identification code C110 is stored to obtain effective information with respect to the specimen analysis.

That is, the data storage unit C330 may store information with respect to the identification code C110 of the specimen analyzing kit C100 by using an RFID.

Particularly, when the identification code C110 is the manufacturing lot information of the specimen analyzing kit C100, the control unit C320 calibrates a result of reading the specimen reaction result by using the manufacturing lot information read from the identification code C320. Here, the processed result may be displayed through the display part C340.

When the identification code C110 is the expire data of the specimen analyzing kit C100, the control unit C320 may output an error message in a case where the expire date passes on the basis of the read result of the identification code C320.

Also, when the identification code C110 represents a kind of specimen to be analyzed in the specimen analyzing kit C100, the control unit C320 may output an error message for informing impossibility of the analysis on the display part C340 in a case where a kind of specimen to be analyzed does not correspond to a kind of specimen analyzed by a measuring device according to the read result of the identification code C110.

In summary, the specimen analysis apparatus C1 according to the present invention may include the image photographing unit C200 to accurately analyze the specimen. The image photographing unit C200 may successively photograph the identification code C110 and the specimen reaction result C122 according to a change in position due to the movement of the specimen analyzing kit C100 within the insertion unit C310 of the main body C300.

That is to say, the photographing of the image photographing unit C200 may be determined according to the position of the specimen analyzing kit C100. Particularly, the image photographing unit C200 may successively photograph the identification code C110 and the specimen reaction result C122 with a time difference by signals of the first and second sensors C352 and C354.

Here, the control unit C320 may read the photographed identification code image and specimen reaction result image to process the read result of the specimen reaction result C122 by using the read result of the identification code C110. The result may be outputted through the display part C340.

Thus, since the specimen analysis apparatus C1 according to the present invention may realize accurate analysis of the specimen through the singular image photographing unit C200, the specimen analysis apparatus C1 may be miniaturized and simplified.

FIGS. 31 to 35 are schematic views illustrating a modified example of the operation process of the specimen analysis apparatus according to the eighth embodiment of the present invention.

FIGS. 31 to 35 illustrate an operation process corresponding to the second mode in the specimen analysis apparatus C1 according to the present invention. That is, FIGS. 31 to 35 illustrate the second mode in which the specimen analyzing kit C100, in which the specimen is not injected, is inserted and mounted into the main body C300, and then, the specimen is injected to analyze the specimen.

Figure 31:
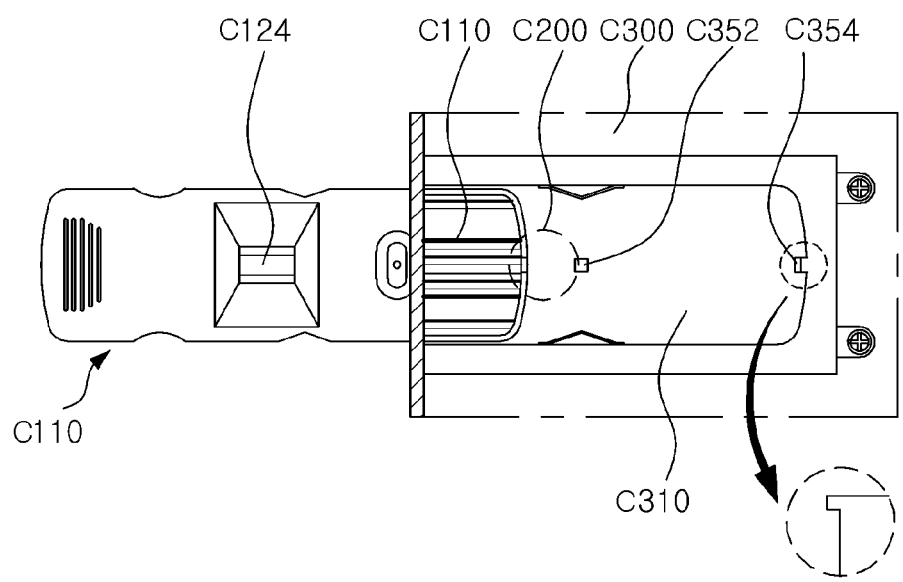
FIGS. 31 to 35 are schematic views illustrating a modified example of the operation process of the specimen analysis apparatus according to the eighth embodiment of the present invention.

Referring to FIG. 31, the specimen analyzing kit C100 in which the specimen is not injected may be inserted into the main body C300 through the insertion unit C310.

Figure 32:
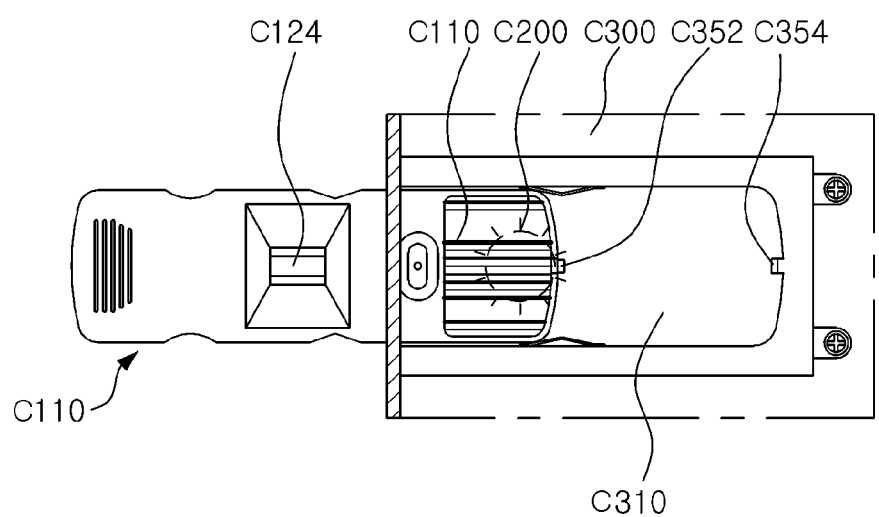

Referring to FIG. 32, while the specimen analyzing kit C100 in which the specimen is not injected is inserted, the specimen analyzing kit C100 may contact the first sensor C352. The image photographing unit C200 may photograph the identification code C110 by the signal of the first sensor C352.

Figure 33:
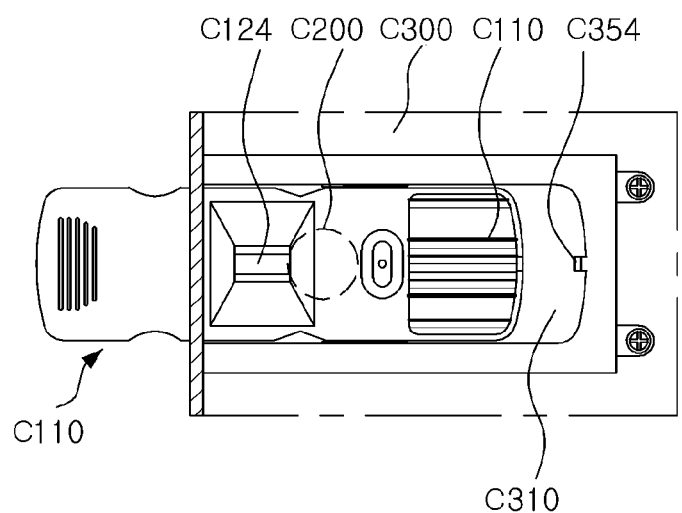

Referring to FIG. 33, the specimen analyzing kit C100 in which the specimen is not injected may be continuously inserted after the end of the specimen analyzing kit C100 contacts the first sensor C352.

Figure 34A:
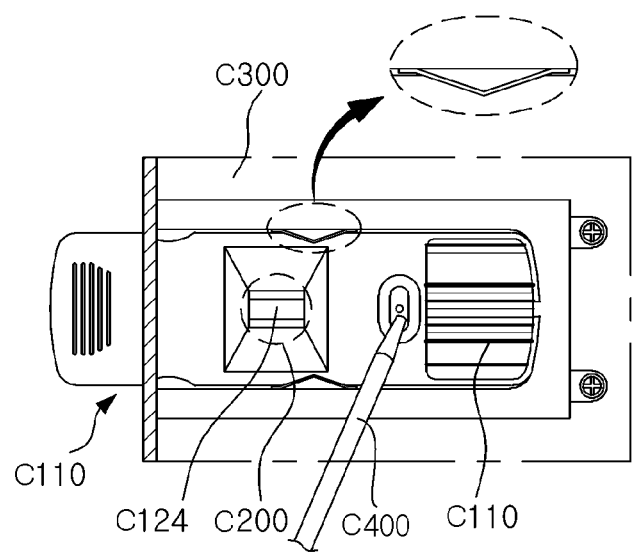
Figure 34B:
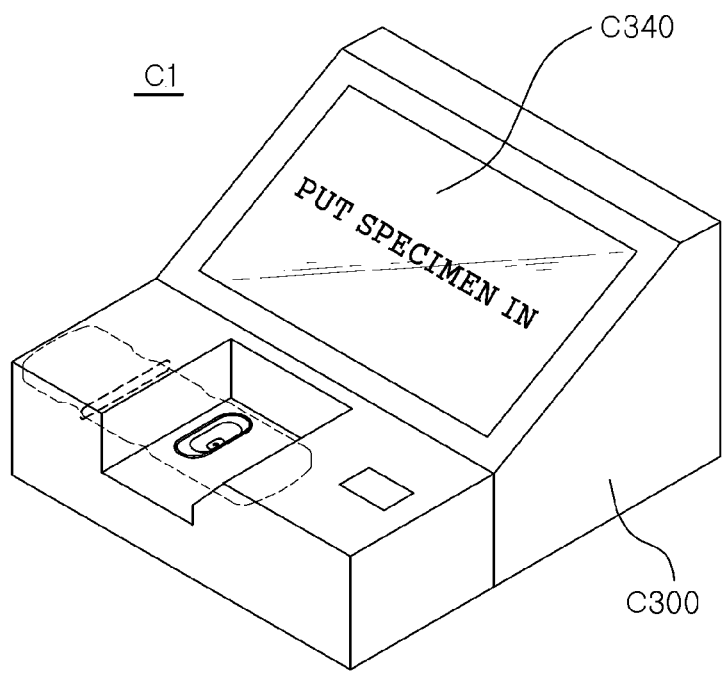

Referring to FIGS. 34A and 34B, when the end of the specimen analyzing kit C100 reaches a boundary of the insertion unit C310 of the main body C300, the second sensor C354 may provide a signal with respect to the injection of the specimen.

That is, the injection of the specimen through a specimen putting unit C400 may be performed after the specimen analyzing kit C100 is stably fixed to the insertion unit C310 of the main body C300. Here, a signal may be provided by the second sensor C354.

In this case, a message for informing the injection of the specimen may be displayed on the display part C340. Then, the user may inject the specimen to be analyzed into the specimen analyzing kit C100.

Figure 35:
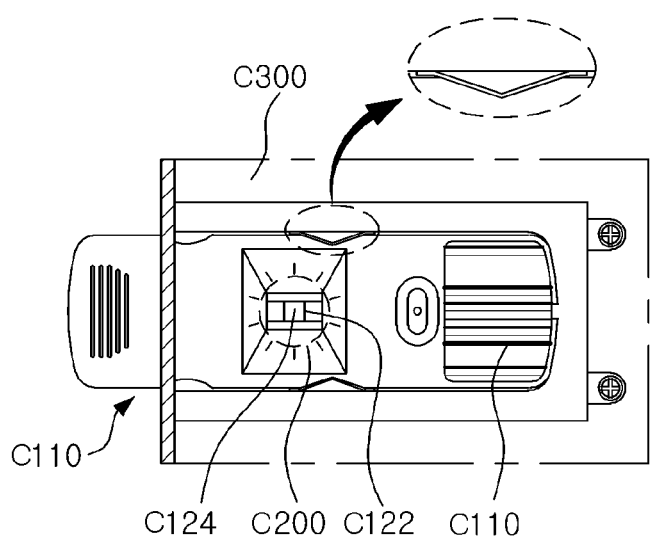

Referring to FIG. 35, the image photographing unit C200 may repeatedly photograph the reaction area C124, i.e., continuously photograph the specimen reaction result C122 at a predetermined time interval when the specimen is completely injected into the specimen analyzing kit C100.

Here, the photographed image may be read together with the image of the identification code by the control unit C320. The read result of the specimen reaction result C122 may be processed by using the read result of the identification code C110 through the control unit C320.

The photographing number of image photographing unit C200 may not be limited, and thus, may be variously set adequate for user's intension.

Here, even though the image photographing unit C200 successively photographs the reaction area C124 at a predetermined time interval, if an accurate analysis result is concluded from the image photographed in the middle, the operation of the image photographing unit C200 may be stopped.

That is, even though the specimen reaction result is clearly concluded after a predetermined time passes according to a property of the reaction pad C120, the clear result may be obtained according to health condition of the specimen subject before the predetermined time passes.

Thus, since the control unit C320 may control the display part 340 to display the analyzed result before the predetermined time passes if the clear result is obtained on the basis of the repeatedly photographed images by the image photographing unit C200.

Ninth Embodiment

Figure 36:
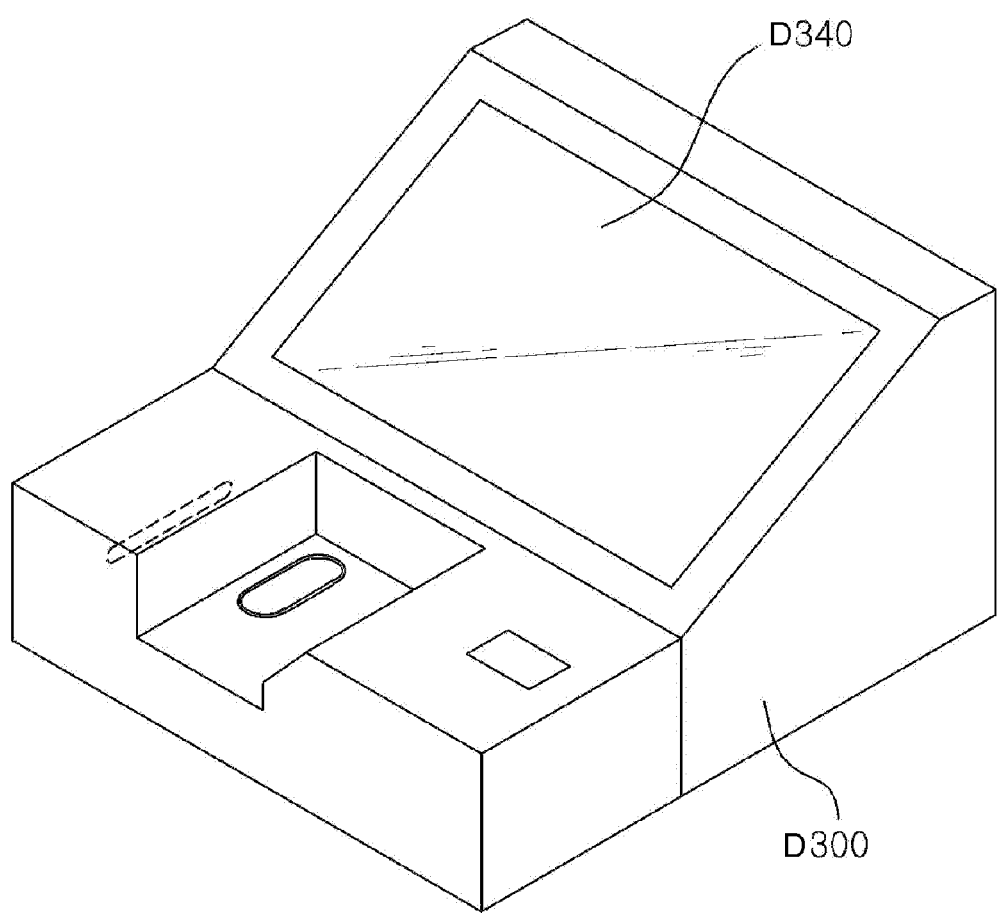
FIG. 36 is a schematic perspective view of a specimen analysis apparatus according to a ninth embodiment of the present invention.
Figure 37:
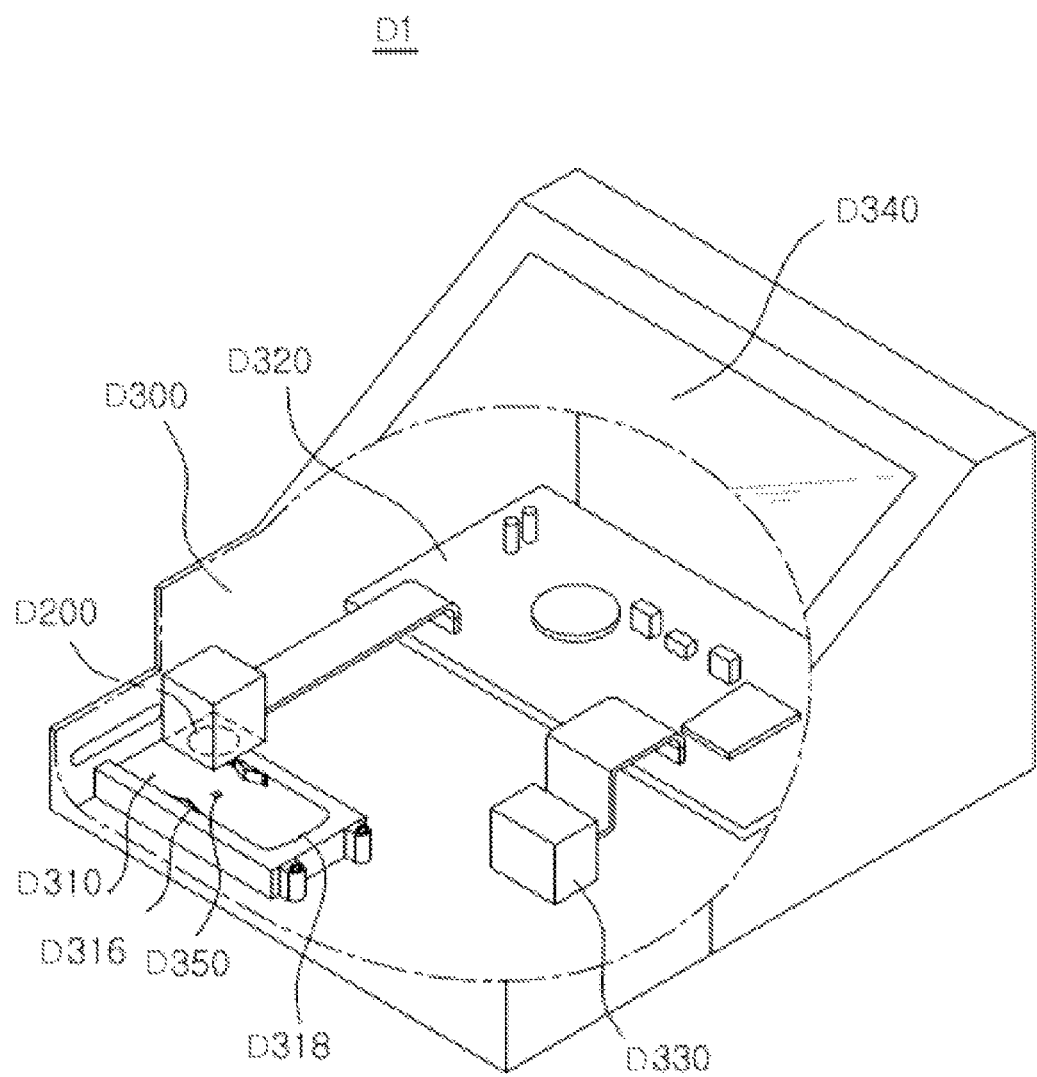
FIG. 37 is a schematic cutoff perspective view of the specimen analysis apparatus according to the eighth embodiment of the present invention.

FIG. 36 is a schematic perspective view of a specimen analysis apparatus according to a ninth embodiment of the present invention, and FIG. 37 is a schematic cutoff perspective view of the specimen analysis apparatus according to the eighth embodiment of the present invention.

Referring to FIGS. 36 to 37, a specimen analysis apparatus D1 according to a ninth embodiment of the present invention may include an image photographing unit D200 for photographing a specimen analyzing kit D100, a sensor unit D350 for detecting a position of the specimen analyzing kit D100, a storage unit D330, a display part D340, and a control unit D320.

The image photographing unit D200, the sensor unit D350, the storage unit D330, the display part D340, and the control unit D320 may be disposed in a main body D300 defining an outer appearance of the specimen analysis apparatus D1. The main body D300 may be variously changed in shape according to user's intension.

The image photographing unit D200 may be disposed on a side (for example, an upper side) of an insertion unit D310 of the main body D300. The insertion unit D310 may be a position at which the specimen analyzing kit D100 is inserted and mounted. The image photographing unit D200 may include various kinds of cameras. The image photographing unit D200 may photograph an identification code D110 and a specimen reaction result D122 which are provided on the specimen analyzing kit D100.

Here, the identification code D110 photographed by the image photographing unit D200 may means information including a separate code value required to obtain effective information about the specimen reaction result D122.

Here, the specimen reaction result D122 may represent a result reacting by moving the specimen, which is injected into the specimen analyzing kit D100, into a reaction area D124 of a reaction pad D120 provided inside the specimen analyzing kit D100. The specimen reaction result D122 and the identification code D110 will be described later in more detail.

Here, the image photographing unit D200 may photograph the identification code D1 and the specimen reaction result D122 in the reaction area D124 with a time difference. For example, the image photographing unit D200 may photograph the identification code D110 and the specimen reaction result D122 in the reaction area D124 according a change in position due to the movement of the specimen analyzing kit D100. Then, the image photographing unit D200 may be configured to conclude an analyzed result of the specimen on the basis of the photographed image.

The storage unit D330 may store program for operating the control unit D320. Also, the storage unit D330 may temperedly store input/output data. Information with respect to the identification code D110 of a plurality of specimen analyzing kits D100 may be stored in the storage unit D330.

The storage unit D330 may include at least one type storage medium of a flash memory type, hard disk type, multimedia card micro type, card type memory (for example, an SD or XD memory), a random access memory (RAM), a static random access memory (SRAM), a read-only memory (ROM), an electrically erasable programmable read-only memory (EEPROM), a programmable read-only memory (PROM), a magnetic memory, a magnetic disk, and an optical disk.

The display part D340 may display information processed in the specimen analysis apparatus D1. For example, the display part D340 may display a user interface (UI) or a graphic user interface (GUI) which relate to the specimen analysis apparatus D1. The display part D340 may include at least one of a liquid crystal display, a thin film transistor-liquid crystal display, an organic light-emitting dido, a flexible display, and a 3D display. Also, the display part D340 may include a transparent or optical transmission type display. This may be called a transparent display. Reprehensive examples of the transparent display may include transparent LCDs. The display part D340 may have a optical transmission type back structure.

For example, at least two display parts D340 may be provided according to an implemented configuration of the specimen analysis apparatus D1. For example, a plurality of display parts D340 may be disposed on one surface of the specimen analysis apparatus D1 so that the plurality of display parts D340 are spaced apart from each other or integrated with each other. Alternatively, the plurality of display parts D340 may be disposed on different surfaces, respectively.

When a sensor for detecting a touch operation with the display part D340 has a layered structure (hereinafter, referred to as a "touch screen"), the display part D340 may be used as an input unit in addition to the output unit. For example, the touch sensor may include a touch film, touch sheet, or touch pad shape.

The touch sensor may be configured to convert a change in pressure applied to a specific portion of the display part D340 or an capacitance generated in a specific portion of the display part D340 into an electrical input signal. The touch sensor may be configured to detect a touched position and area and a pressure when touched.

When a touch input occurs on the touch sensor, a signal corresponding to the touch input may be transmitted into a touch controller. The touch controller may process the signal and then transmit the corresponding data into the control unit D180. Thus, the control unit D180 may recognize a touched area of the display part D340.

The sensor unit D350 senses a position on which the specimen analyzing kit D100 is placed within the specimen analysis apparatus D1. For example, as shown in FIG. 2, the specimen analyzing kit D100 may be mounted on the insertion unit D310 of the main body D300. The sensor unit D350 may sense whether the specimen analyzing kit D100 is completely inserted into the insertion unit D310 or is inserted up to a specific position. Particularly, the sensor unit D350 may be designed to sense whether the specimen analyzing kit D100 is mounted at a first position or a second position of the insertion unit D310. Here, the first position may represent a position at which the image photographing unit D200 can photograph the identification code D110 of the specimen analyzing kit D100, and the second position may represent a position at which the image photographing unit D200 can photograph the reaction area D124 of the specimen analyzing kit D100. The sensor unit D350 may be configured to sense a position of the specimen analyzing kit D100 through various methods. The implemented example of the sensor unit D350 will be described later in detail.

As described above, the control unit D320 may control operations of the specimen analysis apparatus D1 and also control an overall operation of the specimen analysis apparatus D1.

Figure 38:
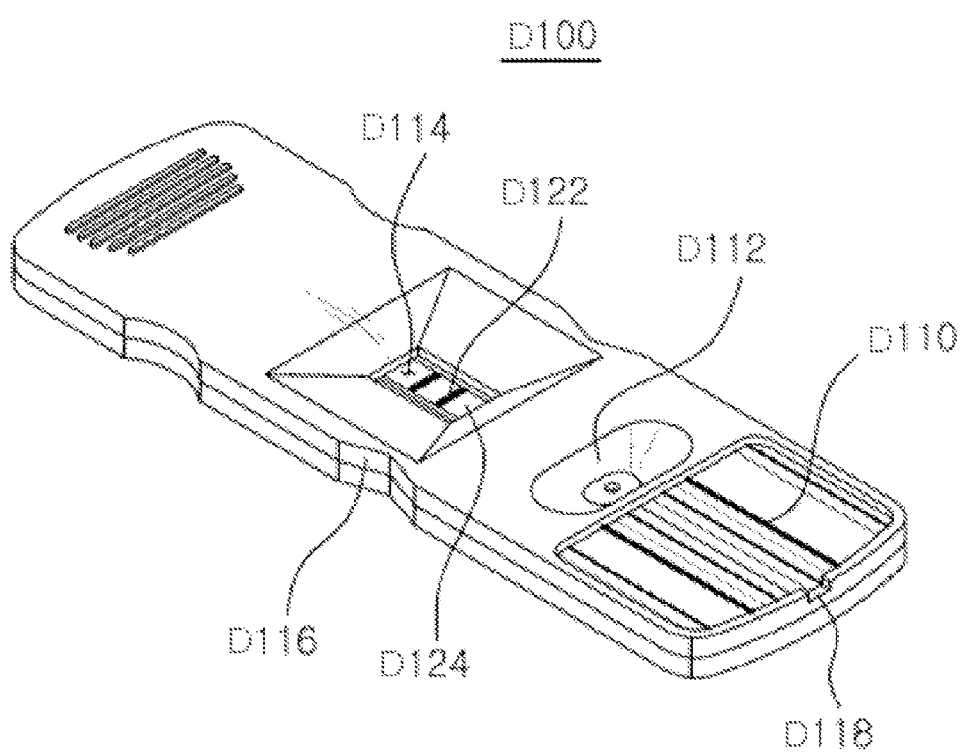
FIG. 38 is a schematic perspective view of a kit for specimen analyzing that is an object to be analyzed by the specimen analysis apparatus according to the eighth embodiment of the present invention.
Figure 39:
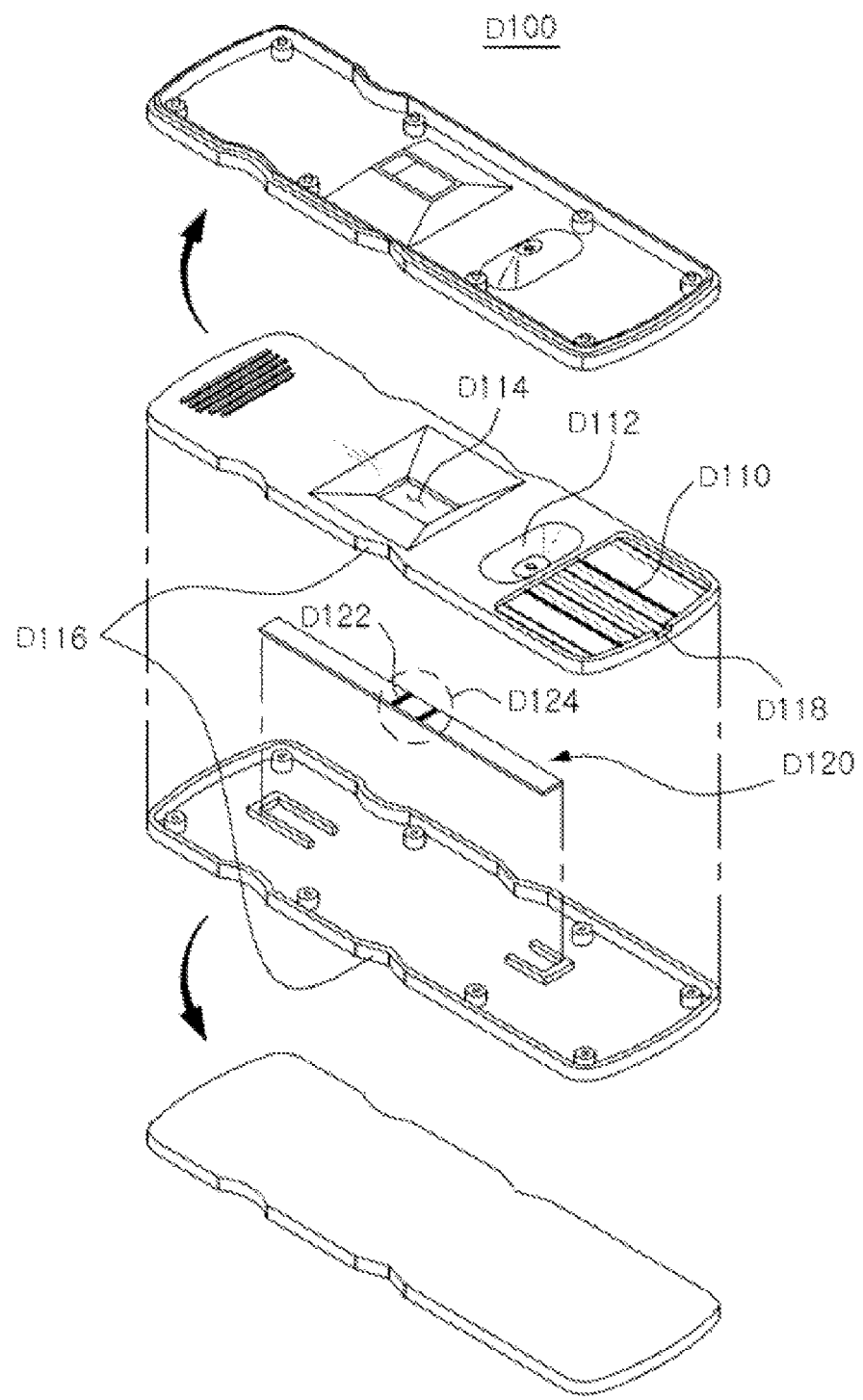
FIG. 39 is a schematic exploded perspective view of the kit for specimen analyzing that is the object to be analyzed by the specimen analysis apparatus according to the ninth embodiment of the present invention.

FIG. 38 is a schematic perspective view of a kit for specimen analyzing that is an object to be analyzed by the specimen analysis apparatus according to the eighth embodiment of the present invention, and FIG. 39 is a schematic exploded perspective view of the kit for specimen analyzing that is the object to be analyzed by the specimen analysis apparatus according to the ninth embodiment of the present invention.

The specimen analyzing kit D100 according to the present invention may analyze a specimen such as blood of a subject to be checked in health conditions. The specimen analyzing kit D100 may include an identification code D110, a put-in part D112, a reaction pad D120, and a result exposing part D114 disposed on the reaction area D124 that is a portion of the reaction pad D120 to expose the reaction area D124 so that the reaction area D124 is visually photographed.

The specimen collected from blood of the subject may be injected through the put-in hole of the put-in part D112.

The specimen injected through the put-in hole of the put-in part D112 may move into the reaction area D124 of the reaction pad D120 after a predetermined time passes to perform predetermined reaction. Alternatively, the specimen injected through the put-in hole of the put-in part D112 may perform predetermined reaction while moving into the reaction area D124 of the reaction pad D120. A reaction reagent may be contained in the reaction area D124 or a portion of the reaction area D124 so that the target specimen to be analyzed through the specimen analysis apparatus D1 and the specimen analyzing kit D100 is smoothly detected.

Thus, while or after the specimen moves into the reaction area D124, the specimen may react. Here, a result of the reaction area D124 may be called a specimen reaction result D122. In more detail, the reaction area D124 may be changed in color by a flow rate difference due to a concentration of an analysis material contained in the specimen. That is, the changed color in the reaction area D124 may be the specimen reaction result D122.

Here, at least one band may be formed as the specimen reaction result D122 on the reaction area D124 according to the result of the above-described reaction. The specimen analysis apparatus D1 may analyze the specimen reaction result D122, i.e., the at least one band to analyze the health conditions of the collected specimen of the subject. Here, a band formation rate, a color of the band, and a position of the band within the reaction area D124 may be analyzed to analyze the health conductions of the subject.

The specimen analysis apparatus D1 according to the ninth embodiment of the present invention may analyze the specimen reaction result D122 by using the image photographing unit D200 such as a camera. Thus, the reaction area D124 of the reaction pad D120 may be exposed to the outside so that the reaction area D124 is visually distinguished by the subject and/or the image photographing unit D200. As described above, a portion exposed for visually observing the reaction area D124 may be defined as the result exposing part D114. Here, the result exposing part D114 may expose the reaction area D124 so that light corresponding to a region of visible rays that is visible by an eye of the human is transmitted. Also, the result exposing part D114 may include a component formed of a transparent material to protect the reaction area D124 and/or the reaction reagent that is capable of being applied to the reaction area D124. That is, the result exposing part D114 may include a protection member such as glass or transparent plastic.

The specimen analyzing kit D100 may include the identification code D110. The identification code D110 may include proper information with respect to the specimen analyzing kit D100.

For example, the identification code D110 may be manufacturing lot information with respect to the specimen analyzing kit D100 according to the present invention.

For another example, the identification code D110 may be an expire data of the specimen analyzing kit D100.

Information recorded in the identification code D110 may be used for analyzing the health conditions by using the specimen reaction result D122.

For example, the result of analyzing the health conditions through the specimen reaction result D122 may be changed. That is, even though the specimen reaction results D122 that are visually distinguished from each other are the same, the analyzed results with respect to the health conditions may be changed according to the information recorded in the identification code D110. In more detail, when the manufacturing lot information is recorded in the identification code D110, the manufacturing lot information may be used to calibrate a result of reading the specimen reaction result. Here, the specimen analyzing kit D100 may be changed in characteristic according to a process condition when the specimen analyzing kit D100 is produced. The specimen analysis may calibrate the specimen reaction result by using the manufacturing lot information so that the specimen reaction result D122 is more accurately read through the specimen analyzing kit D100 that may be changed in characteristic.

Also, the information recorded in the identification code D110 may be used to determine whether the specimen analyzing kit D100 is used. For example, when the identification code D110 includes the expire data, whether the specimen analyzing kit D100 is used may be determined according to the expire data.

The identification code D110 may be photographed by the image photographing unit D200. Thus, the identification information recorded in the identification code D110 may be read by the specimen analysis apparatus D1.

To allow the specimen analysis apparatus D1 to analyze the reaction area of the specimen analyzing kit D100, thereby analyzing the health conditions of the subject, the specimen analyzing kit D100 may be inserted into the specimen analysis apparatus 1. Thus, the user of the specimen analysis apparatus D1 may insert the specimen analyzing kit D100 into the insertion unit D310. However, it should not be necessary to insert the specimen analyzing kit D100 into the specimen analysis apparatus D1 by the person. For example, the specimen analyzing kit D100 may be inserted into the specimen analysis apparatus D1 by an automatic machine.

Although not shown, the specimen analyzing kit D100 may include at least two reaction pads D120. That is, although the specimen analyzing kit D100 includes one reaction pad D120 in FIG. 38, the specimen analyzing kit D100 may include at least two reaction pads D120. Here, reagents for analyzing specimens different from each other may be respectively contained in the reaction pads D120. When the reaction pad D120 is provided in plurality, the reaction areas D124 respectively disposed on the reaction pads D120 may be exposed to the result exposing part D114. Thus, the plurality of specimens may be detected by using one specimen analyzing kit D100.

Hereinafter, a method of controlling the specimen analysis apparatus according to the ninth embodiment of the present will be described.

Hereinafter, for convenience of description, a method of controlling the specimen analysis apparatus by using the specimen analysis apparatus D1 described with reference to FIGS. 36 and 37 and the specimen analyzing kit D100 described with reference to FIGS. 38 and 39 was described. However, the present invention is not limited to the method of controlling the specimen analysis apparatus by using the specimen analysis apparatus D1 and the specimen analyzing kit D100. For example, the method of controlling the specimen analysis apparatus may be realized by using a specimen analysis apparatus and a specimen analyzing kit which are partially different in an outer configuration and/or inner configuration from the specimen analysis apparatus D1 and the specimen analyzing kit.

Also, for convenience of description, although it is assumed that the specimen analyzing kit D100 is inserted into the specimen analysis apparatus D1 by the person such as the user, the present invention is not limited thereto. For example, as described above, it should not be necessary to insert the specimen analyzing kit D100 into the specimen analysis apparatus D1 by the user.

First, a method of controlling the specimen analysis apparatus according to a first embodiment will be described.

[Method of Controlling Specimen Analysis Apparatus According to First Embodiment]

Figure 40:
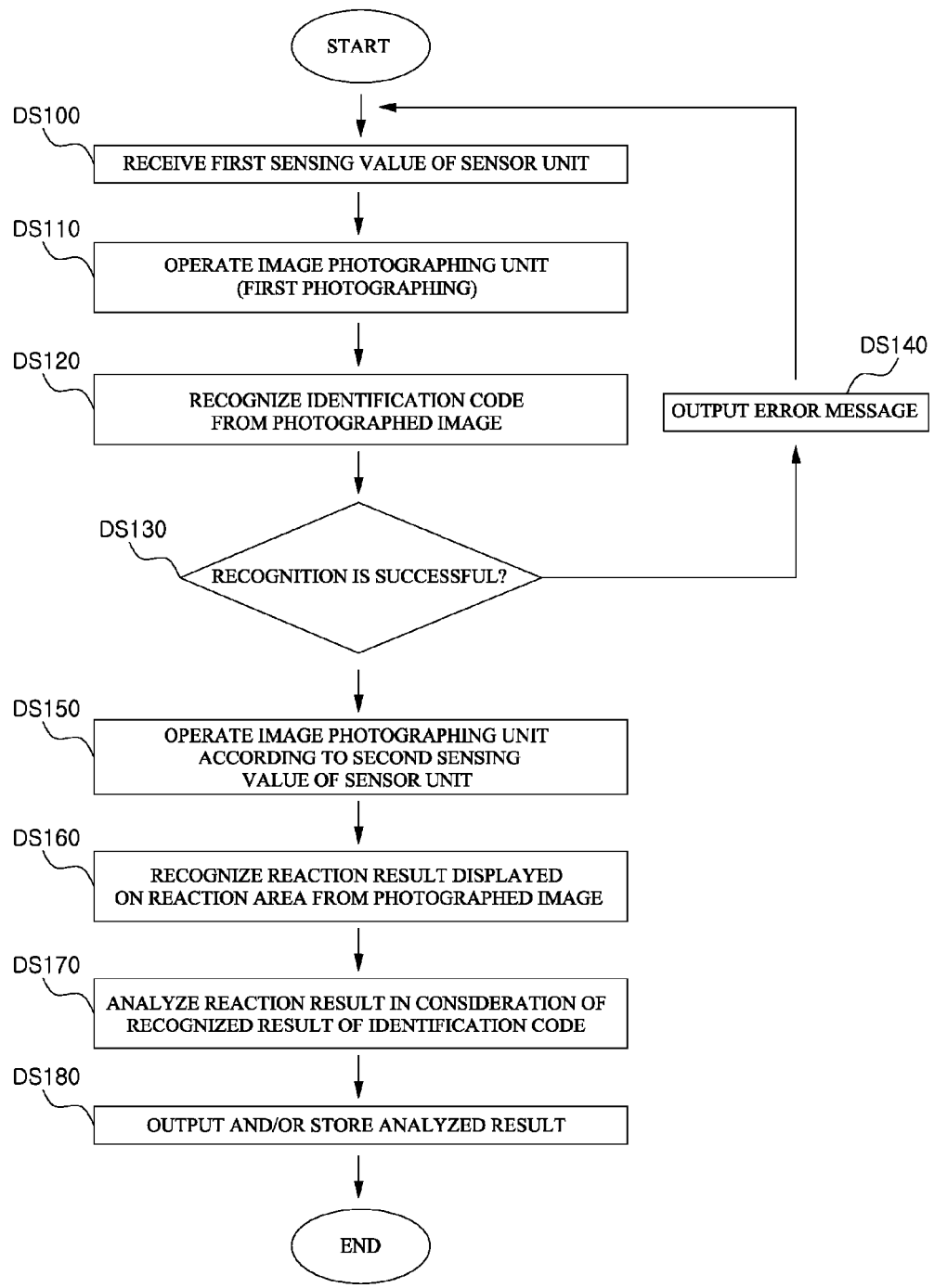
FIG. 40 is a flowchart for explaining the first embodiment in which the specimen analysis apparatus according to the present invention is controlled.

FIG. 40 is a flowchart for explaining the first embodiment in which the specimen analysis apparatus according to the present invention is controlled, and FIGS. 41 to 44 are schematic views illustrating a process in which the specimen analysis apparatus according to the present invention operates according to the first embodiment.

Referring to FIG. 40, the control unit D320 may receive a first sensing value from the sensor unit D350 (DS100). To allow the user to analyze his/her health conditions, the specimen analyzing kit D100 may be inserted into the insertion unit D310 of the specimen analysis apparatus D1.

Figure 41:
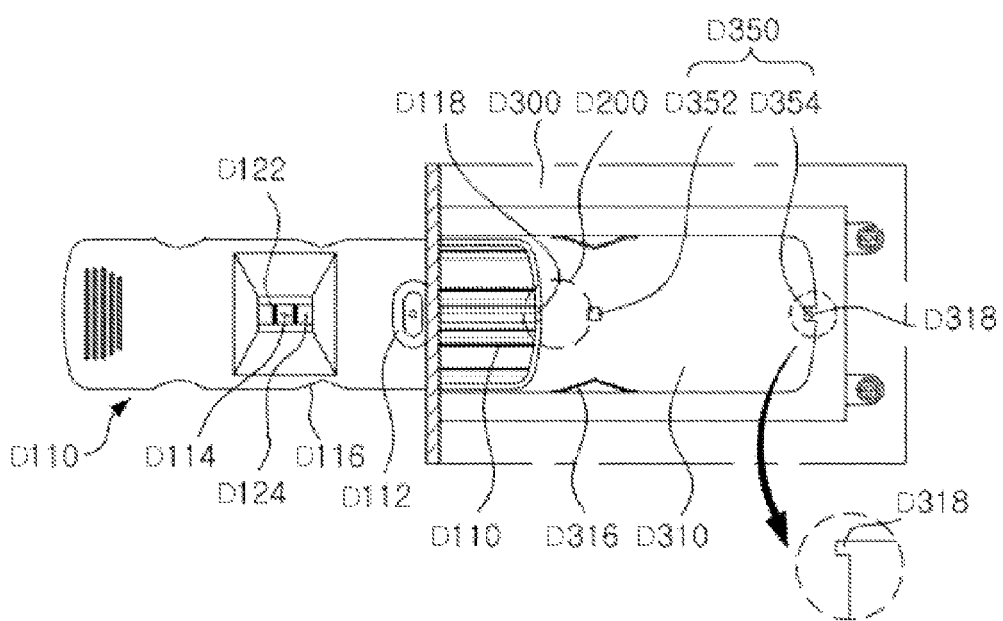
FIGS. 41 to 44 are schematic views illustrating a process in which the specimen analysis apparatus according to the present invention operates according to the first embodiment.
Figure 42:
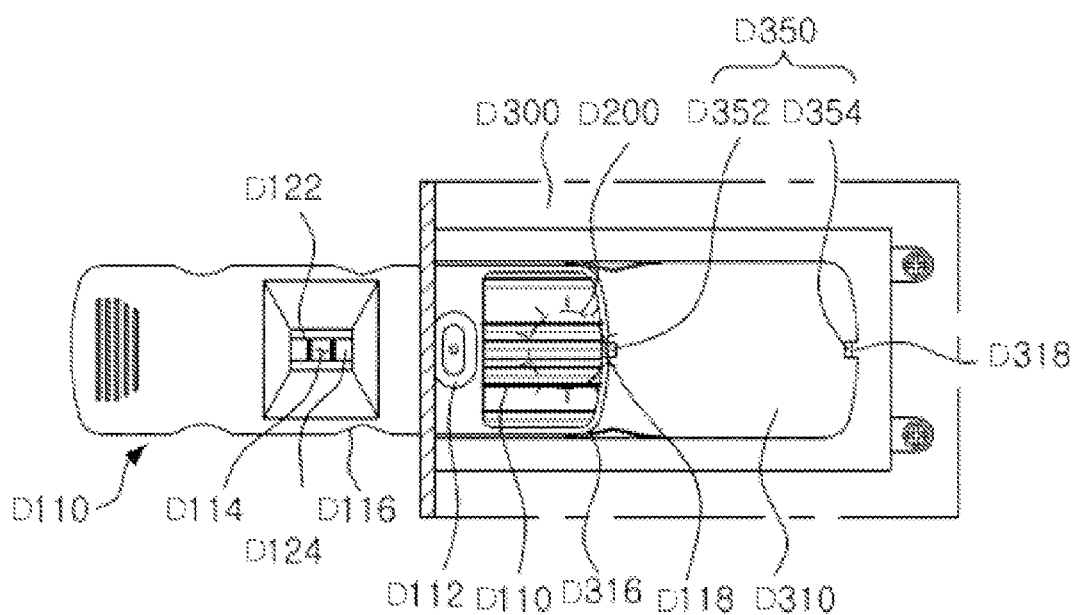

Here, as described above, the sensor unit D350 may sense a degree of the insertion of the specimen analyzing kit D100 into the specimen analysis apparatus D1. When the first sensing value is received from the sensor unit D350, the control unit D320 may determine that the specimen analyzing kit D100 is placed on the first position. For example, as shown in FIG. 41, the specimen analyzing kit D100 is inserted into the insertion unit D310. Then, as shown in FIG. 42, when the specimen analyzing kit D100 is disposed on a position (i.e., the first position) at which the identification code D110 disposed on the specimen analyzing kit D100 is capable of being photographed by the image photographing unit D200, a sensing value may be outputted from one sensor D352 of the sensor unit D350. Thus, the control unit D320 may determine that the specimen analyzing kit D100 is placed on the first position.

The control unit D320 may receive the first sensing value to operate the image photographing unit D200 (DS110). Here, the operating of the image photographing unit D200 may represent the photographing of the image through the image photographing unit D200. Here, the identification code D110 of the specimen analyzing kit D100 may be captured by the image photographing unit D200. Hereinafter, the photographing operation described in the operation DS110 may be called first photographing.

That is, whether the image photographing unit D200 is operated may be determined according to the sensing value of the sensor unit D350 for detecting a change in position due to the movement of the specimen analyzing kit D100. Particularly, according to the present invention, when the first sensing value is outputted from the sensor unit D350, the sensor unit D350 may be designed so that the image photographing unit D200 is operated to accurately photograph the identification code D110.

For example, referring to FIGS. 41 and 42, when the specimen analyzing kit D100 is inserted into the insertion unit D310 of the main body D300, the specimen analyzing kit D100 may include the first sensor D352 so that the first sensing value is provided when the specimen analyzing kit D100 is disposed at a specific position (e.g., the identification code D110 is capable of being photographed by the image photographing unit D200). As shown in FIG. 41, the first sensor D352 may be disposed on one surface of the insertion unit D310, i.e., one surface on which the specimen analyzing kit D100 contacts the insertion unit D310.

As shown in FIG. 42, if an end of the specimen analyzing kit D100 contacts the first sensor D352 as the specimen analyzing kit D100 is inserted into the insertion unit D310, the first sensor D352 may output the first sensing value. Here, the first sensor D352 may be spaced a predetermined distance (e.g., about ½ of a length of the identification code D110) from a position on which the image photographing unit D200 is disposed in the insertion direction of the specimen analyzing kit D100 so that the identification code D110 is accurately photographed by the image photographing unit D200 at a time at which the first sensing value is outputted.

The control unit D320 may operate a light emitting unit (not shown) disposed on the main body D300 before the image photographing unit D200 is operated. The light emitting unit may emit light into the insertion unit D310 on which the specimen analyzing kit D100 is mounted so that an image is well photographed by the image photographing unit D200. The light emitting unit may emit light before the image photographing unit D200 is operated after the first sensing value is received. Alternatively, the light emitting unit may emit light according to an input for starting the above-described operation when the user previously selects the starting of an operation for analyzing the specimen analyzing kit D100 according to a menu screen outputted through the display part D340. The emission operation of the light emitting unit may be finished after the image photographing unit D200 terminates the photographing. Alternatively, the light emitting unit may continuously emit light until operation DS160 is performed to smoothly photograph the reaction area D124 to be photographed in operation DS150.

Then, the control unit D320 may analyze the image of the photographed identification code D110 to recognize the identification code D110 (DS120). The recognition of the identification code D110 may represent that a shape and/or color of the identification code D110 are/is analyzed according to a previous set protocol to extract information encored in the identification code D110.

Then, the control unit D320 may determine whether the identification code D110 is successfully recognized through the operation DS120 (DS130).

Generally, when the specimen analyzing kit D100 is inserted into the insertion unit D310 by the user, a process in which the insertion of the specimen analyzing kit D100 is stopped for a moment when the specimen analyzing kit D100 is disposed at the first position, and then the specimen analyzing kit D100 is fully inserted into the insertion unit D310 is not performed. That is, the user may continuously insert the specimen analyzing kit D100 into the insertion unit D310 until the specimen analyzing kit D100 is fully mounted into the insertion unit D310 without stopping. Here, when the image photographed through the image photographing unit D200 does not include the identification code D110 or includes only a portion of the identification code D110, or the image is blurred, the control unit D320 may not recognize the identification code D110.

When it is determined that the identification code D110 is not normally recognized in operation DS130, the control unit D320 may output an error message to the user through the display part D340 (DS140). Then, the operations DS100 to DS130 may be repeated again. The error message may include contents for requesting the re-insertion of the specimen analyzing kit D100 into the insertion unit D310 to the user. In spite that the error message is outputted to the user in the operation DS140, if the insertion of the specimen analyzing kit D100 is maintained for a predetermined time (i.e., the user does not take the specimen analyzing kit D100 out of the insertion unit D310), the control unit D320 may output the error message again. Here, the control unit D320 may acoustically output the error message to the user through an acoustic output unit (not shown) in addition to the visual output of the error message through the display part D340 to awaken surroundings again.

When it is determined that the identification code D110 is normally recognized in the operation DS130, the control unit D320 may operate the image photographing unit D200 according to a second sensing value outputted from the sensor unit D350 (DS150). Here, the reaction area D124 of the specimen analyzing kit D100 may be captured by the image photographing unit D200. Hereinafter, the photographing operation described in the operation DS110 may be called second photographing.

Figure 43:
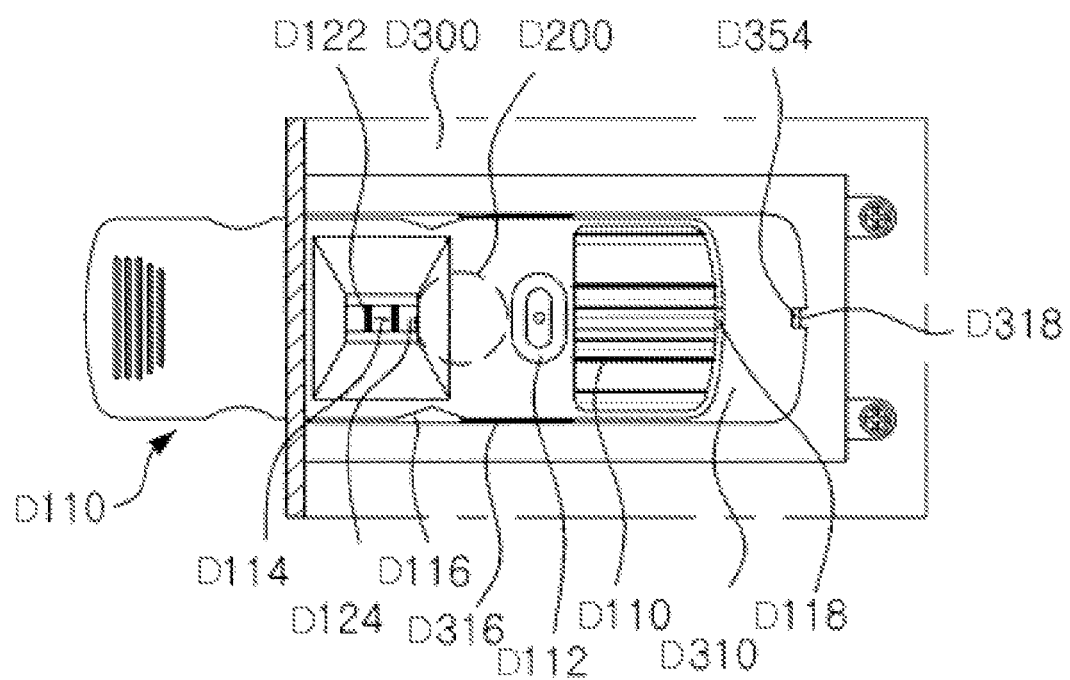
Figure 44:
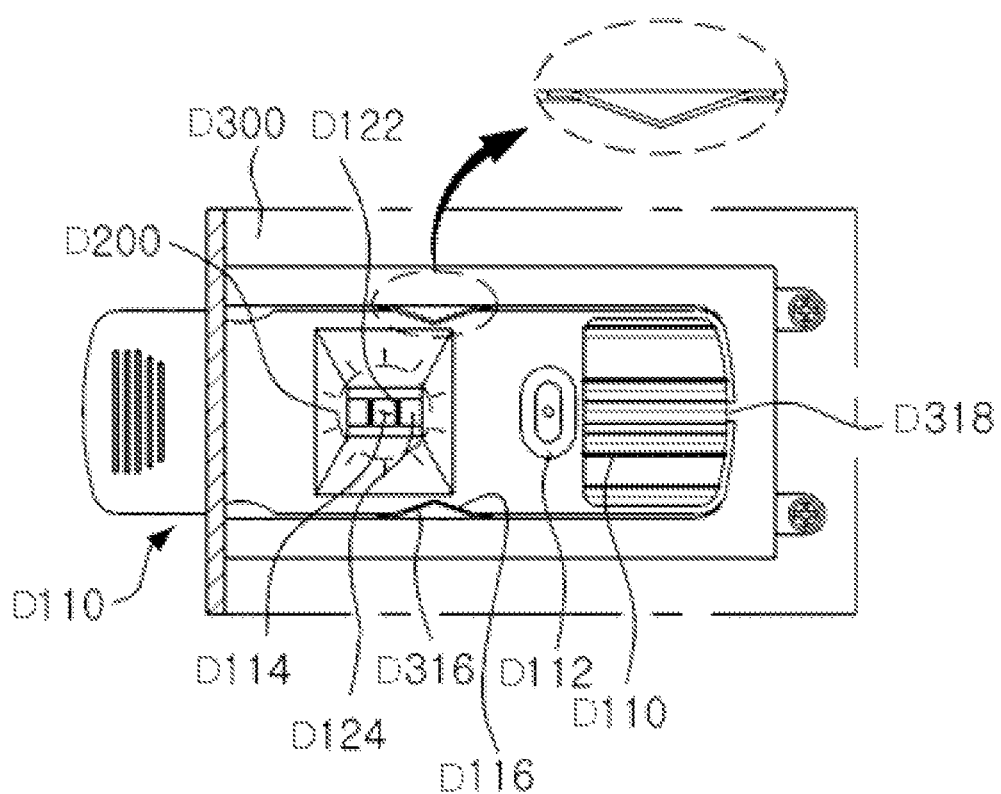

As described above, as the specimen analyzing kit D100 is continuously inserted into the insertion unit D310, as shown in FIGS. 43 and 44, an end of the specimen analyzing kit D100 may contact the second sensor D354. That is, as shown in FIG. 44, when the specimen analyzing kit D100 is fully inserted into the insertion unit D310, the second sensor D354 may output the second sensing value. Thus, the image photographing unit D200 may be operated again according to the second sensing value to photograph the reaction area D124.

Here, an insertion position fixing corresponding part D316 disposed on the main body D300 may be designed to get behind somewhat by an outer appearance of the specimen analyzing kit D100. That is, the insertion position fixing corresponding part D316 may protrude from each of both side surfaces of the insertion unit D310 of the main body D300 and also has elasticity. Thus, while the specimen analyzing kit D100 is inserted, the insertion position fixing corresponding part D316 may get behind by the elasticity until an insertion position fixing part D116 recessed from each of both sides of the specimen analyzing kit D100 reaches a position corresponding to the insertion position fixing corresponding part D316.

As shown in FIG. 44, the insertion position fixing corresponding part D316 may correspond to the insertion position fixing part D116 disposed on the specimen analyzing kit D100. The insertion position fixing corresponding part D316 may be inserted into the insertion position fixing part D116 by a restoring force thereof to stably fix the specimen analyzing kit D100 to the insertion unit D310 of the main body D300.

The specimen analyzing kit D100 may be more stably fixed to the insertion unit D310 of the main body D300 by a vertical movement prevention part D118. This may be realized by inserting the vertical movement prevention corresponding part D318 disposed on a boundary of a space, in which the specimen analyzing kit D100 is inserted, into the vertical movement prevention part D118. That is, the vertical movement prevention part D118 may be disposed to correspond to the vertical movement prevention corresponding part D318. Thus, the vertical movement of the specimen analyzing kit D100 may be prevented by the vertical movement prevention corresponding part D318 inserted into the vertical movement prevention part D118.

Thus, the insertion position fixing corresponding part D316 and vertical movement prevention corresponding part D318 which are disposed on the insertion unit D310 of the main body D300 may be respectively inserted into the insertion position fixing part D116 and the vertical movement prevention part D118 to stably fix the specimen analyzing kit D100 to the inside of the main body D300.

Thus, it may previously prevent the specimen analyzing kit D100 from moving, i.e., peeling off within the main body D300 to realize an accurate specimen analysis.

The control unit D320 may operate the light emitting unit (not shown) before the image photographing unit D200 is operated as described in the operation DS110. If the light emitting operation of the light emitting unit is stopped after the first photographing, the light emitting operation of the light emitting unit may be performed before the second photographing. Here, a trigger with respect to the light emitting operation of the light emitting unit may be the reception of the second sensing value outputted from the sensor unit D350. After the second photographing is performed, the light emitting operation of the light emitting part may be stopped. However, it may not be necessary to stop the light emitting operation of the light emitting unit after the second photographing is performed.

As the first sensing value is received, the second sensing value may be received before whether the identification information is successfully recognized is determined on the basis of the identification code D110 acquired in the DS110 (DS130). Here, the specimen analysis apparatus D1 may be controlled as follows.

First, even though the second sensing value is received, the control unit D320 may perform the operation DS150 after whether the identification information is successfully recognized is determined in the operation DS130. That is, the operation DS150 may be performed only when all of the two conditions, i.e., the reception of the second sensing value and the successful recognition of the identification information are satisfied.

Second, when the second sensing value is received, as described above, the control unit D320 may photograph an image with respect to the reaction area D124. That is, when the second sensing value is received, the control unit D320 may perform the operation DS150 before the determination result in the operation DS130 is concluded. When the second sensing value is received, the operation DS150 may be performed regardless of the determination result in the operation DS130. In the determination result in the operation DS130, if it is determined that the identification code D110 is not normally recognized, the control unit D320 may store the photographed image of the reaction area D124 in the storage unit D330. In the case where the photographed image of the reaction area D124 is stored, the control unit D320 may not photograph the reaction area D124 again when the second sensing value outputted as the specimen analyzing kit D100 is inserted again by the user due to the output of the error message is received. Thus, the stored image may be used in operations DS160 and DS170 which are described later.

Then, the control unit D320 may analyze the health conditions of the subject on the basis of the images photographed in the operations DS110 and DS160.

The method of controlling the specimen analysis apparatus D1 according to the first embodiment of the present invention may be a method of analyzing the specimen analyzing kit D100 in which the specimen reaction is completed before the specimen analyzing kit D100 is inserted into the specimen analysis apparatus D1. That is, a method for analyzing the specimen analyzing kit D100 having the specimen reaction result D122 as the specimen is injected into the put-in hole of the put-in part D112, and then the injected specimen moves into the reaction area D124 to cause predetermined reaction for analyzing the specimen may be the method of controlling the specimen analysis apparatus D1 according to the first embodiment of the present invention.

In operation DS170, as described with reference to FIGS. 38 and 39, at least one band formed by analyzing the reaction result D122 of the reaction area D124 may be analyzed to analyze the health conditions of the subject from which the specimen is collected. Here, as described above, a color of the band and a position of the band within the reaction area D124 may be analyzed to analyze the health conductions of the subject.

When the reaction result is analyzed in the operation DS170, as described above, the identification information acquired in the operations DS110 and DS120 may be used. That is, the result analyzed in the operation DS170 may be calibrated by using the manufacturing lot information encored in the identification code D110. Alternatively, whether the inserted specimen analyzing kit D100 is usable may be determined by using the expire data encored in the identification code D110.

When the specimen analyzing kit D100 includes a plurality of reaction pads D120 to analyze multiple specimens, the specimen analysis apparatus D1 may photograph a portion of the reaction areas D124 of the plurality of reaction pads D120 exposed through the result exposing part D140 to analyze the reaction results with respect to the multiple specimens. Here, the specimen analysis apparatus D1 may perform the analysis with respect to the reaction areas D124 of the plurality of reaction pads D120 by photographing the reaction areas D124 once. Of course, the specimen analysis apparatus D1 may perform the photographing several times to analyze each of the reaction results of the reaction pads D120.

Although not shown, if it is determined that the specimen analyzing kit D100 is unusable on the basis of the expir data, specimen analysis apparatus D1 may output a message for informing use of the other specimen analyzing kit D100 to the user.

The control unit D320 may output to the analyzed results so that the user easily confirms its content. Furthermore, the control unit D320 may store the analyzed results in the storage unit D330 so that the analyzed results are used later.

The analyzed results may be visually displayed through the display part D340.

Alternatively, the analyzed results may be acoustically outputted through the acoustic output unit (not shown).

Alternatively, the analyzed results may be ractually outputted through a vibration output unit (not shown). The vibration output unit (not shown) may be a component for generating vibration so that the user feels the vibration. Here, the vibration output unit may inform the analyzed results of the health conditions to the user by using an output state of the vibration.

The control unit D320 may select a time taken for the specimen analysis. For example, the control unit D320 may select a time taken for the specimen analysis on the basis of the recognized result of the identification code. That is, the control unit D320 may determine the time taken for the specimen analysis, for example, five minutes or ten minutes. For another example, the control unit D320 may receive a time taken for the specimen analysis from the user to select the inputted value as a time taken for the specimen analysis. That is, when the user inputs five minutes as the time taken for specimen analysis, the control unit D320 may select the five minutes inputted by the user as the time taken for the specimen analysis. Here, the control unit D320 may provide a user interface so that the user easily selects the time taken for the specimen analysis.

As described above, when the time taken for specimen analysis is selected, the control unit D320 may output an alarm to the user after the time taken for specimen analysis passes. For example, before the operation DS180 is performed, or while the operation DS180 is performed, the control unit D320 may output the alarm to the user.

According to the method of controlling specimen analysis apparatus D1 according to the first embodiment of the present invention, the identification code D110 and the specimen reaction result of the specimen analyzing kit D100 on which the specimen reaction result D122 is displayed may be photographed with a time difference. Here, it may be unnecessary to provide a plurality of image photographing units for photographing each of the identification code D110 and the specimen reaction result D122. That is, all of the identification code D110 and the specimen reaction result D122 may be photographed by only one image photographing unit D200.

Thus, since the specimen analysis apparatus D1 according to the present invention may realize accurate analysis of the specimen through the singular image photographing unit D200, the specimen analysis apparatus D1 may be miniaturized and simplified.

Hereinafter, a method of controlling the specimen analysis apparatus D1 according to a second embodiment will be described.

[Method of Controlling Specimen Analysis Apparatus According to Second Embodiment]

Figure 45:
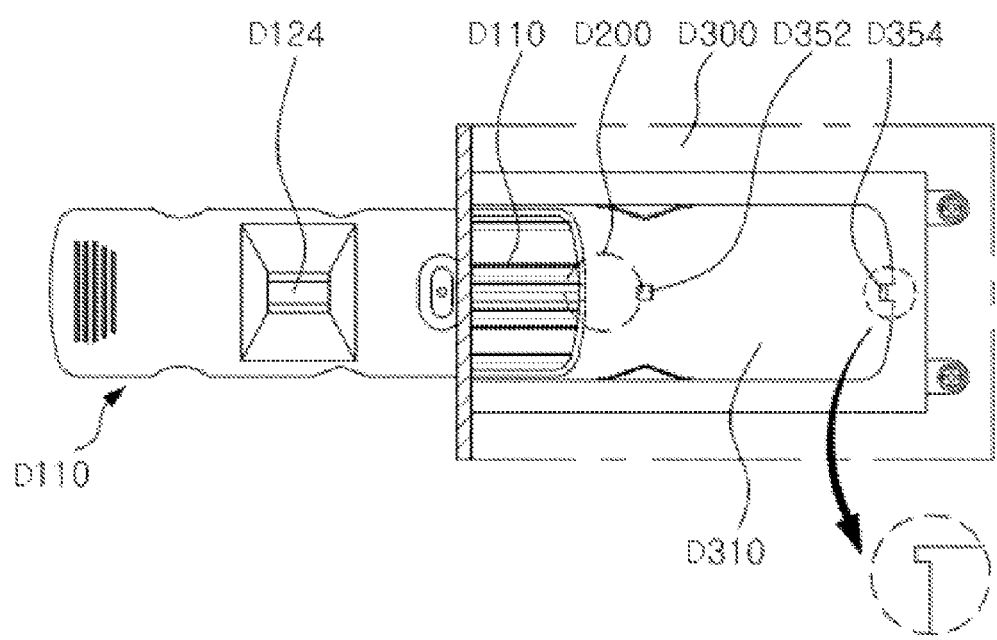
FIG. 45 is a flowchart for explaining the second embodiment in which the specimen analysis apparatus according to the present invention is controlled.
Figure 46:
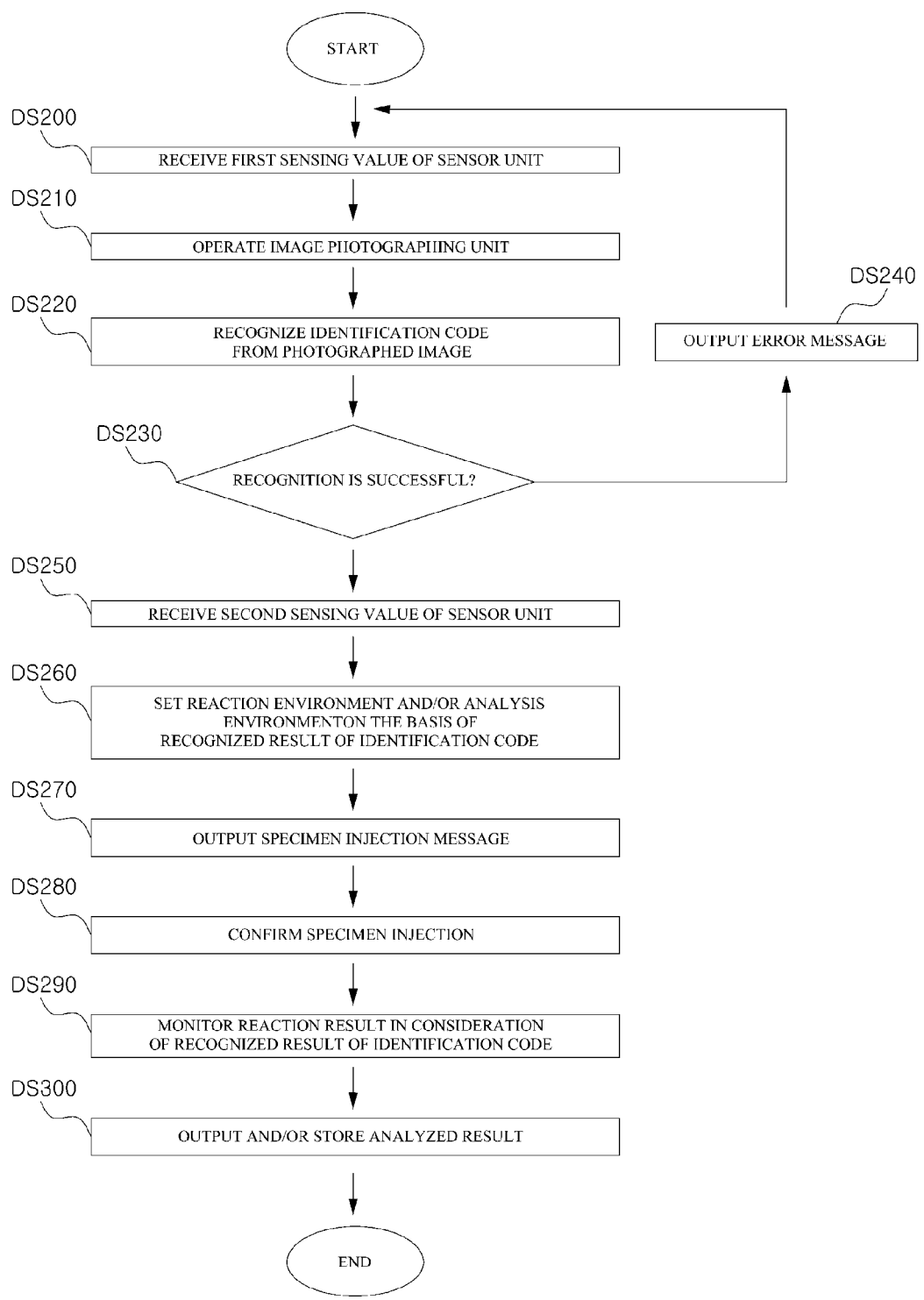
FIGS. 46 to 51 are schematic views illustrating a process in which the specimen analysis apparatus according to the present invention operates according to the second embodiment.
Figure 47:
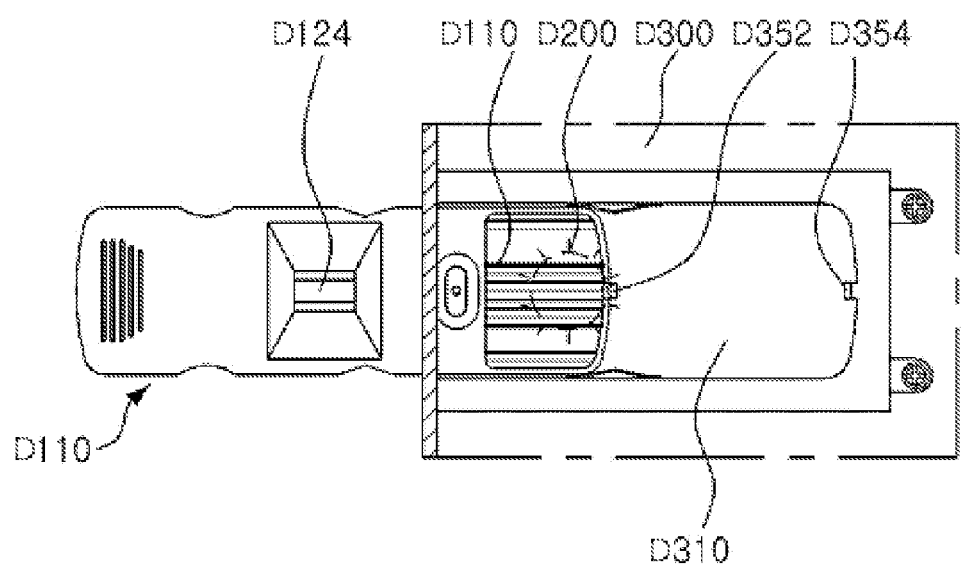
Figure 48:
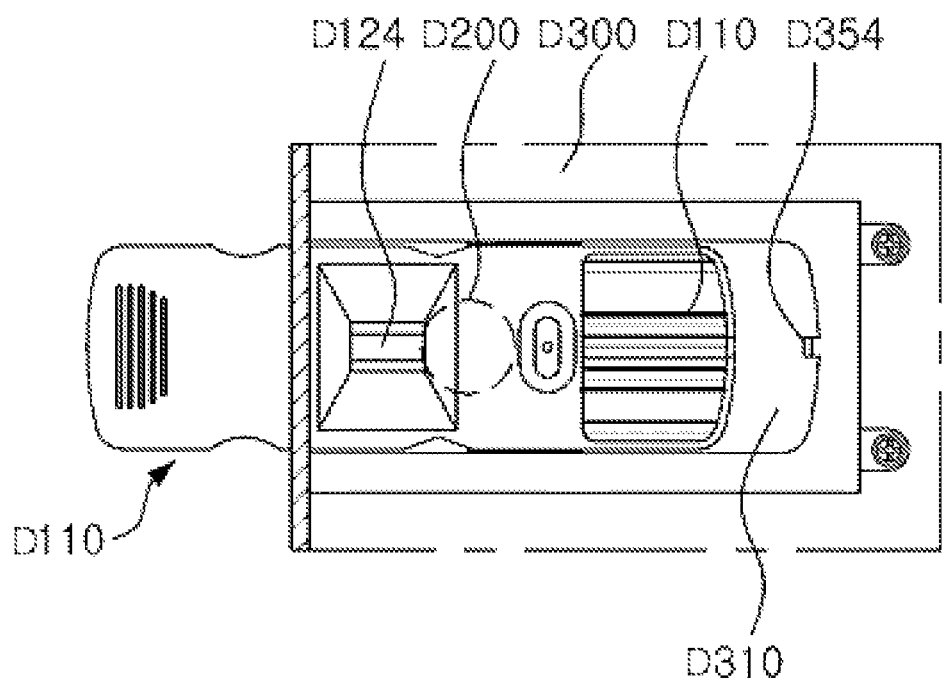

FIG. 45 is a flowchart for explaining the second embodiment in which the specimen analysis apparatus according to the present invention is controlled, and FIGS. 46 to 51 are schematic views illustrating a process in which the specimen analysis apparatus according to the present invention operates according to the second embodiment.

Referring to FIG. 45, a method of controlling specimen analysis apparatus D1 according to the second embodiment of the present invention may include a process (DS200) of receiving a first sensing value of a sensing unit D350, a process (DS210) of operating an image photographing unit D200, a process (DS220) of recognizing an identification code D110 from a photographed image, a process (DS230) of determining whether the identification code D110 is successfully recognized, and a process (D240) of outputting an error message when the recognition fails. Here, since the operations DS200 to DS240 are equal or similar to the operations DS100 to DS140 according to the first embodiment, their detailed descriptions will be omitted.

Figure 49:
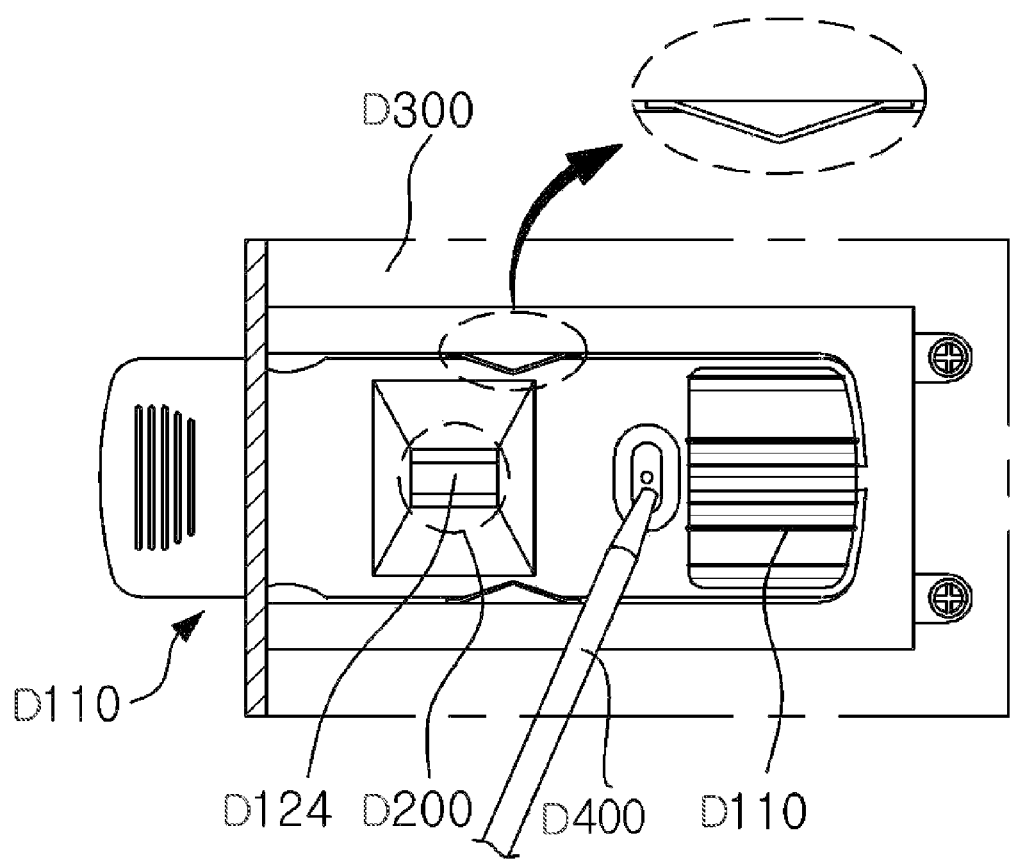

According to the determination result in operation DS230, if it is determined that the recognition is successful, a control unit D320 may receive a second sensing value from a sensor unit D350 (DS250). For example, as shown in FIG. 49, when a specimen analyzing kit D100 is fully inserted into an insertion unit D310, the second sensing value may be received from a second sensor D354.

Then, a control unit D320 may set reaction environments and/or analysis environments which well cause predetermined reaction for analyzing health conditions of a subject by putting a specimen into a specimen analyzing kit D100, on the basis of a recognized result of an identification code D110 photographed in the operations DS210 and DS220.

For example, a kind of target specimen to be analyzed by using the inserted specimen analyzing kit D100 may be confirmed according to the result recognized from the identification code D110. Also, a reaction time of the inserted specimen analyzing kit D100 may be set. For example, when a kind of target specimen to be analyzed by using the specimen analyzing kit D100 is A, a time taken until a specimen reaction result is concluded may be about five minutes. When a kind of target specimen is B, a time taken until a specimen reaction result is concluded may be about ten minutes. Thus, the specimen analysis apparatus D1 may confirm the target specimen of the specimen analyzing kit D100 by using the identification code D110 and set an adequate reaction time of the target specimen.

For another example, the specimen analysis apparatus D1 may confirm a kind of specimen analyzing kit D100 inserted through the identification code D100 and set a temperature adequate for predetermined reaction to be generated in the specimen analyzing kit D100. That is, there is a temperature adequate for generating the predetermined reaction in a reaction area D124 by injecting the specimen. Thus, the control unit D320 may set the adequate temperature. Although not shown, the specimen analysis apparatus D1 may include a temperature adjustment device in the vicinity of the insertion unit D310 in which the specimen analyzing kit D100 is inserted so that the insertion unit D310 and/or the specimen analyzing kit D100 are maintained at the set temperature. For example, the temperature adjustment device may be a device such as a heater for providing heat to the insertion unit D310 and/or the specimen analyzing kit D100. For another example, the temperature adjustment device may be a device such as a cooler for releasing heat from the insertion unit D310 and/or the specimen analyzing kit D100.

As described above, when the reaction environments and/or analysis environments are completely set, the control unit D320 may output a message for requesting that a specimen is injected through a put-in hole of a put-in part D112 disposed on the specimen analyzing kit D100 (DS270).

The method of controlling the specimen analysis apparatus D1 according to the second embodiment of the present invention may be a method of continuously monitoring occurrence of the above-described specimen reaction in the specimen analyzing kit D100 and analyzing an analyzed result after the above-described specimen analyzing kit D100 is inserted into the specimen analysis apparatus D1. That is, the method of controlling the specimen analysis apparatus D1 according to the second embodiment of the present invention may be a method of continuously monitoring occurrence of predetermined reaction by injecting the specimen into the put-in hole of the put-in part D112 and analyzing an analyzed result after the specimen analyzing kit D100 is inserted into the specimen analysis apparatus D1.

Figure 50:
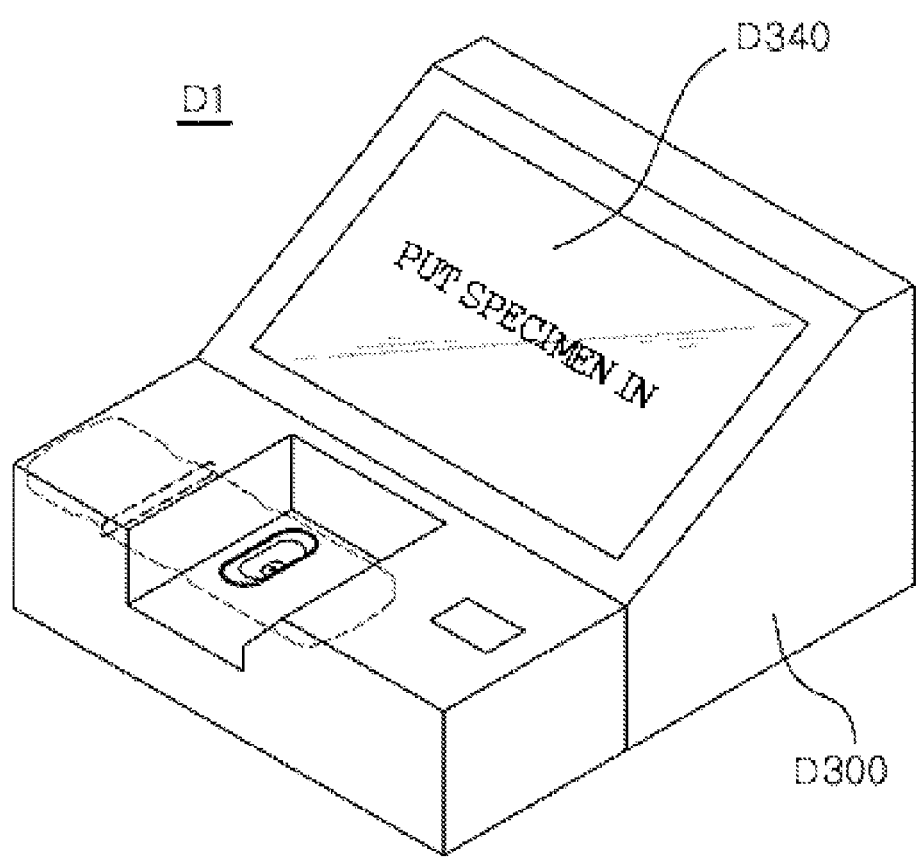

The message outputted in the operation DS270, as shown in FIG. 49, may induce the injection of the specimen of the subject into the specimen analyzing kit D100 by a user. As shown in FIG. 50, the message may be visually outputted through a display part D340 or acoustically outputted through the acoustic output unit (not shown). Alternatively, the message may be ractually outputted through a vibration output unit (not shown).

Thus, the control unit D320 may confirm whether the specimen is normally injected into the put-in hole of the put-in part D112 (DS280). The control unit D320 may confirm whether the specimen is injected through various manners.

For example, when an input for confirming the injection of the specimen by the user is received, the control unit D320 may confirm that the specimen is injected.

For another example, the control unit D320 may actively sense that the specimen is injected into the put-in hole of the put-in part D112 to confirm the injection of the specimen. Here, the control unit D320 may observe a change of the reaction area D124 by using an image photographing unit D200 to determine that the specimen is normally injected. Alternatively, the control unit D320 may confirm whether the specimen is injected by using other sensors (not shown).

Figure 51:
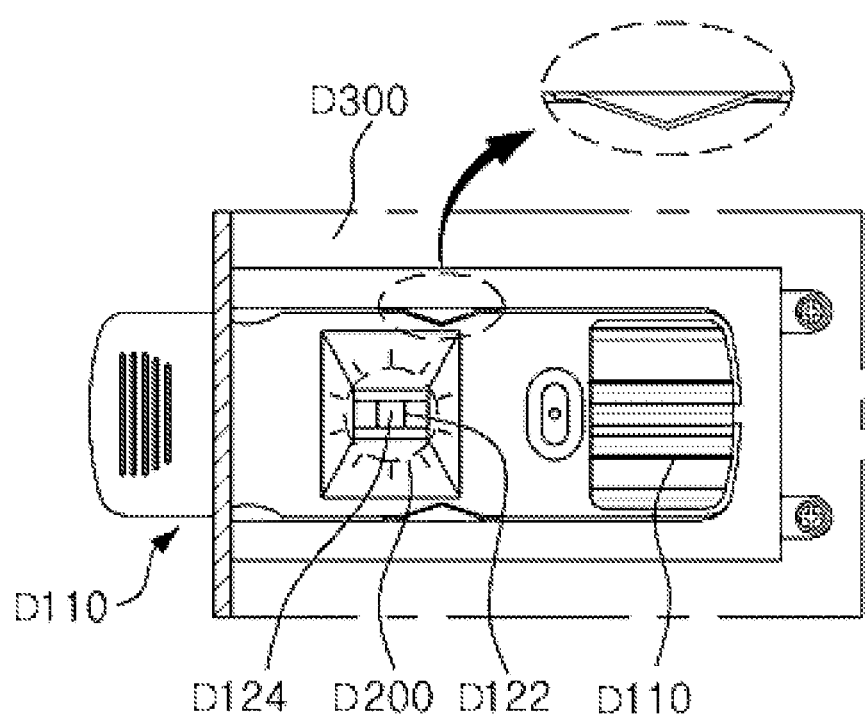

The control unit D320 may monitor the specimen reaction result formed on the reaction area D124 on the basis of the result recognized in the operations DS210 and DS220 (DS290). To perform the operation DS290, the control unit DS320 may continuously and periodically photograph the reaction area D124 by using the photographing unit D200. For example, when the specimen is injected into the put-in hole of the put-in part D112, as described above, the specimen moves into the reaction area D124 through the reaction pad D120, or the specimen may cause predetermined reaction while moving into the reaction area D124. Here, the reaction result, as shown in FIG. 51, may be displayed together with the specimen reaction result D122 in the reaction area D124. The control unit D320 may control the image photographing unit D200 to photograph an image (for example, a stock image) of the reaction area D124 according to a preset period such as 1 second, 10 seconds, and/or 1 minute so that formation of the specimen reaction result in the reaction area D124 is photographed as a moving picture in real-time, or formation of the specimen reaction result is confirmed in time series.

The monitoring operation in operation DS290 may be performed during a reaction time set in the operation DS260. When the reaction time passes, the specimen reaction result formed in the reaction area D124 which is equal or similar to that in the operation DS170 may be analyzed.

It should not be necessary to perform the monitoring operation in the operation DS290 during the reaction time set in the operation DS260. The control unit D320 may perform analysis of the specimen reaction result even before the reaction time passes. For example, when the specimen reaction result formed in the reaction area D124 is determined according a preset standard even before the set reaction time passes, if it is determined that the specimen reaction result is within an abnormal range, the control unit D320 terminates the analysis of the specimen reaction result.

As described above, when the analyzed result is concluded, the control unit D320 may output the analyzed result or store the analyzed result so as to use the analyzed result later (DS300). Since the operation DS300 is equal or similar to the above-described operation DS180, its detailed description will be omitted.

According to the method of controlling the specimen analysis apparatus D1 according to the second embodiment of the present invention, there is an effect that provides an environment adequate for the reaction occurring in the specimen analyzing kit D100 in addition to the effect in the first embodiment.

Also, the reaction result may be continuously monitored even before the predetermined reaction time passes to finish the analysis of the specimen reaction result. Thus, the time taken for analyzing the one specimen analyzing kit D100 may be reduced.

Hereinafter, a method of controlling the specimen analysis apparatus D1 according to a third embodiment will be described.

[Method of Controlling Specimen Analysis Apparatus According to Third Embodiment]

Figure 52:
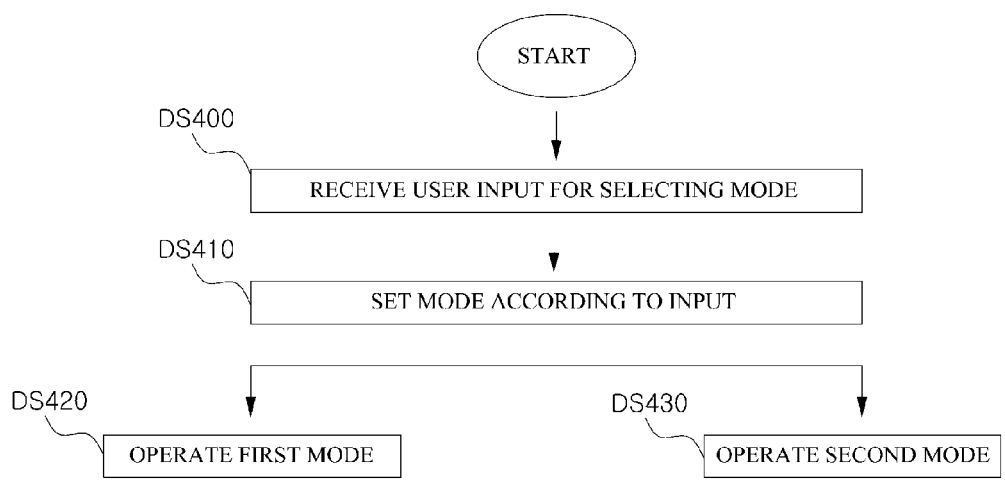
FIG. 52 is a flowchart for explaining the third embodiment in which the specimen analysis apparatus according to the present invention is controlled.
Figure 53:
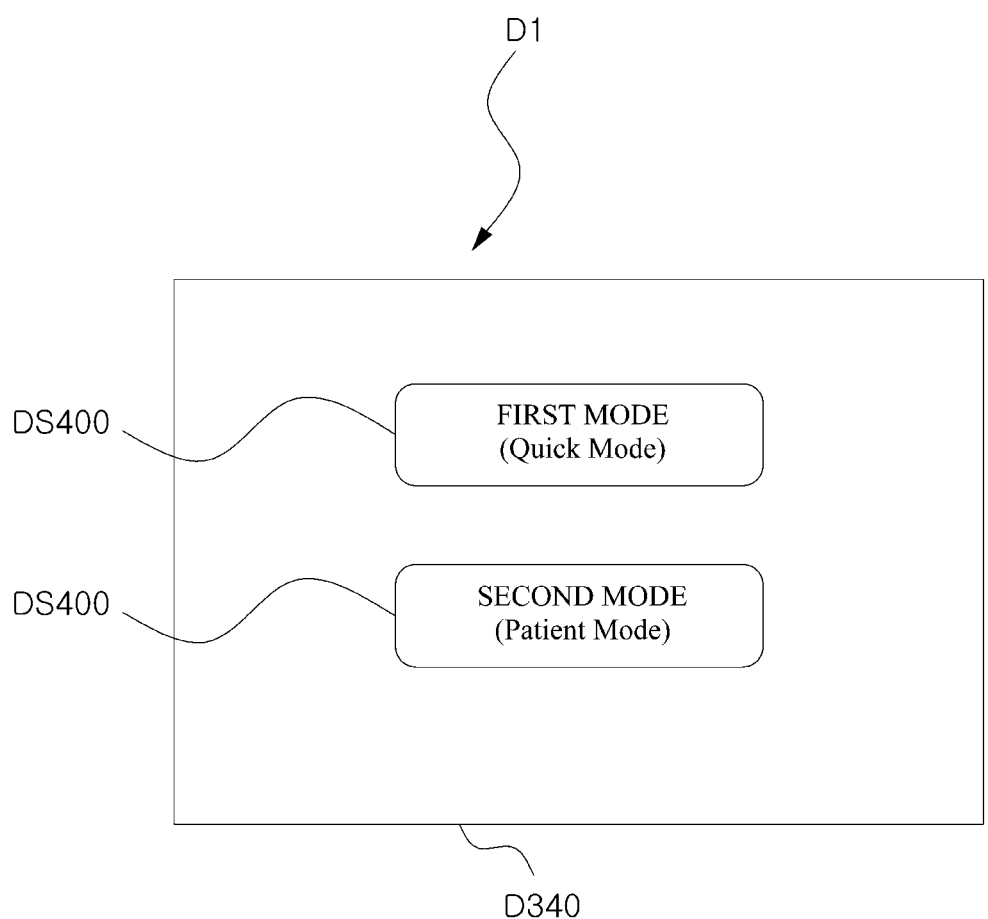
FIG. 53 is a schematic view illustrating a process in which the specimen analysis apparatus according to the present invention operates according to the third embodiment.

FIG. 52 is a flowchart for explaining the third embodiment in which the specimen analysis apparatus according to the present invention is controlled, and FIG. 53 is a schematic view illustrating a process in which the specimen analysis apparatus according to the present invention operates according to the third embodiment.

Referring to FIG. 52, a control unit D320 may receive a user input for selecting a mode from a user (DS400).

The mode may include a first mode and a second mode. The first mode may be a mode in which an already analyzed specimen analyzing kit D100 is inserted to perform analysis. The second mode may be a mode in which a specimen is injected into the specimen analyzing kit D100 after the specimen analyzing kit D100 is inserted into the specimen analysis apparatus D1 to continuously monitor specimen analysis reaction, thereby analyzing the reaction result.

The specimen analysis apparatus D1 may provide a predetermined user interface to a user so as to receive a user input for selecting the above-described mode.

For example, as shown in FIG. 53, a menu item DM1 corresponding to the first mode and a menu item DM2 corresponding to the second mode may be displayed through a display part D340. In a case where the display part D340 is a touch screen, when the menu items DM1 and DM2 corresponding to the first and second modes are touched by using a finger of the user, a mode corresponding to each of the touched menu items DM1 and DM2 may be selected.

The control unit D320 may set the specimen analysis apparatus D1 so that the specimen analysis apparatus D1 is operated according to the mode selected in the operation DS400 (DS410).

For example, the specimen analysis apparatus D1 may include various modules necessary for operating the specimen analysis apparatus D1 in addition to the above-described various components. Thus, the components necessary for operating the specimen analysis apparatus D1 and/or the modules may be activated or operated immediately according to the selected mode.

For another example, an operation algorithm of the specimen analysis apparatus D1 for normally operating the specimen analysis apparatus D1 according to the above-described respective modes may be different in the first and second modes. When one mode is selected in the operation DS400, the control unit D320 may load the operation algorithm corresponding to the selected mode.

The above-described operation may be performed to adequately operate the specimen analysis apparatus D1 according to the selected mode.

If the first mode is selected, the specimen analysis apparatus D1 may be operated in the first mode (DS420). Also, if the second mode is selected, the specimen analysis apparatus D1 may be operated in the second mode.

The method of controlling the specimen analysis apparatus D1 according to the first mode is equal or similar to that according to the first embodiment, and the method of controlling the specimen analysis apparatus D1 according to the second mode is equal or similar to that according to the second embodiment. Thus, detailed descriptions with respect to the control methods according to the first and second modes will be omitted.

According to the third embodiment of the present invention, the specimen analysis apparatus D1 according to the present invention may be realized in the selectable mode to realize a mode desired according to use environments of the user, thereby improving user's convenience.

Hereinafter, a method of controlling the specimen analysis apparatus D1 according to a fourth embodiment will be described. Hereinafter, according to the fourth embodiment, a method of controlling a specimen analysis apparatus D1 in a mode that is automatically operated when a specimen analyzing kit D100 is inserted into the specimen analysis apparatus D1, unlike a method in which a mode to be operated is selected according to a user's input in a state where the specimen analysis apparatus D1 is operable in at least two modes as described in the third embodiment.

[Method of Controlling Specimen Analysis Apparatus According to Fourth Embodiment]

Figure 54:
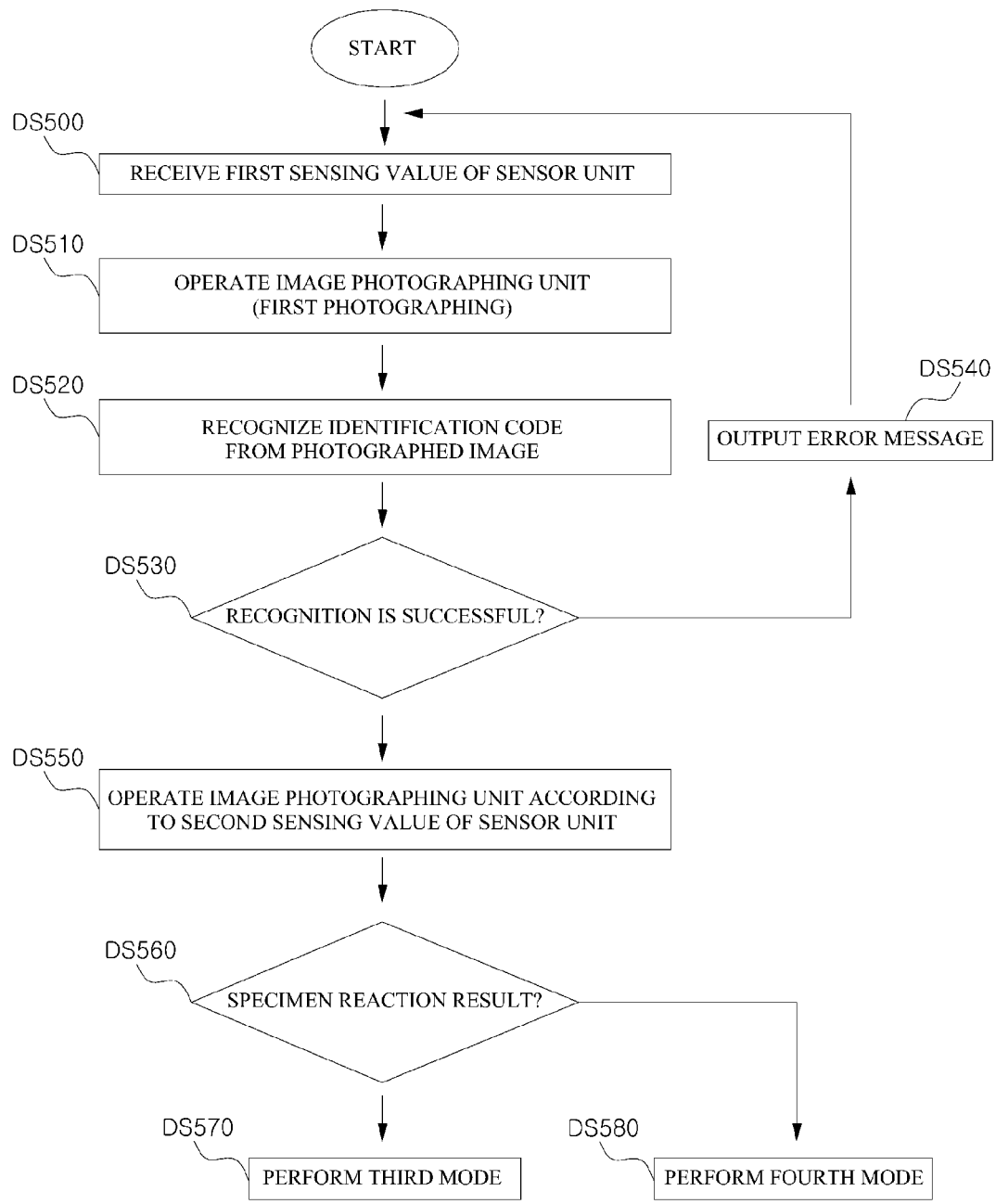
FIG. 54 is a flowchart for explaining the fourth embodiment in which the specimen analysis apparatus according to the present invention is controlled.

FIG. 54 is a flowchart for explaining the fourth embodiment in which the specimen analysis apparatus according to the present invention is controlled.

Referring to FIG. 54, a method of controlling specimen analysis apparatus D1 according to the fourth embodiment of the present invention may include a process (DS500) of receiving a first sensing value of a sensing unit D350, a process (DS510) of operating an image photographing unit D200, a process (DS520) of recognizing an identification code D110 from a photographed image, a process (DS530) of determining whether the identification code D110 is successfully recognized, and a process (D540) of outputting an error message when the recognition fails. Here, since the operations DS500 to DS540 are equal or similar to the operations DS100 to DS140 according to the first embodiment, their detailed descriptions will be omitted.

In the determination result in the operation DS530, if it is determined that the identification code D110 is normally recognized, the control unit D320 may operate the image photographing unit D200 according to a second sensing value of the sensor unit D350 (DS550). As described above, a process in which the image photographing unit D200 is operated according to the second sensing value of the sensor unit D350 to photograph a reaction area D124 is similar to the operation DS150 according to the first embodiment.

The control unit D320 may analyze an image with respect to the reaction area D124 photographed in the operation DS550 to determine whether a specimen reaction result D122 is formed in the reaction area D124 or not (DS560). That is, when the specimen analyzing kit D100 is fully mounted into the insertion unit D310, it may be determined whether the specimen reaction result D122 is formed in the reaction area D124 in at least one band shape as shown in FIG. 44, or the specimen reaction result D122 is not formed in the reaction area D124 as shown in FIG. 49.

As a result, if the specimen reaction result D122 is formed in the reaction area D124, the control unit D320 may perform a third mode (DS570). On the other hand, if the specimen reaction result D122 is not formed, the control unit D320 may perform a fourth mode (DS580).

Here, an operation in the third mode may be equal or similar to those in the operation DS160 to DS80 according to the first embodiment of the present invention. Also, an operation in the fourth mode may be equal or similar to those in the operation DS250 to DS300 according to the second embodiment of the present invention. Thus, detailed descriptions with respect to the control methods according to the third and fourth modes will be omitted.

According to the fourth embodiment of the present invention, it is unnecessary to select a mode desired by a user. That is, when the specimen analyzing kit is inserted into the specimen analysis apparatus, an operation of the specimen analysis apparatus may be controlled in operation so that a mode desired by the user is automatically selected. Thus, the user may more conveniently use the specimen analysis apparatus.

Hereinafter, a modified example of a sensor unit D350 illustrated in FIGS. 41, 44, and 46 to 48 will be described.

As described above, the sensor unit D350 may be constituted by a first sensor D352 and a second sensor D354. This is designed to output a first sensing value and a second sensing value according to an inserted position of the specimen analyzing kit D100.

However, when the specimen analyzing kit D100 is mounted at a specific position, it should not be necessary to provide at least two sensors D352 and D354 to output the first and second sensing values.

Figure 55:
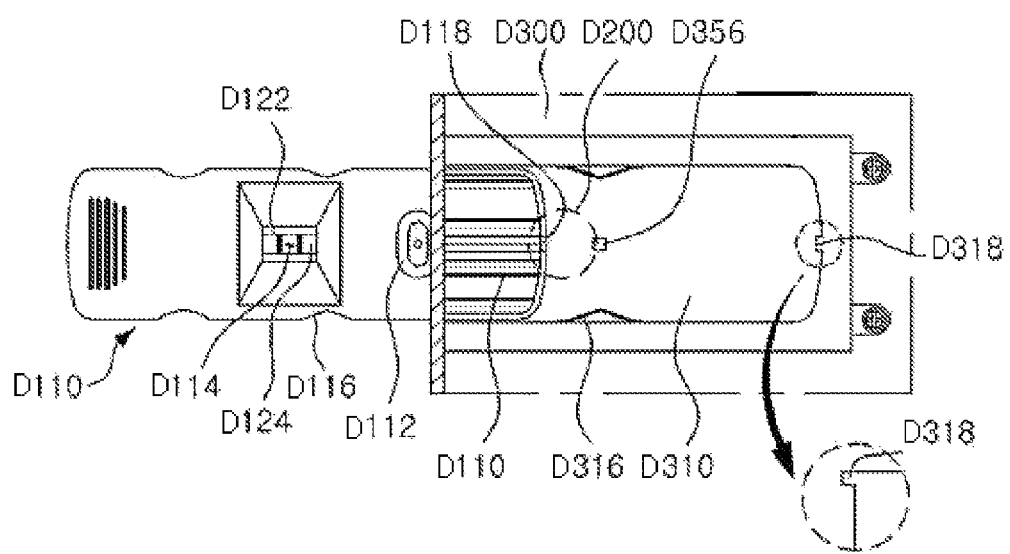
FIGS. 55 and 56 are schematic views for explaining a modified example of a sensor unit according to the present invention.
Figure 56:
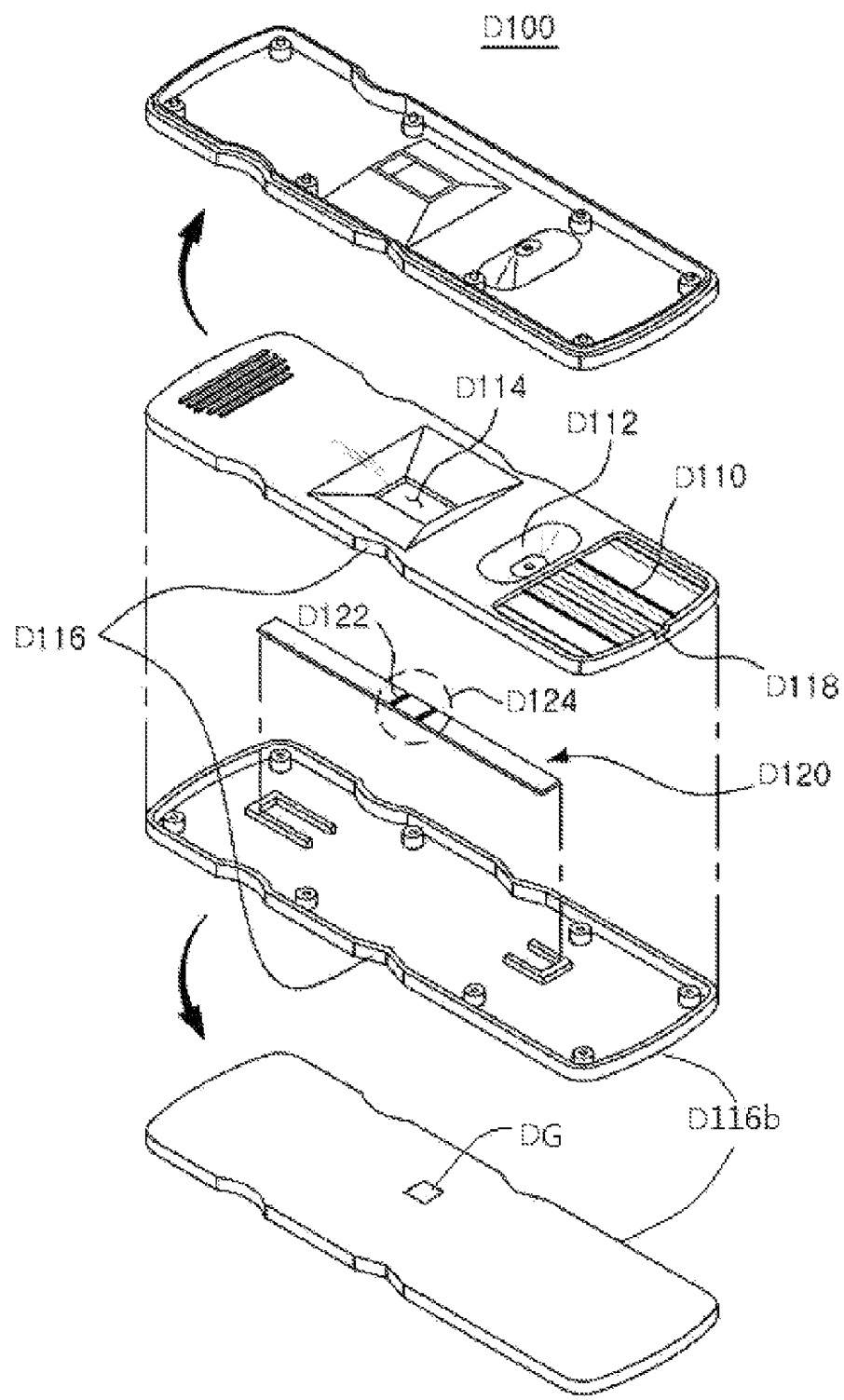

FIGS. 55 and 56 are schematic views for explaining a modified example of a sensor unit according to the present invention.

Referring to FIG. 55, it is seen that a third sensor D356 is disposed on one area of a bottom surface of the insertion unit D310. A position of the third sensor D356 may be determined in consideration of a mounted position of the image photographing unit D200 and a length of the insertion direction of the specimen analyzing kit of the identification code D110. Hereinafter, the other sensor may not be disposed at a position of the second sensor D354 illustrated in FIGS. 41, 44, and 46 to 48.

However, as shown in FIG. 56, a groove DG may be formed in an area of a cover D116*b* constituting the bottom surface of the specimen analyzing kit D100.

A position of the groove DG may be determined at a position corresponding to the third sensor D356 when the specimen analyzing kit D100 is fully mounted into the insertion unit D310.

As described with reference to FIGS. 55 and 56, when the sensor unit D350 and a bottom surface D16*b* of the specimen analyzing kit D100 are provided, the first and second sensing values may be outputted.

As the specimen analyzing kit D100 is inserted into the insertion unit D310, when an end of the specimen analyzing kit D100 contacts the third sensor D356, the third sensor D356 may output the first sensing value.

When the specimen analyzing kit D100 is fully mounted into the insertion unit D310, a position of the third sensor D356 may match with that of the groove DG. Thus, the third sensor may output the second sensing value.

As described above, the first and second sensing values may be outputted according to a position of the specimen analyzing kit D100 by using only one sensor without using two sensors. A method of outputting the first and second sensing values according to the position of the specimen analyzing kit D100 may various. Thus, modified examples of the sensor unit D350 may be included in the scope of the present invention.

Hereinafter, a method of controlling the specimen analysis apparatus D1 according to a fifth embodiment will be described.

[Method of Controlling Specimen Analysis Apparatus According to Fifth Embodiment]

Figure 57:
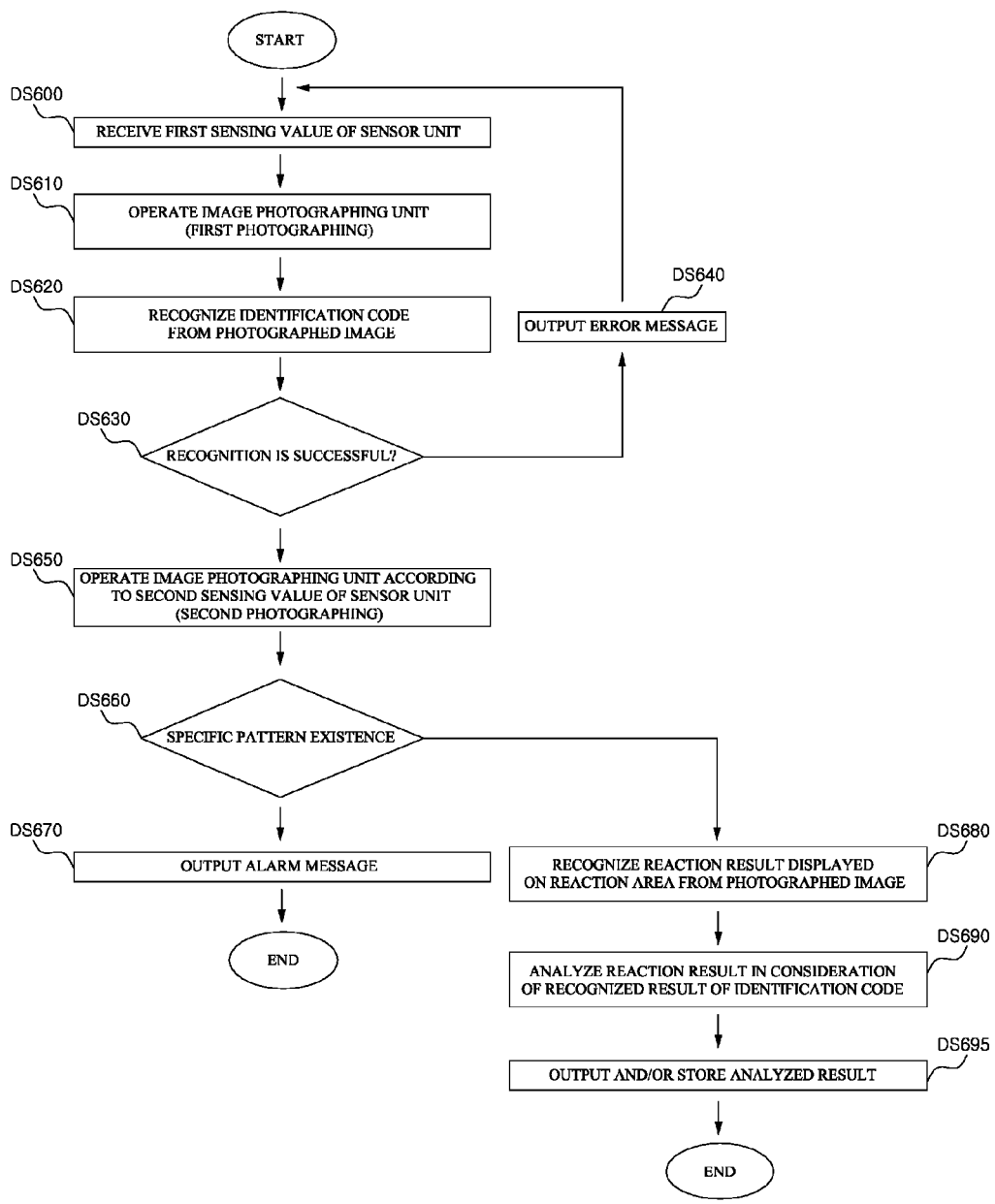
FIG. 57 is a flowchart for explaining the fifth embodiment in which the specimen analysis apparatus according to the present invention is controlled.

FIG. 57 is a flowchart for explaining the fifth embodiment in which the specimen analysis apparatus according to the present invention is controlled.

A control unit D320 provided in a specimen analysis apparatus D1 according to a fifth embodiment of the present invention may receive a sensing value from a sensor unit D350 to allow an image photographing unit D200 to photograph a reaction area D124 in which an injected specimen is introduced into a specimen analyzing kit D100, thereby determining whether a specific pattern exists on the basis of the photographed image.

Here, the specific pattern may include a different pattern in addition to the pattern generated by the specimen. For example, the specific pattern may be a pattern generated by foreign substances introduced into the reaction area.

When the specific pattern exists, the control unit D320 may output an alarm message for distinguishing the existence of the specific pattern from the outside. Thus, the specific pattern generated by the foreign substances may be excluded when health conditions of a specimen subject are analyzed.

As a result, when the specific pattern exists, the alarm message may be outputted by the control unit D320 to stop the analysis operation without further performing the analysis. Then, the specimen analyzing kit D100 may be replaced with a new specimen analyzing kit D100, and an analysis operation with respect to the new specimen analyzing kit D100 may be performed.

Here, the alarm message may be outputted through the display part D340. The display part D340 may acoustically output the alarm message to the user through an acoustic output unit (not shown) in addition to the visual output of the alarm message through the display part D340 to awaken surroundings of the user again.

Alternatively, the alarm message may be ractually outputted through a vibration output unit (not shown).

Hereinafter, a method of controlling the specimen analysis apparatus D1 according to a fifth embodiment will be described in more detail.

Referring to FIG. 57, a method of controlling specimen analysis apparatus D1 according to the second embodiment of the present invention may include a process (DS600) of receiving a first sensing value of a sensing unit D350, a process (DS610) of operating an image photographing unit D200, a process (DS620) of recognizing an identification code D110 from a photographed image, a process (DS630) of determining whether the identification code D110 is successfully recognized, and a process (D640) of outputting an error message when the recognition fails. Here, since the operations DS600 to DS640 are equal or similar to the operations DS100 to DS140 according to the first embodiment, their detailed descriptions will be omitted.

According to the determination result in operation DS630, if it is determined that the recognition is successful, the control unit D320 may receive a second sensing value from a sensor unit D350 to operate the image photographing unit D200 according to the second sensing value (DS650). Here, the photographing operation in the operation DS650 may be called second photographing.

Then, the control unit D320 may determine whether a specific pattern due to foreign substances exists on the basis of a photographed image of the reaction area D124 photographed in the operation DS650.

Here, if it is determined that the specific pattern does not exist, the reaction result in the reaction area D124 may be recognized from the photographed image (DS680), the reaction result may be analyzed in consideration of the recognized result of the identification code (DS690), and the analyzed result may be outputted and/or stored (DS695).

Since the operations DS680 to DS695 may be similar or equal to those in the operations DS160 to DS180 according to the first embodiment, their detailed description will be omitted.

If it is determined that the specific pattern exists in the operation DS670, the control unit D320 may output an alarm message for distinguishing the existence of the specific pattern from the outside (DS670).

When the alarm message is outputted, it is difficult to accurately diagnose health conditions of a specimen subject due to the specific pattern. Thus, the analysis operation may be stopped.

Thus, according to the method of controlling the specimen analysis device D1 according to the fifth embodiment, a measurement error occurring due to the foreign substances introduced into the specimen analyzing kit D100 may be previously prevented.

Finally, a method of controlling the specimen analysis apparatus D1 according to a sixth embodiment will be described below.

[Method of Controlling Specimen Analysis Apparatus According to Sixth Embodiment]

Figure 58:
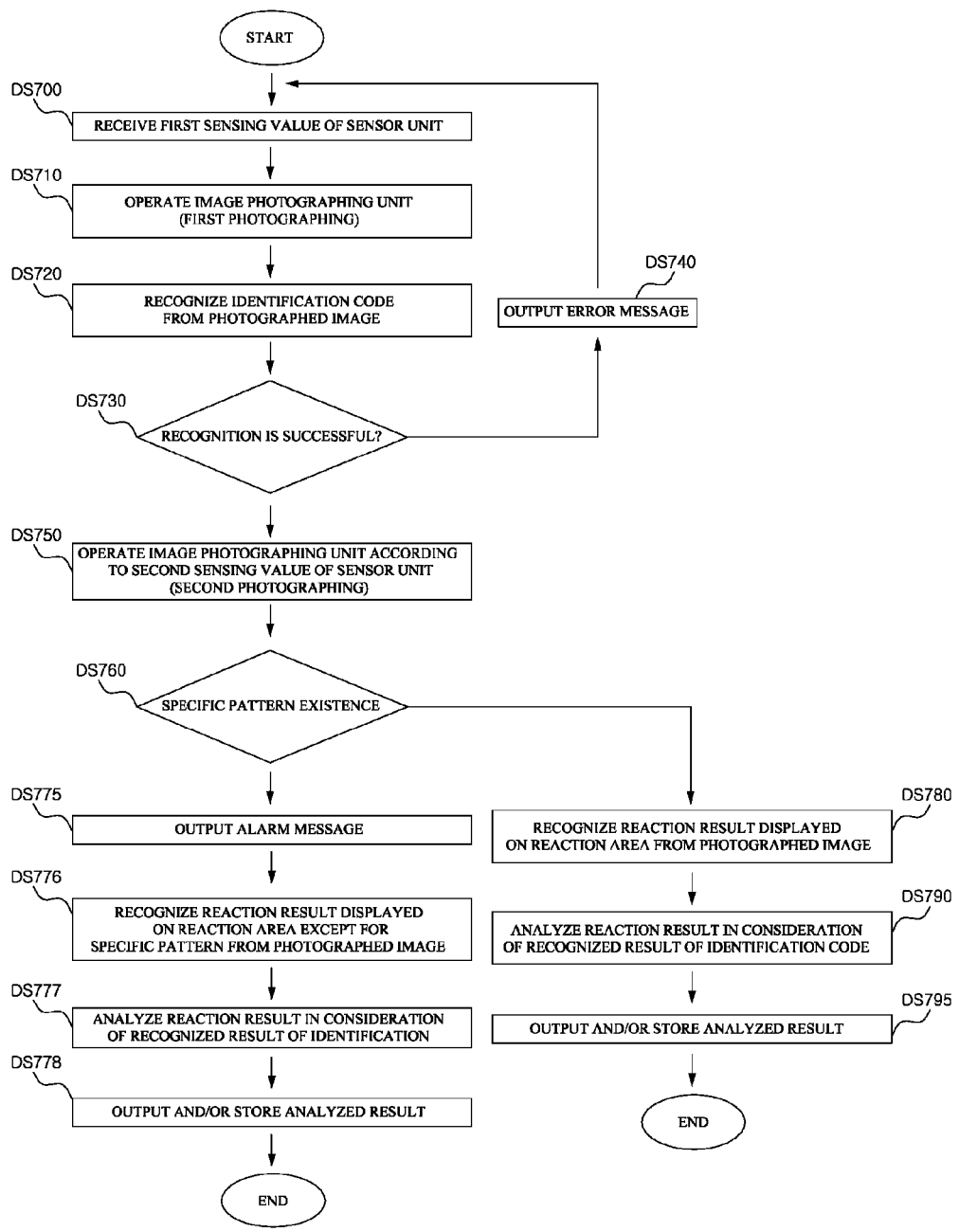
FIG. 58 is a flowchart for explaining the sixth embodiment in which the specimen analysis apparatus according to the present invention is controlled.

FIG. 58 is a flowchart for explaining the sixth embodiment in which the specimen analysis apparatus according to the present invention is controlled.

Referring to FIG. 58, since operations DS700 to DS760 and DS780 to DS795 may be similar or equal to those in the operations DS600 to DS660 and DS680 to DS695 according to the fifth embodiment, their detailed description will be omitted.

If it is determined that a specific pattern exists in the operation DS770, a control unit D320 may output an alarm message for distinguishing the existence of the specific pattern from the outside (DS775).

Here, the control unit D320 may recognize a reaction result in a reaction area D124 except for the specific pattern from a photographed image (DS776), the reaction result may be analyzed in consideration of a recognized result of an identification code (DS777), and the analyzed result may be outputted and/or stored (DS778).

Thus, according to the method of controlling the specimen analysis device D1 according to the sixth embodiment, since the specific pattern due to the foreign substance is excluded in the process of recognizing the reaction result displayed on the reaction area D124 from the photographed image to analyze the reaction area D124. Thus, a measurement error occurring due to the foreign substances may be previously prevented.

The specimen analysis apparatus D1 may store a series of information related to the analysis of the specimen analyzing kit D100.

For example, the specimen analysis apparatus D1 may perform analysis with respect to various markers (i.e., target specimen). Thus, parameter information for analyzing the various markers ma be stored in the specimen analysis apparatus D1.

For another example, different specimen analyzing kits D100 may be used to perform the analysis of the various markers. Thus, information for determining a marker analyzed by the specimen analyzing kit D100 may be stored in the specimen analysis apparatus D1. For example, the specimen analyzing kit D100 may include an identification code for distinguishing oneself by using the specimen analysis apparatus D1. Here, information with respect to the identification code may be stored in the specimen analysis apparatus D1.

For another example, information with respect to analysis environments adequate for analyzing the marker (i.e., the target specimen) may be stored in the specimen analysis apparatus D1.

As described above, when the related information is previously stored in the specimen analysis apparatus D1, the related information may be renewed or added as necessary. For example, when a kit for measuring a new marker is developed, related information for measuring the new marker should be stored in the specimen analysis apparatus D1.

Here, the specimen analysis apparatus D1 may renew or add the information through various methods.

For example, the specimen analysis apparatus D1 may receive the information to be renewed or added through a communication module (not shown).

The communication module may receive information for the outside through various communication methods. That is, the communication module may include at least one of a wireless Internet module, a near field communication module, and a wired communication module.

The Internet module may be wiredly or wirelessly connected to Internet to transmit/receive information. The Internet module may be connected to Internet to transmit/receive various information.

The Internet module may be wiredly or wirelessly connected to Internet to perform communication according to at least one of local area network (LAN), wireless LAN (WLAN), wireless broadband (Wibro), world interoperability for microwave access (Wimax), high speed downlink packet access (HSDPA), other various communication standards.

The near field communication module may perform near field wireless communication. The near field communication module may perform communication according to at least one of Bluetooth, radio frequency identification (RFID), infrared data association (IrDA), ultra wideband (UWB), ZigBee, and other near field communication standards.

When the specimen analysis apparatus D1 receives the related information to be renewed or added through the near field communication module, a separate TAG storing the related information may be provided together with a kit for analyzing the new marker. The TAG may be connected (tagged) to the near field communication module to receive the related information.

The wired communication module may wiredly connect the specimen analysis apparatus D1 to an external device.

The wired communication module may communicate with the external device through various interfaces. For example, the wired communication module may perform communication through at least one of interface devices such as a universal serial bus (USB) module that is capable of communicating through a USB port, a RS-232 standard port, a headset port, an external charger port, a data port, a memory card port, an audio I/O (input/output) port, a video I/O port, and an earphone jack.

Here, the specimen analysis apparatus D1 may receive the related information through the wired communication module from the external device in which the related information is previously stored. Here, the external device may acquire the related information through various methods.

The communication module may not perform the communication by only one communication module. As necessary, a plurality of communication modules may communicate with a plurality of external devices.

According to the case for the specimen analyzing kit and the specimen analyzing kit including the same, the specimen may be putted once to analyze multiple characteristics at the same time.

Also, it may previously prevent the specimens from interfering with each other in the process of analyzing the multiple characteristics of the specimen at the same time to obtain more accurate analysis results.

Furthermore, the low costs and high efficiency may be realized.

Also, according to the case for the specimen analyzing kit and the specimen analyzing kit including the same, the analyzed specimen analyzing kit may be stably inserted into the main body to realize accurate specimen analysis.

The specimen analysis apparatus may conclude the identification code and the measurement of the specimen reaction result by using a singular component to realize the miniaturization and simplification.

Also, since the specimen analysis apparatus according to the present invention is selectively realized in a mode desired by a user, user's convenience may be maximized.

Also, when the specimen reaction result of the specimen analyzing kit is measured, an error occurring due to the foreign substances may be previously prevented to maximize the accuracy in measurement.

While the present invention has been particularly shown and described with reference to exemplary embodiments thereof, it will be understood by those of ordinary skill in the art that various changes in form and details may be made therein without departing from the spirit and scope of the present invention as defined by the following claims.

For example, the insertion position fixing parts B130, B230, and B330, the vertical movement prevention parts B135, B235, and B335, the insertion position fixing corresponding parts B42, B42a, and B42b, and the vertical movement prevention corresponding parts B44, B44a, and B44b may be variously changed in configuration, and various kinds of sensors may be provided.

What is claimed is:

1. A specimen analysis apparatus comprising:
   a main body;
   a kit including a reaction area and an identification code on a surface of the kit, the kit having a width and a length, wherein the kit is inserted into the main body in an insertion direction along the length of the kit;
   an insertion hole in the main body for receiving the kit;
   an image photographing unit mounted in the main body, the image photographing unit photographing the identification code and the reaction area;
   a first sensor providing a first signal by detecting insertion of the kit at a first distance, the first sensor mounted in the main body;
   a second sensor providing a second signal by detecting insertion of the kit at a second distance, the second sensor mounted in the main body, wherein the first sensor and the second sensor are arranged along the insertion direction of the kit; and
   a controller mounted in the main body, the controller configured to:
      control the image photographing unit to photograph the identification code when the first signal is received from the first sensor,
      control the image photographing unit to photograph the reaction area when the second signal is received from the second sensor,
      recognize a degree of insertion of the kit into the main body by the first signal and the second signal, and
      analyze a photographed image of the reaction area by using identification information obtained from a photographed image of the identification code,
   wherein the image photographing unit photographs the identification code and the reaction area at different times.

2. The specimen analysis apparatus of claim 1, wherein the controller is further configured to control the image photographing unit to photograph the reaction area of the kit in order to detect whether or not a specimen has been injected.

3. The specimen analysis apparatus of claim 1, further comprising:
   wherein the second sensor is at a distal end of the insertion hole, and
   wherein the controller is further configured to control the image photographing unit to photograph the reaction area when the second signal is received from the second sensor.

4. A specimen analysis apparatus comprising:
   a main body;
   a kit including a reaction area and an identification code, the kit having a width and a length, wherein the kit is inserted into the main body in an insertion direction along the length of the kit;
   an insertion hole in the main body for receiving the kit;
   a first sensor mounted in the main body and detecting insertion of the kit at a first distance and a second sensor mounted in the main body and detecting insertion of the kit at a second distance, the first sensor and second sensor arranged along the insertion direction of the kit;
   an image photographing unit mounted in the main body; and
   a controller mounted in the main body, the controller configured to:
      control the image photographing unit to photograph the identification code when a first signal is received from the first sensor,
      control the image photographing unit to photograph the reaction area when a second signal is received from the second sensor,
      receive and analyze identification information of the kit on the basis of a photographed image of the identification code,
      analyze a photographed image of the reaction area based on the identification information obtained from a photographed image of the identification code, and
      recognize a degree of insertion of the kit into the main body by the first signal and the second signal.

5. A specimen analysis apparatus comprising:
   a main body;
   a kit including a reaction area and an identification code, the kit having a width and a length, wherein the kit is inserted into the main body in an insertion direction along the length of the kit;
   an insertion hole in the main body for receiving the kit;
   a first sensor mounted in the main body and detecting insertion of the kit at a first distance and a second sensor mounted in the main body and detecting insertion of the kit at a second distance, the first sensor and second sensor arranged along the insertion direction of the kit;
   an image photographing unit mounted in a main body;
   a temperature adjustment device mounted in the main body; and
   a controller mounted in the main body, the controller configured to:
      control the image photographing unit to photograph the identification code and recognize a result of the identification code when a first signal is received from the first sensor,
      control the temperature adjustment device to adjust a temperature near the reaction area on the basis of the recognized result of the identification code,
      monitor the reaction area by photographing the reaction area in consideration of the recognized result of the identification code, and
      recognize a degree of insertion of the kit into the main body by the first signal and a second signal from the second sensor.

6. The specimen analysis apparatus of claim 5, wherein the controller starts controlling the image photographing unit as the second signal is received from the second sensor.

7. The specimen analysis apparatus of claim 5, wherein the first sensor outputs the first signal when the kit is disposed at a position at which the image photographing unit is capable of photographing the identification code.

8. A specimen analysis apparatus comprising:
   a main body;
   a kit including a reaction area and an identification code, the kit having a width and a length, wherein the kit is inserted into the main body in an insertion direction along the length of the kit;
   an insertion hole in the main body for receiving the kit;
   a first sensor mounted in the main body, the first sensor detecting insertion of the kit at a first distance and a second sensor mounted in the main body, the second sensor detecting insertion of the kit at a second distance;

an image photographing unit mounted in the main body; and a controller mounted in the main body, the controller configured to:
control the image photographing unit to photograph the identification code when a first signal is received from the first sensor,
control the image photographing unit to photograph the reaction area when a second signal is received from the second sensor,
determine whether a specific pattern exists on the basis of a photographed image of the reaction area based on identification information obtained from a photographed image of the identification code, and
recognize a degree of insertion of the kit into the main body by the first signal and the second signal.

9. A specimen analysis apparatus comprising:
a main body;
a kit including a reaction area and an identification code, the kit inserted into the main body, the kit having a width and a length, wherein the kit is inserted into the main body in an insertion direction along the length of the kit;
an insertion hole in the main body for receiving the kit;
a first sensor mounted in the main body, the first sensor detecting insertion of the kit at a first distance and a second sensor mounted in the main body, the second sensor detecting insertion of the kit at a second distance;
an image photographing unit; and
a controller configured to:
select one of a plurality of modes comprising first and second modes according to a predetermined reference,
control the image photographing unit to photograph the identification code when a first signal is received from the first sensor,
control the image photographing unit to photograph the reaction area when a second signal is received from the second sensor,
analyze a photographed image of the reaction area by using identification information obtained from a photographed image of the identification code,
recognize a degree of insertion of the kit into the main body by the first signal and the second signal,
wherein the controller controls a timing of photographing by the image photographing unit according to the selected mode.

10. The specimen analysis apparatus of claim 1, wherein each of the first sensor and the second sensor provides each of the first signal and the second signal by detecting an end of the kit.

11. The specimen analysis apparatus of claim 4, wherein the controller outputs an error message when the identification information is not analyzed.

* * * * *